United States Patent
Keller et al.

(10) Patent No.: US 6,555,318 B2
(45) Date of Patent: Apr. 29, 2003

(54) METHOD FOR IDENTIFICATION OF CELL GROWTH OR DIFFERENTIATION FACTORS

(75) Inventors: Gordon M. Keller, Denver, CO (US); Robert G. Hawley, Toronto (CA); Kyunghee Choi, Baltimore, MD (US)

(73) Assignee: National Jewish Medical and Research Center, Denver, CO (US)

( * ) Notice: Subject to any disclaimer, the term of this patent is extended or adjusted under 35 U.S.C. 154(b) by 28 days.

(21) Appl. No.: 09/767,893

(22) Filed: Jan. 22, 2001

(65) Prior Publication Data

US 2002/0187548 A1 Dec. 12, 2002

Related U.S. Application Data

(60) Division of application No. 09/255,127, filed on Feb. 22, 1999, which is a division of application No. 08/570,211, filed on Dec. 11, 1995, now Pat. No. 5,874,301, which is a continuation-in-part of application No. 08/343,686, filed on Nov. 21, 1994, now Pat. No. 5,914,268, and a continuation-in-part of application No. PCT/US95/14495, filed on Nov. 21, 1995.

(51) Int. Cl.$^7$ .................. C12Q 1/68; C12P 19/34; C07H 21/04
(52) U.S. Cl. .............. 435/6; 435/91.2; 536/23.5; 536/24.31
(58) Field of Search .............. 435/6, 40.51, 325, 435/91.2; 536/23.5, 24.31, 24.33

(56) References Cited

PUBLICATIONS

Hawley et al. Oncogene 9:1912, 1994.*
Zhang et al. Cancer Research 55 :1117–1121.*
Leder et al. Development 116: 1041–1049, 1992.*
Ardavin et al., *Eur. J. Immunol.*, 22(3):859–62 (1992).
Breier et al., *Development*, 114:521–532 (1992).
Burkert et al., *New Biologist*, 3(7):698–708 (1991).
Gutierrez–Ramos et al., *Proc. Natl. Acad. Sci. USA*, 89:9171–9175 (1992).
Hawley et al., *Oncogene*, 9:1–12 (1994).
Hendrie et al., *Exp. Hematol.*, 19:1031–1037 (1991).
Keller et al., *Mol. Cell. Biol.*, 13(1):473–486 (1993).
Keller et al., *Experimental Hematology*, 22(8):773 Abstract (1994).
Lieschke et al., *Experimental Hematology*, 23:328–334 (1995).
McClanahan et al., *Blood*, 81(11):2903–2915 (1993).
Mohle et al., *J. Mehatotherapy*, 2:483–489 (1993).
Orlic, *Blood*, 84(12):3991–3994 (1994).
Schmitt et al., *Genes & Dev.*, 5:728–740 (1991).
Wang et al., *Development*, 114:303–316 (1992).
Wiles et al., *Development*, 111:259–267 (1991).

* cited by examiner

Primary Examiner—Anthony C. Caputa
Assistant Examiner—Gary B. Nickol
(74) Attorney, Agent, or Firm—Sheridan Ross P.C.

(57) ABSTRACT

The present invention relates to novel immortalized precursor cell populations derived from embryonic stem cell populations and methods to produce such cell populations. Also disclosed is an assay to identify regulatory compounds capable of controlling cell growth for therapeutic and experimental use.

15 Claims, 24 Drawing Sheets

(4 of 24 Drawing Sheet(s) Filed in Color)

ASSAY FOR PRIMATIVE HEMATOPOIETIC PRECURSORS IN EMBRYOID BODIES

A 
EMBRYOID BODIES
(DAY 3-4)

DISSOCIATE

B 
METHYLCELLUTOSE CULTURE
HIGH CELL DENSITY

4 DAYS

EMBRYOID BODIES
AND -BLAST COLONIES

INDIVIDUAL COLONY
PICKED ON DAY 3, 4, 5 OR 6

C 
CFC ASSAY

REPOPULATION OF FETAL THYMI WITH ES-DERIVED CELLS

THY 1.2

THY 1.1

METHOD FOR IDENTIFICATION OF CELL GROWTH OR DIFFERENTIATION FACTORS

CROSS-REFERENCE TO RELATED APPLICATIONS

The present application is a divisional of copending U.S. patent application Ser. No. 09/255,427, filed Feb. 22, 1999 (CPA Filing Date: Nov. 14, 2000), which is a divisional of U.S. patent application Ser. No. 08/570,211, filed Dec. 11, 1995, now U.S. Pat. No. 5,874,301, issued on Feb. 23, 1999, which is a continuation-in-part of U.S. patent application Ser. No. 08/343,686 for "Novel Embryonic Cell Populations and Methods to Isolate Such Populations", filed Nov. 21, 1994, now U.S. Pat. No. 5,914,268, Issued Jun. 22, 1999. Each of U.S. patent application Ser. No. 09/255,127, U.S. Pat. No. 5,874,301 and U.S. Pat. No. 5,914,268 is, incorporated herein by this reference in its entirety. U.S. Pat. No. 5,874,301 is also a continuation-in-part of PCT Patent Application Serial No. PCT/U595/14495 for "Novel Embryonic Cell Populations and Methods to Isolate Such Populations", filed Nov. 21, 1995, incorporated herein by this reference in its entirety.

GOVERNMENT RIGHTS

This invention was made in part with government support under HL 48834-02, awarded by the National Institutes of Health. The government has certain rights to this invention.

FIELD OF THE INVENTION

The present invention is related to novel populations of precursor cells and methods to produce such populations of cells. More particularly, the present invention relates to a population of immortalized precursor cells and the use of such populations to identify compounds capable of regulating the growth of a cell.

BACKGROUND OF THE INVENTION

Multicellular animals are derived from a clone of cells descended from a single original cell, the fertilized egg. Embryogenesis involves the division and differentiation of multipotential cells, each cell having the ability to develop into multiple cellular lineages. Phenotypically, the cells of such lineages can vary substantially, such as blood cells, muscle cells and neural cells, being specialized.

A wide spectrum of diseases may be treated based upon both the possession of a population of cells having multi-lineage potential and an understanding of the mechanisms that regulate embryonic cell development. For example, the capacity to generate a new population of hematopoietic cells is the basis of bone marrow transplantation, which is currently used as a treatment for a growing number of diseases including anemia, leukemia and breast cancer. In addition, transplantation of genetically altered multipotential cells has been considered as potential therapy for a variety of different diseases including AIDS.

One of the major barriers to both the treatment of diseases and the study of the process by which an undifferentiated embryonic cell becomes committed to a particular developmental pathway is the lack of access to populations of cells that are sufficiently multipotent to be able to develop into various lineages. In particular, much attention has been paid to the use of bone marrow stem cells as a source of multi-potential cells for therapy and experimental use. Bone marrow stem cells, however, have limited use because such populations of cells comprise a subpopulation of complex hematopoietic tissue and, therefore are rare. In addition, bone marrow stem cells have not been grown as a substantially homogeneous population in tissue culture.

Following fertilization, an egg divides over a period of days to form a blastocyst. A blastocyst includes a hollow ball of cells having an inner cell mass and a fluid-filled cavity, both encapsulated by a layer of trophoblast cells. The blastocyst then implants into the uterine wall and enters into the embryonic stage of development characterized by the formation of the placenta, the development of major internal organs and the appearance of major external body structure.

Cells from the inner cell mass of an embryo (i.e. blastocyst) can be used to derive a cell line capable of being maintained in tissue culture that is referred to as embryonic stem (ES) cells. The use of ES cells to obtain hematopoietic populations of differentiated cells has been suggested in Burkett et al., pp. 698–708. 1991, *New Biologist*, Vol. 3; Schmitt et al., pp. 728–740, 1991, *Genes and Development*, Vol. 5; Gutierrez-Ramos et al., pp. 9171–9175, 1992, Vol. 89; Keller et al., pp. 473–486, *Mol. Cell. Biol.*, Vol 13; and Breier et al., pp. 521–532, 1992, *Development*, Vol. 114. The use of ES cells to obtain endothelial populations of differentiated cells has been suggested by Wang et al., pp. 303–316, 1992, *Development,* Vol 114. Prior investigators, however, have failed to obtain populations of totipotent cells (i.e. cells that can develop into any lineage, discussed in detail below) and pluripotent cells (i.e. cells, that while unable to develop into all lineages of cells, are at least able to develop into all hematopoietic lineages, also discussed in detail below). A reason for this failure is that the ES cells were cultured under conditions in which the cells committed to a cellular lineage early in the tissue culture process. As a result, prior investigators failed to recognize a method for obtaining substantially homogeneous populations of totipotent or pluripotent embryonic cells that are useful for therapeutic or experimental use. In addition, prior investigators failed to recognize a method for inducing substantially homogeneous populations of totipotent or pluripotent cells to develop into preferred cell types.

Thus, there remains a need to develop a population of cells that are totipotent, pluripotent and precursor cells, and therefore, are capable of developing into a wide variety of cellular lineages.

SUMMARY OF THE INVENTION

The present invention relates to novel populations of precursor cells that are capable of developing into different cell types. The precursor cell populations of the present invention are particularly advantageous in that the populations can be maintained in tissue culture, and therefore the cells are useful as a therapeutic reagent and a reagent to identify compounds that control precursor cell growth and differentiation.

One embodiment of the present invention is cell population that includes (a) a HOX11 precursor cell population comprising cells having a cell surface molecule FcγRII, FcγRIII, Thy-1, CD44, VLA-4α, LFA-1β or combinations thereof; (b) a HOX11 precursor cell population comprising cells having a cell surface molecule FcγRII, FcγRIII, CD44, VLA-4α, LFA-1β or combinations thereof; (c) a HOX11 precursor cell population comprising cells having a cell surface molecule HSA, CD44, VLA-4α, LFA-1β, ICAM-1 or combinations thereof; (d) a HOX11 precursor cell population comprising cells having a cell surface molecule CD45, Aa4.1, Sca-1, HSA, FcγRII, FcγRIII, Thy-1, Mac-1, Gr-1, CD44, VLA-4α, LFA-1β or combinations thereof; and (e) a HOX11 precursor cell population comprising cells having a cell surface molecule selected from the group consisting of CD45, Aa4.1, HSA, FcγRII, FcγRIII, Thy-1, Mac-1, Gr-1, CD44, VLA-4α, LFA-1β, ICAM-1 or combinations thereof. Such a precursor cell population includes cells of a mesodermal derived cellular lineage, more particularly of hematopoietic lineage, endothelial lineage, muscle cell lineage, epithelial cell lineage and neural cell lineage. Also included in the present invention is a method to obtain a precursor cell population of the present invention, such method further discussed below.

Another embodiment of the present invention is a method to identify a regulatory factor that influences the growth of a cell, comprising: (a) contacting a HOX11 precursor cell population with a regulatory factor selected from the group consisting of a putative regulatory factor, a known regulatory factor and mixtures thereof; and (b) assessing the responsiveness of the progenitor cell population to the regulatory factor. Preferred methods to assess the responsiveness of a progenitor cell population include performing an assay, such as a proliferation assay and/or a differentiation assay.

Yet another embodiment of the present invention is directed to a method to identify a compound expressed during the development of a population of embryonic stem cells, comprising characterizing at least a portion of the cellular composition of at least one cell contained in a HOX11 progenitor cell population to identify a compound expressed during the development of a population of embryonic stem cells. Preferred compounds to be identified comprise nucleic acids, proteins, carbohydrates and lipids, with cell surface molecules, secreted molecules, cytoplasmic signal transduction molecules, and nucleic acid binding proteins being particularly preferred.

The present invention also includes a method to produce an antibody, comprising administering to an animal an effective amount of a protein and/or peptide derived from a HOX11 progenitor cell population and recovering an antibody capable of selectively binding to the protein.

The present invention also includes a method to identify a therapeutic reagent useful in the treatment of hematopoietic disorders, comprising: (a) Contacting a HOX11 progenitor cell population with a compound selected from the group consisting of a putative regulatory factor and a known regulatory factor; and (b) assessing the responsiveness of the progenitor cell population to the compound. In addition, the present invention includes a method to identify a neutralizing reagent, comprising: (a) contacting a HOX11 progenitor cell population with a known regulatory factor to produce a controlled cell population; (b) combining the controlled cell population with a neutralizing reagent, which may include a known neutralizing compound of the regulatory factor and a putative neutralizing compound of the regulatory factor; and (c) assessing the responsiveness of the progenitor cell population to the neutralizing reagent.

The present invention also includes an endothelial cell population produced by the method comprising, (1) transforming an EB cell population with a nucleic acid molecule encoding a Polyoma Middle T antigen to form Polyoma Middle T EB cells; and (2) culturing the Polyoma Middle T EB cells under conditions suitable to obtain an endothelial cell population. In particular, the present invention includes an endothelial cell population having the identifying characteristics of D4T. The present invention also includes a method to identify a hematopoietic growth factor from such an endothelial cell population.

One embodiment of the present invention is a conditioned medium comprising a cell culture supernatant recovered from a culture of an endothelial cell population produced by the method comprising, (1) transforming an EB cell population with a nucleic acid molecule encoding a Polyoma Middle T antigen to form Polyoma Middle T EB cells; and (2) culturing the Polyoma Middle T EB cells under conditions suitable to obtain an endothelial cell population. The present invention also includes various uses of a conditioned medium including, a method to identify a hematopoietic cell growth factor and a method to expand and mature a population of precursor cells.

The present invention also includes an enhanced precursor cell population, comprising a precursor cell population contacted with a cell culture supernatant recovered from a culture of an endothelial cell population produced by the method comprising, (1) transforming an EB cell population with a nucleic acid molecule encoding a Polyoma Middle T antigen to form Polyoma Middle T EB cells; and (2) culturing the Polyoma Middle T EB cells under conditions suitable to obtain an endothelial cell population, wherein the precursor cell population, when contacted with the cell supernatant results in the formation of an enhanced precursor population.

BRIEF DESCRIPTION OF THE FIGURES

The file of this patent contains at least one photograph in color. Copies of this patent with color photographs will be provided by the Patent and Trademark Office upon request and payment of the necessary fee.

FIGS. 7A and 7-B illustrates the hematopoietic potential of embryonic blast cell populations.

DETAILED DESCRIPTION OF THE INVENTION

One aspect of the present invention includes populations of pluripotent and precursor cells that are capable of developing into different cellular lineages when cultured under appropriate conditions. As used herein, the term "population" refers to cells having the same or different identifying characteristics. The term "lineage" refers to all of the stages of the development of a cell type, from the earliest precursor cell to a completely mature cell (i.e. a specialized cell). A representation of the developmental pathways of populations of embryonic cells of the present invention is shown in FIG. 1.

Figure 1:
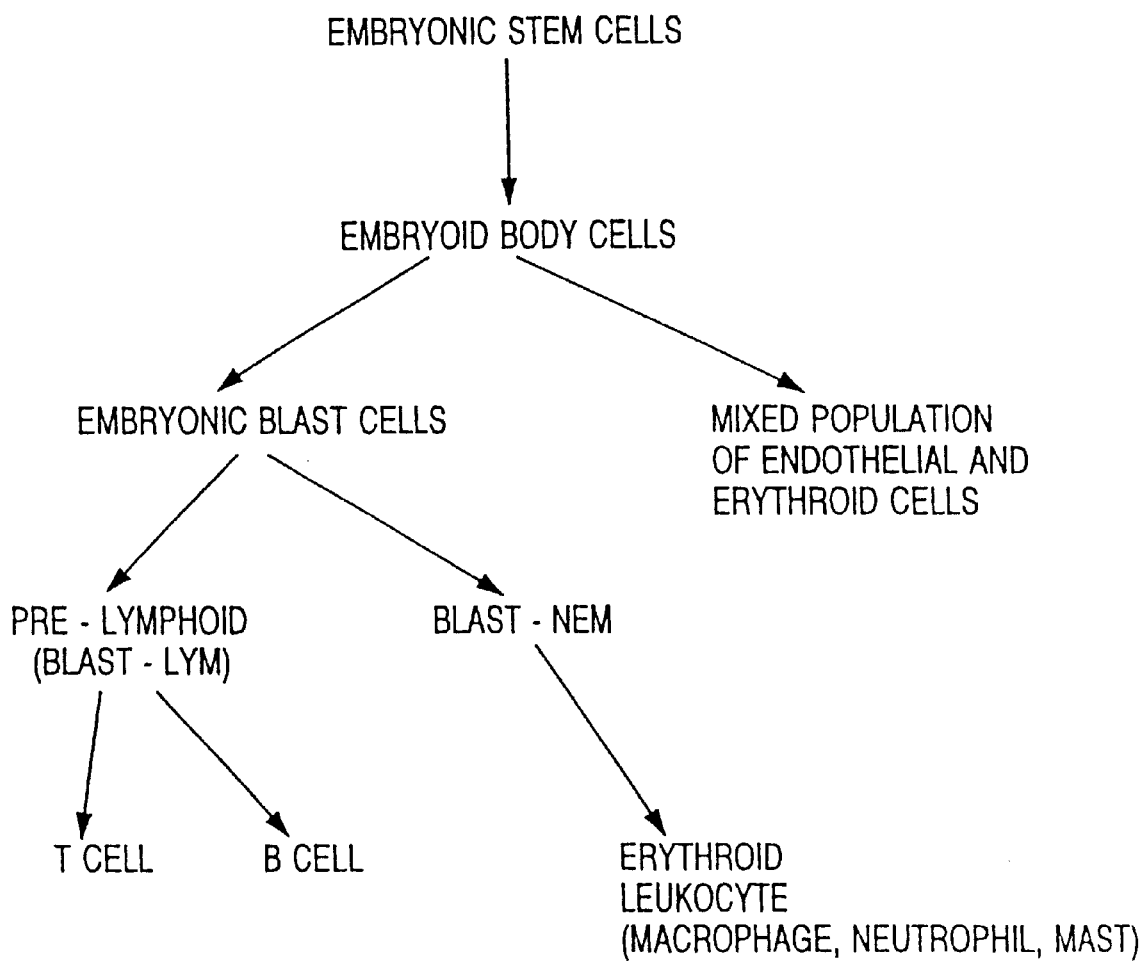
FIG. 1 is a schematic representation of the development of embryonic cell populations.

Referring to FIG. 1 and in accordance with the present invention, a population of totipotent embryonic stem (ES) cells are allowed to differentiate and generate a population of pluripotent embryoid body (EB) cells in tissue culture. A population of pluripotent EB cells of the present invention can be dissociated and re-cultured to obtain two distinct populations of cells depending on the growth factors present in the culture medium. The first population includes pluripotent embryonic blast (BLAST) cells and the second population includes a mixed population of endothelial and erythroid cells. According to the present invention, the term "growth factor" is used in its broadest context and refers to all factors that are capable of stimulating the growth of a cell, maintaining the survival of a cell and/or stimulating the differentiation of a cell.

The population of BLAST cells can be further cultured in the presence of certain growth factors to obtain a population of pre-lymphoid cells (i.e. cells capable of developing into lymphoid cells, such as T cells and B cells) referred to herein as BLAST-LYM cells. The population of blast cells can also be dissociated and re-cultured in the presence of certain growth factors to obtain a population of cells that includes erythrocytes and leukocytes other than lymphocytes. Cells in this population are referred to herein as BLAST-NEM cells. The developmental potential of the foregoing populations of cells indicate that the populations represent early stages of differentiation.

A "precursor cell" can be any cell in a cell differentiation pathway (such as shown in FIG. 1) that is capable of differentiating into a more mature cell. As such, the term "precursor cell population" refers to a group of cells capable of developing into a more mature cell. A precursor cell population can comprise cells that are totipotent, cells that are pluripotent and cells that are stem cell lineage restricted (i.e. cells capable of developing into less than all hematopoietic lineages, or into, for example, only cells of erythroid lineage). As used herein, the term "totipotent cell" refers to a cell capable of developing into all lineages of cells. Similarly, the term "totipotent population of cells" refers to a composition of cells capable of developing into all lineages of cells. Also as used herein, the term "pluripotent cell" refers to a cell capable of developing into a variety (albeit not all) lineages and are at least able to develop into all hematopoietic lineages (e.g., lymphoid, erythroid, and thrombocytic lineages). For example, a pluripotent cell can differ from a totipotent cell by having the ability to develop into all cell lineages except endothelial cells. A "pluripotent population of cells" refers to a composition of cells capable of developing into less than all lineages of cells but at least into all hematopoietic lineages. As such, a totipotent cell or composition of cells is less developed than a pluripotent cell or compositions of cells. As used herein, the terms "develop", "differentiate" and "mature" all refer to the progression of a cell from the stage of having the potential to differentiate into at least two different cellular lineages to becoming a specialized cell. Such terms can be used interchangeably for the purposes of the present application.

One aspect of the present invention is a method to produce a pluripotent population of EB cells that, when cultured under appropriate conditions, are capable of developing into a variety of cell lineages, including endothelial cell or hematopoietic lineage. A pluripotent EB cell population of the present invention can be derived by culturing a population of totipotent ES cells in an embryoid body medium including platelet-poor fetal bovine serum (PP-FBS). According to the present invention, PP-FBS refers to fetal bovine serum not having inhibitors of ES cell differentiation (e.g., TGF-β). A preferred PP-FBS of the present invention comprises fetal bovine blood from which platelets have been removed and the resulting plasma has been clotted, thereby producing platelet-poor serum. Suitable ES cells for use with the present invention include inner mass cells derived from an about 3.0 day old to about 4.0 day old blastocyst, with a blastocyst about 3.5 days old being more preferred. ES cells of the present invention are derived from an animal, preferably from a mammal, and more preferably from a human, mouse, primate, pig, cow, sheep, rabbit, rat, guinea pig or hamster.

In one embodiment, an EB cell population of the present invention is derived by culturing a population of ES cells in an embryoid body medium, which is medium that stimulates the differentiation of an ES cell population to an EB cell population. Typically, an ES cell population is maintained in an undifferentiated state by culturing the cells in an embryonic stem cell medium including leukemia inhibitory factor (LIF) and fetal calf serum (FCS). To produce an EB cell population in accordance with the present invention, an ES cell population is removed from the embryonic stem cell medium and re-cultured in embryoid body medium in which the LIF and the FCS have been replaced by either PP-FBS or normal FCS pre-selected for the ability to promote EB cell development (referred to herein as pre-selected normal FCS). Both the absence of LIF and the presence of PP-FBS or pre-selected normal FCS in the culture medium stimulates the ES cell population to differentiate into an EB cell population of the present invention. An embryoid body medium of the present invention includes a suitable amount of PP-FBS or pre-selected normal FCS that is capable of stimulating the differentiation of an ES cell population to an EB cell population. A preferred embryoid body cell medium of the present invention includes from about 5% to about 30%, more preferably from about 10% to about 20%, and even more preferably about 15% PP-FBS or pre-selected normal FCS.

Applicants have discovered that culturing of an ES cell population for a certain period of time results in the differentiation of the ES cell population to an EB cell population in which the EB cells are pluripotent. If cultured for too long, as has been done by prior investigators, the EB cell population loses pluripotency. As such, in accordance with the present invention, an EB cell population of the present invention is derived by culturing a population of ES cells for a suitable amount of time to produce a pluripotent population of EB cells. In other words, an EB cell population of the present invention is derived by culturing a population of ES cells for an amount of time that maintains an EB cell population at a stage of pluripotency. In particular, the present invention includes a population of EB cells that are derived by culturing a population of ES cells for a suitable amount of time to produce a population of EB cells that is capable of developing into an endothelial cell lineage and/or a hematopoietic cell lineage. In accordance with the present invention, an EB cell population is derived by culturing a population of ES cells from about 1 day to about 7 days. A preferred EB cell population of the present invention is derived by culturing a population of ES cells from about: 3 days to about 4 days, with from about 72 hours to 96 hours being more preferred.

In accordance with the present invention, the culture conditions are also important in obtaining a pluripotent EB cell population of the present invention from a totipotent population of ES cells. For example, an ES cell population is cultured in suspension to derive an EB cell population. During culturing, variables such as cell density, temperature and $CO_2$ levels can be controlled to maximize the development of populations of EB cells. For example, it appears that the density of cells in an ES cell culture can affect the development of an EB cell population. While not being bound by theory, it is believed that ES cell populations produce one or more growth factors that are capable of stimulating the differentiation of the ES cell population into an EB cell population. As such, the optimum cell density for the growth of an EB cell population is from about $1 \times 10^3$ ES cells per ml to about $100 \times 10^3$ ES cells per ml, more preferably from about $2 \times 10^3$ ES cells per ml to about $10 \times 10^3$ ES cells per ml, and even more preferably from about $3 \times 10^3$ ES cells per ml to about $4.5 \times 10^3$ ES cells per ml. The optimum temperature for the development of an EB cell population is from about 35° C. and about 39° C., preferably from about 36° C. and 38° C., with a temperature of 37° C. being even more preferred. The optimum $CO_2$ levels in the culturing environment for the development of EB cell populations is from about 3% $CO_2$ to about 10% $CO_2$, more preferably from about 4% $CO_2$ to about 6% $CO_2$, and even more preferably about 5% $CO_2$.

In a preferred embodiment, an EB cell population of the present invention is derived by culturing a population of ES cells in an embryoid body medium including Iscove's Modified Dulbecco's Medium (IMDM), with about 15% PP-FBS (obtained from Antech, TEXAS), monothiolglycerol (MTG), transferrin, glutamine, at a cell density of about $4.5 \times 10^3$ cells per ml of medium. The ES cell population is then cultured for about 96 hours, at about 37° C., in an about 5% $CO_2$-containing environment to obtain a population of pluripotent EB cells.

An EB cell population of the present invention is capable of developing into cells of mesodermal cell lineage, of ectodermal cell lineage or of endodermal cell lineage. As used herein, mesodermal cells include cells of connective tissue, bone, cartilage, muscle, blood and blood vessel, lymphatic and lymphoid organ, notochord, pleura, pericardium, peritoneum, kidney and gonad. Ectodermal cells include epidermal tissue cells, such as those of nail, hair, glands of the skin, the nervous system, the external sense organs (e.g., eyes and ears) and mucous membranes (such as those of the mouth and anus). Endodermal cells include cells of the epithelium such as those of the pharynx, respiratory tract (except the nose), digestive tract, bladder and urethra cells. Preferred cells within an EB cell population of the present invention include cells of at least one of the following cellular lineages: hematopoietic cell lineage, endothelial cell lineage, epithelial cell lineage, muscle cell lineage and neural cell lineage. More preferred cells within an EB cell population of the present invention include cells of erythroid lineage, endothelial lineage, leukocyte lineage and thrombocyte lineage. Even more preferred cells within an EB cell population of the present invention include cells of erythroid lineage (including primitive and definitive erythroid lineages), macrophage lineage, neutrophil lineage, mast cell lineage, megakaryocyte lineage, natural killer cell lineage, eosinophil lineage, T cell lineage, endothelial cell lineage and B cell lineage.

Figure 2:
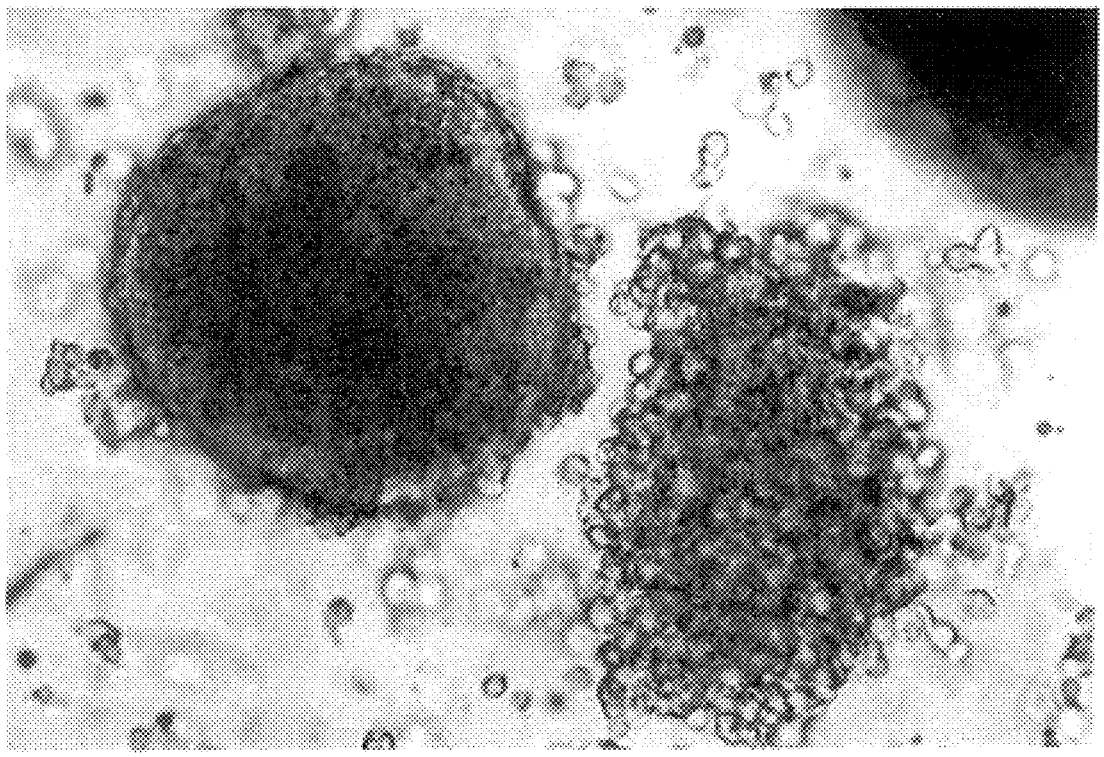
FIG. 2 shows a representative microscopic field of view of an embryoid body population and an embryonic blast cell population.

An EB cell population of the present invention includes a colony of cells having substantially the same morphology as the colony of cells shown in FIG. 2, cell colony A. The EB cell population shown in FIG. 2, cell colony A, was obtained when ES cells were grown as described in Example 1. Referring to FIG. 2, the EB cell population shown as cell colony A has a general morphology of tightly packed cells, in which individual cells are not easily detectable.

Figure 3A:
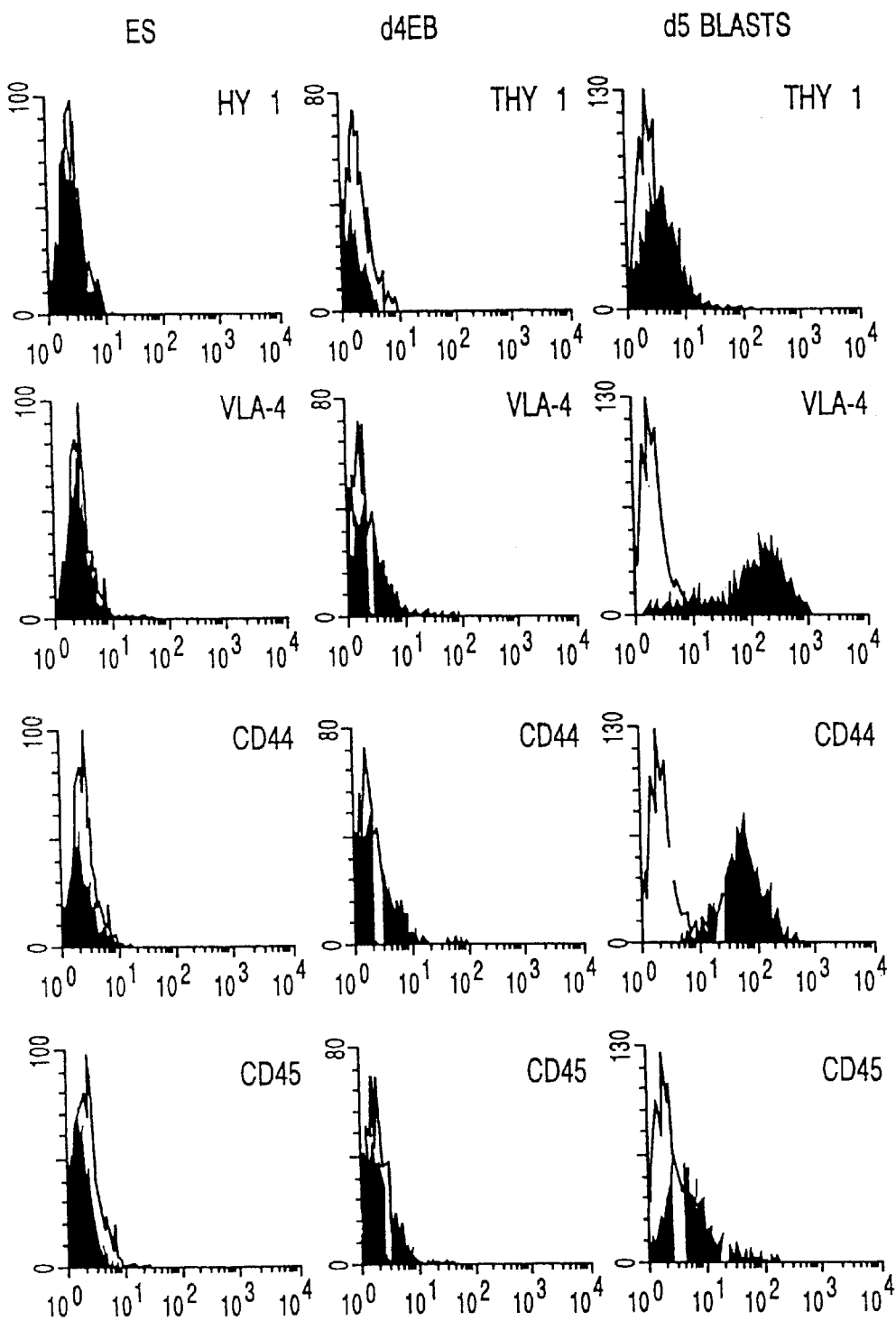
FIGS. 3A and 3B illustrates cell surface marker staining of an embryonic stem cell population, a Day 4 embryoid body population and a Day 6 embryonic blast cell population.
Figure 3B:
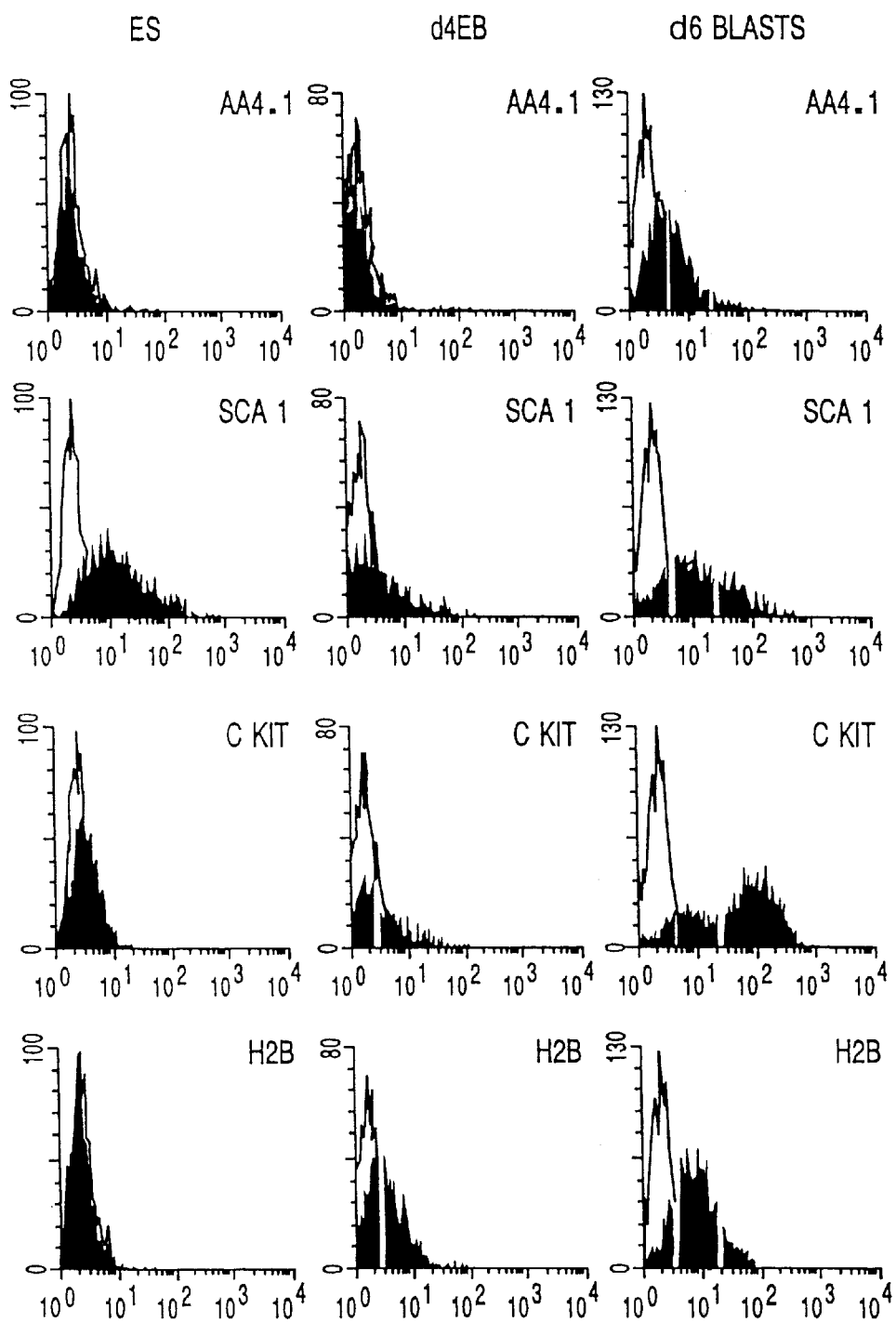

An EB cell population of the present invention that has been derived by culturing a population of ES cells for 4 days (i.e. Day 4 EB) can include cells that have substantially the same antibody staining pattern as shown in FIGS. 3A and 3B, when such EB cells are stained according to the method described in Example 2. Referring to FIGS. 3A and 3B, a Day 4 EB cell population expresses substantially low amounts of Sca-1, C-kit receptor and Class I H-2b, and essentially no Thy 1, VLA-4, CD44 and CD45.

Another aspect of the present invention is a method to produce a cell type, such as a mesodermal cell, an ectodermal cell and/or an endodermal cell that includes the steps of: (a) selecting a desired cell type to produce; and (b) culturing an embryoid body cell population of the present invention under conditions suitable to obtain the desired cell type. Suitable culture conditions for obtaining a desired cell type include culturing the EB cell population in a medium including a growth factor that is able to stimulate the EB cell population to differentiate to the desired cell type(s). As used herein, the term "a" refers to "at least one", or "one or more." For example, an EB cell population can be cultured in a medium including a growth factor capable of promoting the differentiation of the cell population into a hematopoietic cell type. A preferred culture condition for obtaining a desired cell type that includes erythroid and endothelial cells includes culturing an EB cell population of the present invention in the presence of erythropoietin (EPO) and vascular endothelial growth factor (VEGF; described in detail below). Another preferred culture condition for obtaining a desired cell type of embryonic blast cells includes culturing an EB cell population of the present invention in the presence of C-kit ligand, interleukin 1 (IL-1), interleukin 3

(IL-3), interleukin 6 (IL-6), interleukin 11 (IL-11), EPO, VEGF, and mixtures thereof, to obtain a cell of a particular cell type (described in detail below).

In the mouse, the first visible signs of blood cell development are the appearance of foci or red blood cells in a tissue called the yolk sac at 7.5 days of gestation. These early appearing red blood cells are primitive erythroid cells. Cells which are destined to make blood vessels, the endothelial cells, appear at almost the same time and in the same location as such embryonic red blood cells. Without being bound by theory, it is believed that the parallel appearance of the two types of cells in close proximity indicates that the two cell types develop from a common precursor. Prior investigators, however, have merely theorized about the existence of such a precursor cell population and have not taught or enabled the isolation of the population. Applicants have identified for the first time a population of precursor cells that are able to develop into endothelial and erythroid lineages.

One aspect of the present invention is a method to produce a mixed population of erythroid and endothelial cells by culturing a population of pluripotent EB cells of the present invention in an endothelial/erythroid cell medium, which is medium that stimulates the differentiation of an EB cell population of the present invention to a population of erythroid and endothelial cells. An endothelial/erythroid cell medium of the present invention includes a suitable amount of a growth factor capable of stimulating the development of an EB cell population into a mixed population of endothelial cells and erythroid cells. A preferred endothelial/erythroid cell medium of the present invention includes a hematopoietic cell growth factor, an endothelial cell growth, factor, homologues of such growth factors, or mixtures of such growth factors and/or homologues. A more preferred endothelial/erythroid cell medium of the present invention includes C-kit ligand, EPO and VEGF, homologues of such growth factors, or mixtures of such growth factors and/or homologues. An even more preferred cell medium of this embodiment of the present invention includes EPO and VEGF.

According to the present invention, an endothelial/erythroid cell medium of the present invention includes a suitable growth factor, and PP-FBS or pre-selected normal FCS. A preferred endothelial/erythroid cell medium of the present invention includes from about 5% to about 30%, more preferably from about 7% to about 20%, and even more preferably about 10% PP-FBS or pre-selected normal FCS.

Also according to the present invention, an EB cell population of the present invention is preferably cultured in methyl cellulose to obtain a mixed population of endothelial and erythroid cells. A suitable amount of methyl cellulose for culturing EB cell populations is an amount that enables the EB cells to associate as groups (i.e. clumps or clusters) of cells, thereby stimulating growth and/or differentiation of the EB cells into cells. A preferred amount of methyl cellulose in which to culture an EB cell population of the present invention to obtain a mixed population of endothelial and erythroid cells is from about 0.25% to about 2%, more preferably from about 0.5% to about 1.5%, and even more preferably at about 1%.

Also according to the present invention, an EB cell population of the present invention is cultured in an endothelial/erythroid cell medium for a sufficient amount of time to allow the EB cell population to differentiate to a mixed population of endothelial and erythroid cells. A preferred amount of time to culture an EB cell population is from about 5 days to about 12 days. A more preferred amount of time to culture an EB cell population is from about 6 days to about 11 days. An even more preferred amount of time to culture an EB cell population is from about 7 days to about 10 days.

Other culture conditions (i.e. in addition to time and medium) which can effect the development of a mixed population of endothelial and erythroid cells of the present invention from an EB cell population of the present invention includes the temperature and $CO_2$ content of the culture environment. The optimum temperature for the development of a mixed population of endothelial and erythroid cells of the present invention is from about 35° C. to about 39° C., preferably from about 36° C. to 38° C., with a temperature of 37° C. being even more preferred. The optimum $CO_2$ levels in the culturing environment for the development of a mixed population of endothelial and erythroid cells is from about 3% $CO_2$ to about 10% $CO_2$, more preferably from about 4% $CO_2$ to about 6% $CO_2$, and even more preferably about 5% $CO_2$.

A mixed population of endothelial and erythroid cells of the present invention is derived by culturing a population of EB cells at a suitable cell density to produce a mixed population of endothelial and erythroid cells. The optimum cell density for the growth of the population is preferably from about $5 \times 10^4$ cells to about $7.5 \times 10^5$ EB cells, more preferably from about $1.5 \times 10^5$ cells to about $6 \times 10^5$ EB cells, and even more preferably from about $2 \times 10^5$ cells to about $5 \times 10^5$ EB cells per ml of culture medium.

In a preferred embodiment, a mixed population of endothelial and erythroid cells of the present invention is derived by culturing a population of EB cells of the present invention in an endothelial/erythroid cell medium including IMDM, with about 10% PP-FBS, 1% methyl cellulose, and a mixture of growth factors including VEGF and EPO for about 7 days, at about 37° C., in an about 5% $CO_2$-containing environment to obtain a mixed population of endothelial and erythroid cells.

In one embodiment, a mixed population of endothelial and erythroid cells includes one or more cells of endothelial lineage or erythroid lineage. A preferred mixed population of endothelial and erythroid cells includes one or more cells that can be stained with von Willebrand factor according to the method described in Example 10, and/or one or more cells that can absorb diI-acetylated-low density lipoproteins when labelled according to the method described in Example 10.

Figure 4:
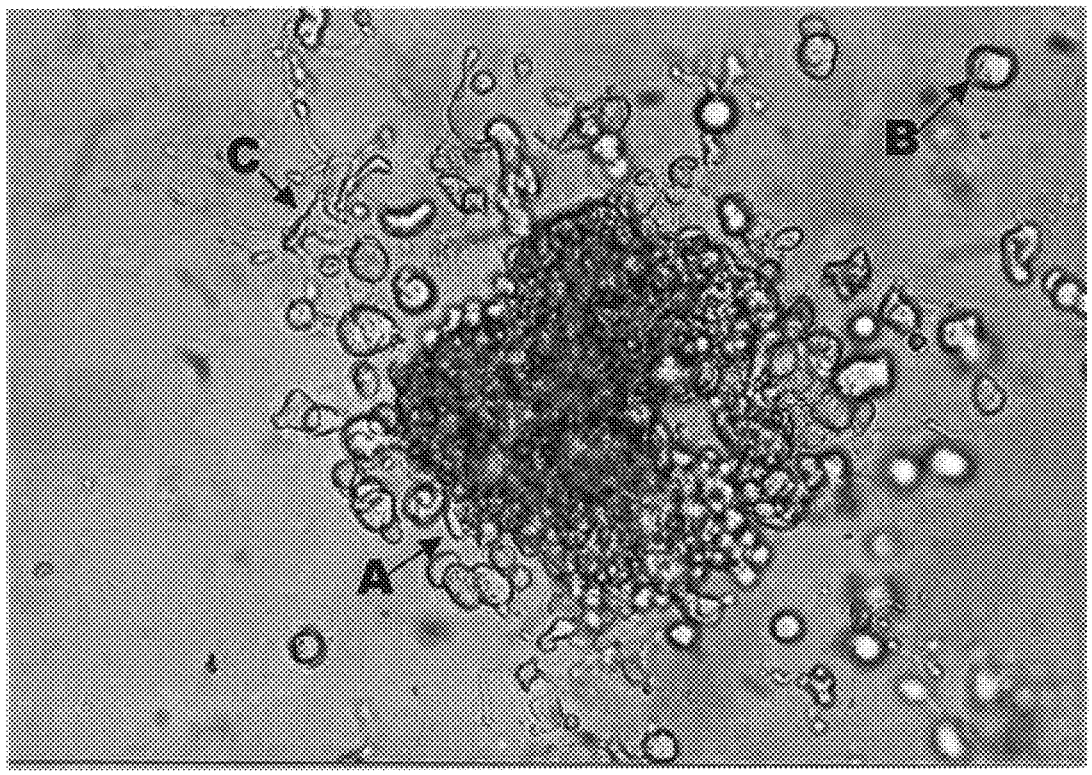
FIG. 4 shows a representative microscopic field of view of a mixed population of erythroid and endothelial cells.

A mixed population of endothelial and erythroid cells of the present invention includes one or more cells having a substantially similar morphology as the cells shown in FIG. 4.

Referring to FIG. 4, generally 3 types of cells having different morphologies can be found in a mixed population of endothelial and erythroid cells of the present invention. A first cell type, indicated as cell A in FIG. 4, comprises an erythroid cell having the typical characteristics of a distinct compact cluster of small cells having red color. A second cell type, indicated as cell B in FIG. 4, comprises a spherical cell having a larger size than an erythroid cell, such as cell A. A third cell type, indicated as cell C in FIG. 4, comprises a spherical cell having a similar size as an erythroid cell but having a single long process extending from the cell. According to the present invention, both the second cell type (i.e. cell B in FIG. 4) and the third cell type (i.e. cell C in FIG. 4) can be stained with von Willebrand factor and can absorb diI-acetylated-low density lipoproteins, thereby indicating that such cell types are representative of endothelial cells.

The present invention also includes an endothelial cell population made by the method comprising: (1) transforming an EB cell population of the present invention with a nucleic acid molecule encoding a Polyoma Middle T antigen to form Polyoma Middle T EB cells; and (2) culturing the Polyoma Middle T EB cells under conditions suitable to obtain an endothelial cell population. A preferred EB cell population comprises an ES cell population cultured for no more than about 8 days, preferably from about 2 days to about 8 days. A more preferred EB cell population comprises an ES cell population cultured for no more than about 6 days, preferably from about 3 days to about 6 days. An even more preferred EB cell population comprises an ES cell population cultured for about 4 days, using the culture conditions for EB cell formation that are described in detail herein.

Methods for transformation and expression of Polyoma Middle T antigen in an EB cell population of the present invention include subcloning a nucleic acid molecule encoding Polyoma Middle T antigen into a retroviral vector, producing virus and infecting an EB cell population with the retrovirus using methods standard to those in the art. A preferred nucleic acid molecule encoding Polyoma Middle T antigen comprises a full-length Polyoma Middle T antigen gene as disclosed in Williams et al. (*Cell* 52:121–131, 1988). A preferred retroviral vector of the present invention comprises an N2 vector (described in Keller et al., *Nature* 318:149–154, 1985).

According to the present invention, a suitable culture condition for obtaining an endothelial cell population of the present invention includes culturing Polyoma Middle T antigen transformed EB cells in culture medium comprising one or more growth factors as disclosed herein. A more preferred culture medium comprises endothelial cell growth supplement.

In accordance with the present invention, the medium also includes normal FCS, in addition to one or more growth factors described above. A preferred concentration of normal FCS to include in the medium of the present invention includes from about 10% and about 25%, more preferably from about 12% to about 20%, and even more preferably about 10% normal FCS.

Other culture conditions (i.e. in addition to time and medium) which can effect the development of an endothelial population of the present invention include the temperature and $CO_2$ content of the culture environment as disclosed in detail herein.

In a preferred embodiment, an endothelial cell population of the present invention is derived by culturing a population of Polyoma Middle T antigen transformed EB cells of the present invention in a medium including IMDM, with about 10% normal FCS, and endothelial cell growth supplement. The transformed EB cell population is grown a cell density of from about $1 \times 10^5$ cells per ml of medium to about $5 \times 10^5$ cells per ml of medium for about 2 months at about 37° C., in an about 5% $CO_2$-containing environment.

An endothelial cell population derived by the foregoing method includes cells expressing cell surface markers characteristic of endothelial cells. In particular, an endothelial cell population comprises cells expressing Flk-1 and/or CD31. In addition, an endothelial cell population comprises cells that can absorb diI-acetylated-low density lipoproteins.

In a preferred embodiment, an endothelial cell population of the present invention includes a cell population having the identifying characteristics of D4T (described in detail in Example 18).

It is within the scope of the present invention that a retrovirally transformed endothelial cell of the present invention can be used to identify one or more known and/or unknown compounds contained in the conditioned medium that are useful for enhancing a cell population of the present invention. As used herein, the term "enhancing" refers to increasing the growth and/or the differentiation (i.e., maturation) of a cell population in the presence compared with in the absence of a compound. Preferred compounds to identify using a retrovirally transformed endothelial cell population of the present invention include: (1) unknown compounds having hematopoietic growth factor activity, either alone or in combination with a known hematopoietic growth factor; and (2) unknown factors that induce prehematopoietic cells to develop into hematopoietic cells. Such compounds can be identified using any method standard in the art. For example, RNA expression in the cells can be analyzed for the presence or absence of RNA transcripts encoding known compounds by using probes specific for the nucleotide sequence of such compounds. In addition, standard expression cloning techniques (as described in Sambrook et al., ibid.) to identify nucleic acid sequences encoding both known and unknown compounds.

Another aspect of the present invention is a method to produce a pluripotent population of BLAST cells that, while unable to develop into all lineages of cells, are at least able to develop into all hematopoietic lineages, when cultured under appropriate conditions. In one embodiment, a pluripotent BLAST cell population of the present invention can be derived by culturing a population of pluripotent EB cells of the present invention in an embryonic blast cell medium, which is medium that stimulates the differentiation of an EB cell population of the present invention to a BLAST cell population of the present invention. An embryonic blast cell medium of the present invention includes a suitable amount of a growth factor capable of stimulating the development of an EB cell population into a pluripotent BLAST cell population. A preferred embryonic blast cell medium of the present invention includes a hematopoietic cell growth factor, an endothelial cell growth factor or a mixture thereof. As used herein, a homologue of a specific growth factor refers to a compound that is capable of having substantially similar activity as that growth factor; i.e. a homologue of a growth factor is substantially similar to that growth factor. For example, a homologue of a specific growth factor can bind to the cell surface receptor of that growth factor in such a manner that the surface receptor is stimulated to induce an appropriate cellular function similar to that effected by the specific growth factor. A more preferred embryonic blast cell medium of the present invention includes C-kit ligand, IL-1, IL-3, IL-6, IL-11, EPO, VEGF, homologues of such growth factors, or mixtures of such growth factors and/or homologues. An even more preferred embryonic blast cell medium of the present invention includes a mixture of C-kit ligand, IL-1, IL-6 and IL-11; a mixture of C-kit ligand, EPO and VEGF; or C-kit ligand alone.

In accordance with the present invention, an embryonic blast cell medium includes PP-FBS or pre-selected normal FCS in addition to one or more growth factors described above. A preferred embryonic blast cell medium of the present invention includes from about 5% and about 20%, more preferably from about 7% to about 15%, and even more preferably about 10% PP-FBS or pre-selected normal FCS.

Also according to the present invention, an EB cell population of the present invention is cultured in methyl cellulose to obtain a population of BLAST cells of the present invention. A suitable amount of methyl cellulose for culturing EB cell populations is an amount that enables the EB cells to associate as groups (i.e. clumps or clusters) of cells, thereby stimulating growth and/or differentiation of the EB cells into BLAST cells. A preferred amount of methyl cellulose in which to culture an EB cell population of the present invention is from about 0.25% to about 2.0%, more preferably from about 0.5% to about 1.5%, and even more preferably at about 1%.

A BLAST cell population of the present invention is derived by culturing a population of EB cells at a suitable cell density to produce a pluripotent population of BLAST cells. The optimum cell density for the growth of a BLAST cell population is preferably from about $1\times10^5$ cells to about $7.5\times10^5$ EB cells, more preferably from about $1.5\times10^5$ cells to about $6\times10^5$ EB cells, and even more preferably from about $2\times10^5$ cells to about $5\times10^5$ EB cells per ml of culture medium.

Applicants have discovered that culturing of an EB cell population for a certain period of time in accordance with the present invention results in the differentiation of an EB cell population to a BLAST cell population in which the BLAST cells are pluripotent. If cultured for too long, as has been done by prior investigators, the BLAST cell population loses pluripotency. As such, a BLAST cell population of the present invention is derived by culturing a population of EB cells for a suitable amount of time to produce a pluripotent population of BLAST cells. In particular, a population of EB cells are cultured for a suitable amount of time to produce a population of BLAST cells that is capable of developing into any hematopoietic cell lineage. In other words, a BLAST cell population of the present invention is derived by culturing a population of EB cells for an amount of time that maintains a BLAST cell population at a stage of pluripotency. A preferred BLAST cell population is derived by culturing a population of EB cells from at least about 2 days to about 15 days. A more preferred BLAST cell population of the present invention is derived by culturing a population of EB cells from about 3 days to about 10 days. An even more preferred BLAST cell population of the present invention is derived by culturing a population of EB cells from about 3 days to about 6 days.

Other culture conditions (i.e. in addition to time and medium) which can effect the development of a BLAST cell population of the present invention from an EB cell population of the present invention include the temperature and $CO_2$ content of the culture environment. The optimum temperature for the development of a BLAST cell population of the present invention is from about 35° C. to about 39° C., preferably from about 36° C. to about 38° C., with a temperature of about 37° C. being even more preferred. The optimum $CO_2$ levels in the culturing environment for the development of BLAST cell populations is from about 3% $CO_2$ to about 10% $CO_2$, more preferably from about 4% $CO_2$ to about 6% $CO_2$, and even more preferably about 5% $CO_2$.

In a preferred embodiment, a BLAST cell population of the present invention is derived by culturing a population of EB cells of the present invention in an embryonic blast cell medium including IMDM, with about 10% PP-FBS, 1% methyl cellulose, and either a mixture of growth factors including IL-1, IL-6, IL-11, C-kit ligand, EPO and VEGF, or C-kit ligand alone. The EB cell population is grown a cell density of from about $2\times10^5$ cells per ml of medium to about $5\times10^5$ cells per ml of medium. After reaching that density, the EB cell population is then cultured for about 6 days, at about 37° C., in an about 5% $CO_2$-containing environment to obtain a population of pluripotent BLAST cells.

In another preferred embodiment, an EB cell population of the present invention is grown in a culture medium comprising conditioned medium derived from the supernatant of endothelial cell cultures. According to the present invention, endothelial cell conditioned medium is produced by culturing an endothelial cell population of the present invention in a culture medium suitable for the growth of an endothelial cell population until the cells become confluent in the culture dish. The supernatant from the cultures are recovered using methods standard in the art to obtain conditioned medium.

A suitable endothelial cell population useful for the production of conditioned medium includes an endothelial cell population derived from an EB cell population of the present invention. Preferably, a conditioned medium of the present invention is derived from an endothelial cell population produced using a retrovirally transformed EB cell population of the present invention. A particularly preferred endothelial cell population useful for the production of conditioned medium includes a cell population having the identifying characteristics of a D4T cell population.

Suitable medium for the growth of endothelial cells includes culture medium comprising one or more growth factors described herein, preferably, an endothelial cell growth supplement (ECGF). An endothelial cell culture medium preferably comprises from about 12 μg/ml to about 300 μg/ml, more preferably from about 25 μg/ml to about 200 μg/ml and even more preferably from about 50 μg/ml to about 100 μg/ml ECGF.

A preferred conditioned medium of the present invention, when added to a 3 day EB cell population, is capable of enhancing (i.e. stimulating the growth and/or differentiation) of a BLAST cell population of the present invention about 2-fold when a conditioned medium is added to a culture of about $5\times10^4$ cells from a 3 day EB cell population, about 5-fold when a conditioned medium is added to a culture of about $1.7\times10^4$ cells from a 3 day EB cell population and about 23-fold when a conditioned medium is added to a culture of about $6\times10^3$ cells from a 3 day EB cell population, when the culture is performed under conditions suitable for the development of a BLAST cell population. Preferably, the EB cell population culture medium comprises VEGF, EPO, C-kit ligand or mixtures thereof.

In a preferred embodiment, a conditioned medium of the present invention includes medium recovered from about 72 hour cultures of D4T cells grown in culture medium comprising ECGF. It is within the scope of the present invention that a characteristic of a D4T cell population is the ability to produce compounds that condition a medium in such a manner that the conditioned medium is capable of enhancing a BLAST cell population in the manner disclosed herein.

It is within the scope of the present invention that a conditioned medium of the present invention can be used to identify one or more known and/or unknown compounds contained in the conditioned medium that are useful for enhancing the growth of a cell population of the present invention. Preferred compounds to identify using a conditioned medium of the present invention include: (1) unknown compounds having hematopoietic growth factor activity, either alone or in combination with a known hematopoietic growth factor; and (2) unknown factors that induce pre-hematopoietic cells to develop into hematopoietic cells. Such compounds can be identified using any method standard in the art. For example, immunoassays can be used to identify the presence of known compounds in a conditioned medium of the present invention. Alternatively, standard biochemical protein separation techniques (e.g., antibody binding studies, gel electrophoresis and various chromatography techniques, in particular HPLC, known to those of skill in the art) can be used to identify and isolate individual or families of proteins from a conditioned medium. The ability of an unknown compound to effect cell growth can be tested using, for example, the method described in Example 18. Various types of cell growth assays are applicable in this situation and that any cell population of the present invention can be employed in such assays.

It is also within the scope of the present invention that a conditioned medium of the present invention can be used to enhance precursor populations of cells, preferably human hematopoietic precursor cells. As such, a conditioned medium of the present invention is capable of enhancing the growth and/or differentiation of a cell population including totipotent, pluripotent and/or stem cell lineage restricted cells. Such cells include, for example, fetal, embryonic and adult organ cells. Enhancement of precursor populations of cells is particularly useful in the treatment of diseases that involve replenishing precursor cell populations in a subject. For example, cancer patients undergoing chemotherapy, radiotherapy and/or bone marrow transplants are preferred recipients of precursor cell populations enhanced using a conditioned medium of the present invention.

Precursor cell populations can be enhanced by culturing such cells under suitable culture conditions in the presence of an effective amount of conditioned medium. One can determine the culture conditions and amount of conditioned medium to used based upon parameters, such as the cell type being expanded, the health of the cells being expanded and the extent of expansion required.

The scope of the invention also includes an enhanced precursor cell population, comprising a precursor cell population (i.e. a population of cells comprising precursor cells) contacted with a conditioned medium of the present invention, wherein the step of contacting results in the formation of an enhanced precursor population. Preferably, an enhanced precursor cell population comprises about 2-fold, more preferably about 5-fold and even more preferably about 20-fold more cells than the precursor cell population. A particularly preferred precursor cell population comprises a human precursor cell population.

Being pluripotent, a BLAST cell population of the present invention includes cells of hematopoietic and other cell lineages. In particular, a BLAST cell population of the present invention includes cells of erythroid lineage, endothelial lineage, leukocyte lineage and thrombocyte lineage. A preferred BLAST cell population of the present invention includes cells capable of developing into primitive erythroid cells, definitive erythroid cells, macrophages, neutrophils, mast cells, T cells, endothelial cell, B cells, natural killer cells, megakaryocytes, eosinophils, and progenitors and progeny thereof. As used herein, a primitive erythroid cell is characterized by the cell's nucleated morphology and expression of embryonic globin. A definitive erythroid cell (also referred to as an adult erythroid cell) is characterized by the cell's expression of adult globin and eventual enucleation. As used herein, a "progenitor" cell refers to an ancestor of a cell (i.e. a cell from which a subject cell is derived). As used herein, a "progeny" cell refers to a cell derived from a subject cell.

A BLAST cell population of the present invention includes a colony of cells having substantially the same morphology as the colony of cells shown in FIG. 2, cell colony B. The BLAST cell population shown in FIG. 2, cell colony B was obtained when EB cells were grown as described in Example 3. Referring to FIG. 2, the BLAST cell population shown as cell colony B has a general morphology of clumped, but not tightly packed cells, in which individual cells can be discerned when the colony is viewed under the microscope.

A BLAST cell population of the present invention that has been derived by culturing a population of EB cells for 6 days (i.e. Day 6 BLASTS) can include cells that have substantially the same antibody staining pattern as shown in FIGS. 3A and 3B, when such BLAST cells are stained according to the method described in Example 4. Referring to FIGS. 3A and 3B, a Day 6 BLAST cell population expresses substantial amounts of CD44, C-kit receptor, Sca-1 and VLA-4, and essentially no Class I H-2b, Thy 1 and CD45.

Another aspect of the present invention is a method to produce a population of BLAST-LYM cells that are able to develop into a cell of lymphoid lineage, when cultured under appropriate conditions. In one embodiment, a BLAST-LYM cell population of the present invention can be derived by culturing a population of pluripotent BLAST cells of the present invention in a BLAST-LYM cell medium, which is medium that stimulates the differentiation of a BLAST cell population of the present invention to a BLAST-LYM cell population of the present invention. A BLAST-LYM cell medium of the present invention includes a suitable amount of one or more lymphoid cell growth factors that are capable of stimulating the differentiation of a BLAST cell population to an BLAST-LYM cell population. A preferred BLAST-LYM cell medium for the production of BLAST-LYM cells of the present invention includes one or more of the lymphoid growth factors IL-7, C-kit ligand, insulin-like growth factor 1 (IGF-1), VEGF, EPO, a growth factor produced by an embryoid body cell, homologues of such growth factors, or mixtures of such growth factors and/or homologues. A more preferred BLAST-LYM cell medium for the production of BLAST-LYM cells of the present invention includes one or more of the lymphoid growth factors, IL-7, C-kit ligand, insulin-like growth factor 1 (IGF-1), homologues of such growth factors, or mixtures of such growth factors and/or homologues.

According to the present invention, a BLAST-LYM cell medium of the present invention includes PP-FBS or pre-selected normal FCS as well as one or more suitable growth factor as described above. A preferred BLAST-LYM cell medium of the present invention includes from about 5% to about 30%, more preferably from about 7% to about 20%, and even more preferably about 10% PP-FBS or pre-selected normal FCS.

Also according to the present invention, a BLAST cell population of the present invention is preferably cultured in methyl cellulose to obtain a population of BLAST-LYM cells. A suitable amount of methyl cellulose for culturing 3LAST cell populations is an amount that enables the BLAST-LYM cells to associate as groups (i.e. clumps or clusters) of cells, thereby stimulating growth and/or differentiation of the BLAST cells into BLAST-LYM cells. A preferred amount of methyl cellulose in which to-culture a BLAST cell population of the present invention to obtain a BLAST-LYM is from about 0.25% to about 2.0%, more preferably from about 0.5% to about 1.5%, and even more preferably at about 1%.

A BLAST-LYM cell population of the present invention is derived by culturing a population of BLAST cells for a suitable amount of time to produce a BLAST-LYM cell population able to develop into a lymphoid lineage. In particular, the present invention includes a population of BLAST-LYM cells that are derived by culturing a population of BLAST cells for a suitable amount of time to produce a population of BLAST-LYM cells that are capable of developing into a T cell or a B cell when cultured under appropriate conditions. According to the present invention, a T cell includes a cell that represents a given stage of T cell maturation, and as such, can rearrange from immature T cells having rearranged T cell receptor germline genes to mature T cells expressing $\alpha\beta$ T cell receptor proteins. Also according to the present invention, a B cell can include a cell that represents a given stage of B cell maturation, and as such, can range from an early B cell having rearranged diversity (i.e. D) region and joining (i.e. J) region immunoglobulin germline genes, more preferably a cell having rearranged diversity D, J and variable (i.e. V) region immunoglobulin germline genes, to a plasma cell that is able to secrete immunoglobulin proteins. A BLAST-LYM cell population is derived by culturing a population of BLAST cells from about 3 day to about 10 days, preferably for about 6 days.

In accordance with the present invention, other culture conditions (i.e. in addition to time and medium) are also important in obtaining a BLAST-LYM cell population of the present invention from a population of BLAST cells. During culturing, variables such as cell density, temperature and $CO_2$ levels can be controlled to maximize the development of populations of BLAST-LYM cells. For example, it appears that the density of cells in a BLAST cell culture can affect the development of a BLAST-LYM cell population. The optimum cell density for the growth of an BLAST-LYM cell population is from about $5\times10^4$ BLAST cells per ml to about $7.5\times10^5$ BLAST cells per ml, more preferably from about $1\times10^5$ BLAST cells per ml to about $6\times10^5$ BLAST cells per ml, and even more preferably from about $2.5\times10^5$ BLAST cells per ml to about $5\times10^5$ BLAST cells per ml. The optimum temperature for the development of an BLAST-LYM cell population is from about 35° C. to about 39° C., preferably prom about 36° C. to 38° C., with a temperature of 37° C. being even more preferred. The optimum $CO_2$ levels in the culturing environment for the development of BLAST-LYM cell populations is from about 3% $CO_2$ to about 10% $CO_2$, more preferably from about 4% $CO_2$ to about 6% $CO_2$, and even more preferably about 5% $CO_2$.

In a preferred embodiment, a BLAST-LYM cell population of the present invention is derived by culturing an individual BLAST cell colony in a medium including IMDM, with about 10% PP-FBS, 1% methyl cellulose, and a mixture of growth factors including IL-7, IGF-1 and C-kit ligand for about 6 days at about 37° C., in an about 5% $CO_2$-containing environment to obtain a population of BLAST-LYM cells.

In accordance with the present invention, a BLAST-LYM cell population of the present invention includes cells of a lymphoid lineage. Preferred cells within a BLAST-LYM cell population of the present invention include cells of a T cell lineage, a B cell lineage, and/or a natural killer cell lineage. More preferred cells within a BLAST-LYM cell population of the present invention can develop into T cells having rearranged T cell receptor germline genes and B cells having rearranged D and J region immunoglobulin germline genes. Particularly preferred cells within a BLAST-LYM cell population of the present invention can develop into a T cell expressing T cell receptor proteins, such as $\alpha\beta$ and/or $\gamma\delta$ T cell receptors, or a B cell having rearranged V, D and J region immunoglobulin germline genes.

One aspect of the present invention is a method to produce a lymphoid cell population that includes the steps of: (a) culturing a BLAST cell population in an BLAST-LYM cell medium including one or more lymphoid cell growth factors to produce a BLAST-LYM cell population; and (b) culturing the BLAST-LYM cell population with cells selected from the group consisting of fetal thymi culture cells and bone marrow stromal cells to obtain a lymphoid cell population.

In one embodiment, a BLAST-LYM cell population of the present invention is cultured in a fetal thymi culture to obtain a population of T cells. Preferably, a BLAST cell population cultured in the presence of C-kit ligand, IGF-1 and IL-7 is used to produce a BLAST-LYM cell which is cultured in a fetal thymi culture to produce a T cell population. Techniques to perform fetal thymi cultures are well known to those of skill in the art. Preferably, a BLAST-LYM population is cultured in a fetal thymi culture for from about 1 week to about 6 weeks, more preferably for from about 1.5 weeks to about 4 weeks, and even more preferably for from about 2 weeks to about 3 weeks. A preferred T cell population of the present invention is a population of cells comprising from about 1% to about 75% T cells, more preferably from about 3% to about 65% T cells, and even more preferably from about 5% to about 50% T cells. It is within the scope of the invention, however, that a T cell population can also include other lymphocyte subpopulations that are typically found in a thymic population. For example, a T cell population of the present invention can include macrophages, dendritic cells, natural killer cells and epithelial cells. The T cells included in a T cell population of the present invention preferably include T cells having rearranged T cell receptor germline genes and more preferably include T cells expressing T cell receptor proteins, including $\alpha\beta$ and/or $\gamma\delta$ T cell receptors.

In another embodiment, a BLAST-LYM cell population of the present invention is cultured in the presence of bone marrow stromal cells to obtain a population of B cells. Preferably, a BLAST cell population cultured in the presence of C-kit ligand alone is used to produce a BLAST-LYM cell which is cultured with bone marrow stromal cells to produce a B cell population. Techniques to perform bone marrow stromal cell cultures are well known to those of skill in the art. Preferably, a BLAST-LYM population is cultured in the presence of bone marrow stromal cells for from about 3 days to about 75 days, more preferably for from about 7 days to about 45 days, and even more preferably for from about 14 days to about 21 days. A preferred B cell population of the present invention is a population of cells comprising from about 0.5% to about 20% B cells, more preferably from about 0.75% to about 17% B cells, and even more preferably from about 1% to about 15% B cells. A preferred B cell population includes B cells having rearranged D and J region immunoglobulin germline genes, and more preferably B cells having rearranged V, D and J region germline genes.

Another aspect of the present invention is a method to produce a population of BLAST-NEM cells that are able to develop into a cell of certain hematopoietic lineages when cultured under appropriate conditions. According to the present invention, a cell of hematopoietic lineage is able to develop into erythrocyte cells (i.e. a red blood cell), certain leukocyte cells (i.e. a white blood cell other than lymphocytes), or thrombocyte cells (i.e. platelet cell). Leukocyte cells include granular leukocytes, including eosinophils, basophils, neutrophils, and mast cells; as well as non-granular leukocytes, including megakaryocytes, polymorphonuclear cells, lymphocytes and monocytes (i.e.

macrophages). A BLAST-NEM cell population of the present invention comprises cells that are able to develop into any hematopoietic cell type other than lymphocytes. A preferred BLAST-NEM cell population of the present invention includes cells that are able to develop into erythrocytes, Leukocytes other than lymphocytes, or thrombocytes. A more preferred BLAST-NEM cell population of the present invention includes cells that are able to develop into primitive erythroid cells, definitive erythroid cells, macrophages, mast cells, neutrophils, eosinophils, megakaryocytes, undifferentiated hematopoietic cell colonies, or progenitors or progeny thereof. An even more preferred BLAST-NEM cell population of the present invention includes cells that are able to develop into primitive erythroid cells, definitive erythroid cells, macrophages, mast cells, neutrophils, or progenitors or progeny thereof.

In one embodiment, a BLAST-NEM cell population of the present invention can be derived by culturing a population of pluripotent BLAST cells of the present invention in a BLAST-NEM cell medium, which is a medium that stimulates the differentiation of a BLAST cell population of the present invention to a BLAST-NEM cell population of the present invention. An BLAST-NEM cell medium of the present invention includes a suitable amount of one or more BLAST-NEM cell growth factors that are capable of stimulating the differentiation of a BLAST cell population to an BLAST-NEM cell population. For purposes of this application, BLAST-NEM cell growth factors differ from hematopoietic growth factors in that hematopoietic growth factors of the present invention include lymphoid factors and the BLAST-NEM cell growth factors of the present invention do not. A preferred BLAST-NEM cell medium includes one or more of the BLAST-NEM cell growth factors C-kit ligand, IL-1, IL-3, IL-6, IL-11, VEGF, EPO, homologues of such growth factors, or mixtures of such growth factors and/or homologues. A more preferred BLAST-NEM cell medium includes C-kit ligand, IL-1, IL-3, IL-6, IL-11, VEGF and EPO.

According to the present invention, a BLAST-NEM cell medium of the present invention includes PP-FBS or preselected normal FCS as well as one or more suitable growth factor as described above. A preferred BLAST-NEM cell medium of the present invention includes from about 5% to about 30%, more preferably from about 7% to about 20%, and even more preferably about 10% PP-FBS or preselected normal FCS.

Also according to the present invention, a BLAST cell population of the present invention is preferably cultured in methyl cellulose to obtain a population of BLAST-NEM cells. A suitable amount of methyl cellulose for culturing BLAST cell populations is an amount that enables the BLAST-NEM cells to associate as groups (i.e. clumps or clusters) of cells, thereby stimulating growth and/or differentiation of the BLAST cells into BLAST-NEM cells. A preferred amount of methyl cellulose in which to culture a BLAST cell population of the present invention to obtain a BLAST-NEM is from about 0.25% to about 2.0%, more preferably from about 0.5% to about 1.5%, and even more preferably at about 1%.

A BLAST-NEM cell population of the present invention is derived by culturing a population of BLAST cells for a suitable amount of time to produce a BLAST-NEM cell population able to develop into a hematopoietic lineage. In particular, the present invention includes a population of BLAST-NEM cells that are derived by culturing a population of BLAST cells for a suitable amount of time to produce a population of BLAST-NEM cells that are capable of developing into erythrocyte or leukocyte cells. A BLAST-NEM cell population is derived by culturing a population of BLAST cells from about 2 days to about 12 days. A preferred BLAST-NEM cell population is derived by culturing a population of BLAST cells from about 4 days to about 8 days, with culturing for about 6 days being more preferred.

In accordance with the present invention, other culture conditions (i.e. in addition to time and medium) are also important in obtaining a BLAST-NEM cell population of the present invention from a population of BLAST cells. During culturing, variables such as cell density, temperature and $CO_2$ levels can be controlled to maximize the development of populations of BLAST-NEM cells. For example, it appears that the density of cells in a BLAST cell culture can affect the development of a BLAST-NEM cell population. The optimum cell density for the growth of an BLAST-NEM cell population is from about $5 \times 10^4$ BLAST cells per ml to about $7.5 \times 10^5$ BLAST cells per ml, more preferably from about $1 \times 10^5$ BLAST cells per ml to about $6 \times 10^5$ BLAST cells per ml, and even more preferably from about $2 \times 10^5$ BLAST cells per ml to about $5 \times 10^5$ BLAST cells per ml. The optimum temperature for the development of an BLAST-NEM cell population is from about 35° C. to about 39° C., preferably from about 36° C. to 38° C., with a temperature of 37° C. being even more preferred. The optimum $CO_2$ levels in the culturing environment for the development of BLAST-NEM cell populations is from about 3% $CO_2$ to about 10% $CO_2$, more preferably from about 4% $CO_2$ to about 6% $CO_2$, and even more preferably about 5% $CO_2$.

In a preferred embodiment, a BLAST-NEM cell population of the present invention is derived by culturing a population of BLAST cells in an embryoid body medium including IMDM, with about 10% PP-FBS, 1% methyl cellulose, and a mixture of growth factors including C-kit ligand, IL-1, IL-3, IL-6, IL-11, VEGF and EPO for about 6 days at about 37° C., in an about 5% $CO_2$-containing environment to obtain a population of BLAST-EM cells.

Another aspect of the present invention is a method to produce a population of leukocytes and erythrocytes that includes the steps of: (a) culturing a BLAST cell population in an BLAST-NEM cell medium including one or more BLAST-NEM cell growth factors to produce a BLAST-NEM cell population; and (b) culturing the BLAST-NEM cell population with one or more leukocyte and/or erythrocyte growth factors to obtain a mixed population of leukocyte and/or erythrocyte cells. Preferred leukocyte and/or erythrocyte growth factors useful for the production of a population of leukocytes and erythrocytes include one or more of the leukocyte and/or erythrocyte growth factors C-kit ligand, IL-1, IL-3, IL-6, IL-11, EPO, GM-CSF, G-CSF, M-CSF, homologues of such growth factors, or mixtures of such growth factors and/or homologues. More preferred leukocyte and/or erythrocyte growth factors include C-kit ligand, IL-1, IL-3, IL-6, IL-11, EPO, (.M-CSF, G-CSF and/or M-CSF.

A mixed population of leukocyte and/or erythrocyte cells is derived by culturing a population of BLAST-NEM cells from about 2 days to about 14 days. A preferred mixed population of leukocyte and/or erythrocyte cells is derived by culturing a population of BLAST-NEM cells from about 4 days to about 12 days, with culturing for about 8 days being more preferred.

According to the present invention, a BLAST-NEM cell medium of the present invention includes PP-FBS or preselected normal FCS as well as one or more suitable growth factor as described above. A preferred BLAST-NEM cell medium of the present invention includes from about 5% to about 30%, more preferably from about 7% to about 20%, and even more preferably about 10% PP-FBS or pre-selected normal FCS.

Also according to the present invention, a BLAST cell population of the present invention is cultured in methyl cellulose to obtain a population of BLAST-NEM cells. A suitable amount of methyl cellulose for culturing BLAST cell populations is an amount that enables the BLAST-NEM cells to associate as groups (i.e. clumps or clusters) of cells, thereby stimulating growth and/or differentiation of the BLAST cells into BLAST-NEM cells. A preferred amount of methyl cellulose in which to culture a BLAST cell population of the present invention to obtain a BLAST-NEM is from about 0.25% to about 2.0%, more preferably from about 0.5% to about 1.5%, and even more preferably at about 1%.

A BLAST-NEM cell population of the present invention is derived by culturing a population of BLAST cells for a suitable amount of time to produce a BLAST-NEM cell population able to develop into a hematopoietic lineage. In particular, the present invention includes a population of BLAST-NEM cells that are derived by culturing a population of BLAST cells for a suitable amount of time to produce a population of BLAST-NEM cells that are capable of developing into a primitive erythroid cell, a definitive erythroid cell, a macrophage, a neutrophil or a mast cell, when cultured under appropriate conditions. A BLAST-NEM cell population is derived by culturing a population of BLAST cells from about 3 day to about 10 days, preferably for about 6 days.

In accordance with the present invention, other culture conditions (i.e. in addition to time and medium) are also important in obtaining a BLAST-NEM cell population of the present invention from a population of BLAST cells. During culturing, variables such as cell density, temperature and $CO_2$ levels can be controlled to maximize the development of populations of BLAST-NEM cells. For example, it appears that the density of cells in a BLAST cell culture can affect the development of a BLAST-NEM cell population. The optimum cell density for the growth of an BLAST-NEM cell population is from about $5 \times 10^4$ BLAST cells per ml to about $7.5 \times 10^5$ BLAST cells per ml, more preferably from about $1 \times 10^5$ BLAST cells per ml to about $6 \times 10^5$ BLAST cells per ml, and even more preferably from about $2.5 \times 10^5$ BLAST cells per ml to about $5 \times 10^5$ BLAST cells per ml. The optimum temperature for the development of an BLAST-NEM cell population is from about 35° C. to about 39° C., preferably from about 36° C. to 38° C., with a temperature of 37° C. being even more preferred. The optimum $CO_2$ levels in the culturing environment for the development of BLAST-NEM cell populations is from about 3% $CO_2$ to about 10% $CO_2$, more preferably from about 4% $CO_2$ to about 6% $CO_2$, and even more preferably about 5% $CO_2$.

In a preferred embodiment, a BLAST-NEM cell population of the present invention is derived by culturing an individual BLAST cell colony in a medium including IMDM, with about 10% PP-FBS, 1% methyl cellulose, and a mixture of growth factors including IL-1, IL-3, IL-6, IL-11, C-kit ligand and EPO for about 6 days at about 37° C., in an about 5% $CO_2$-containing environment to obtain a population of BLAST-NEM cells.

Another aspect of the present invention is a method to produce an immortalized precursor cell population by (a) transforming an embryonic stem cell population of the present invention with an immortalizing gene to create a transformed stem cell population; (b) culturing the transformed stem cell population under effective conditions to produce a transformed embryoid body cell population; and (c) incubating the transformed embryoid body cell population under conditions suitable to obtain an immortalized precursor cell population.

Methods for transformation and expression of immortalizing genes in an embryonic cell population of the present invention are standard to those in the art (see, for example, Sambrook et al., ibid.). A preferred immortalizing gene of the present invention includes a gene that encodes a protein that is capable of altering an embryonic cell of the present invention in such a manner that the cell can survive under appropriate culture conditions for at least about 1 month, preferably about 6 months and even more preferably about 12 months. A preferred immortalizing gene of the present invention is a HOX11 gene. A more preferred immortalizing gene is a human HOX11 gene (described in detail in Lu et al., *EMBO J*. 10:2905–2910, 1991).

Preferably, a HOX11 gene of the present invention is operatively linked to an expression vector to from a recombinant molecule. The phrase "operatively linked" refers to insertion of a nucleic acid molecule (e.g., a gene) into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e. direct gene expression) in embryonic cells of the present invention. Preferred expression vectors of the present invention can direct gene expression in mammalian cells and more preferably in the cell types heretofore disclosed. Preferred expression vectors of the present invention include, for example, MSCV and MESV (described in Grez et al., *Proc. Natl. Acad. Sci. USA* 87:920.2–9206, 1990), with MSCVv2.1 retroviral expression vector being particularly preferred.

A preferred recombinant molecule of the present invention comprises an MSCV-HOX11 plasmid (described in detail in Example 13).

According to the present invention, an effective condition to produce a transformed embryoid body cell population of the present invention includes those conditions disclosed herein that are suitable for the development of an EB cell population. Preferably, a transformed embryonic stem cell population of the present invention is cultured for about 12 days, more preferably for about 8 days and even more preferably for about 7 days.

Preferred conditions suitable to produce an immortalized precursor cell population of the present invention include suitable culture medium (referred to herein as IPC medium) and culture times. A preferred IPC medium of the present invention includes at least one growth factor as disclosed herein. A more preferred IPC medium of the present invention includes IL-3, IL-4, IL-6, IL-11, EPO, C-kit ligand, LIF, or mixtures of such growth factors and/or homologues of such growth factors. An even more preferred IPC medium of the present invention includes a mixture of IL-3 and EPO, C-kit ligand combined with EPO and/or homologues thereof.

In accordance with the present invention, an IPC medium includes PP-FBS or pre-selected normal FCS, in addition to one or more growth factors described above. A preferred concentration of PP-FBS or pre-selected normal FCS to include in an IPC medium of the present invention includes from about 10% and about 25%, more preferably from about 12% to about 20%, and even more preferably about 15% PP-FBS or pre-selected normal FCS.

Also according to the present invention, a transformed EB cell population of the present invention is cultured in liquid culture to obtain a population of immortalized precursor cells of the present invention.

A population of immortalized precursor cells of the present invention is derived by culturing a population of transformed EB cells at a suitable cell density to produce a precursor population of immortalized cells. The optimum cell density for the growth of a transformed EB cell population is preferably from about $1 \times 10^5$ cells to about $7 \times 10^5$ transformed EB cells, more preferably from about $2 \times 10^5$ cells to about $6 \times 10^5$ transformed EB cells, and even more preferably about $5 \times 10^5$ transformed EB cells per ml of culture medium.

Applicants have discovered that culturing of a transformed EB cell population for a certain period of time in accordance with the present invention results in the formation of a precursor population of immortalized cells of the present invention. Preferably, a precursor population of immortalized cells is derived by culturing a population of transformed EB cells from at least about 1 days to about 28 days, more preferably from at least about 2 days to about 14 days and even more preferably from about 3 days to about 8 days.

Other culture conditions (i.e. in addition to time and medium) which can effect the development of a precursor population of immortalized cells of the present invention include the temperature and $CO_2$ content of the culture environment as disclosed in detail herein.

In a preferred embodiment, a precursor population of immortalized cells of the present invention is derived by culturing a population of transformed EB cells of the present invention in an IPC medium including IMDM, with about 10% pre-selected normal FCS, 1% methyl cellulose, and either a mixture of growth factors including IL-3 and EPO or C-kit ligand and EPO. The transformed EB cell population is grown at a cell density of from about $2 \times 10^5$ cells per ml of medium to about $5 \times 10^5$ cells per ml of medium. After reaching that density, the transformed EB cell population is then cultured for from about 70 to about 100 days, at about 37° C., in an about 5% $CO_2$-containing environment to obtain a population of immortalized precursor cells.

An immortalized precursor cell population of the present invention includes cells of mesodermal cell lineage. In particular, an immortalized precursor cell population of the present invention includes cells of hematopoietic lineage, endothelial lineage, epithelial lineage, muscle cell lineage and neural cell lineage. A preferred immortalized precursor cell population of the present invention includes cells capable of developing into erythroid cells, endothelial cell and leukocyte lineage, and progenitors and progeny thereof.

According to the present invention, a precursor cell population of the present invention is immortalized using a HOX11 gene. Such immortalized cell populations are referred to herein as HOX11 precursor cell populations. In one embodiment, HOX11 precursor cell populations of the present invention include: (1) a population of cells comprising cells having a cell surface molecule FcγRII, FcγRIII, Thy-1, CD44, VLA-4α, LFA-1β or combinations thereof; (2) a population of cells comprising cells having a cell surface molecule FcγRII, FcγRIII, CD44, VLA-4α, LFA-1β or combinations thereof; (3) a population of cells comprising cells having a cell surface molecule HSA, CD44, VLA-4α, LFA-1β, ICAM-1 or combinations thereof; (4) a population of cells comprising cells having a cell surface molecule CD45, Aa4.1, Sca-1, HSA, FcγRII, FcγRIII, Thy-1, Mac-1, Gr-1, CD44, VLA-4α, LFA-1β or combinations thereof; or (5) a population of cells comprising cells having a cell surface molecule CD45, Aa4.1, HSA, FcγRII, FcγRIII, Thy-1, Mac-1, Gr-1, CD44, VLA-4α, LFA-1β, ICAM-1 or combinations thereof. According to the present invention, the cells of group (1), (4) and (5) can either express or not express the cell surface marker TER119. In addition, the cells of group (2) can either express or not express the cell surface marker Thy-1.

In another embodiment, a HOX11 precursor cell population of the present invention comprises: (1) a population of cells that is responsive to a growth factor selected from the group consisting of IL-3, IL-4, IL-6, IL-11, EPO, C-kit ligand, LIF or mixtures thereof; (2) a population of cells that is responsive to a growth factor selected from the group consisting of IL-3, EPO, C-kit ligand, LIF or mixtures thereof; or (3) a population of cells that is responsive to a growth factor selected from the group consisting of IL-3, EPO, granulocyte macrophage colony stimulating factor (GM-CSF) or mixtures thereof.

Particularly preferred HOX11 precursor cell populations of the present invention comprise: (1) a population of cells that comprise a cell surface molecule selected from the group consisting of FcγRII, FcγRIII, Thy-f, CD44, VLA-4α, LFA-1β or combinations thereof, and are responsive to a growth factor selected from the group consisting of IL-3, IL-4, IL-6, IL-11, EPO, C-kit ligand, LIF or mixtures thereof; (2) a population of cells that comprise a cell surface molecule selected from the group consisting of HSA, CD44, VLA-4α, LFA-1β, ICAM-1 or combinations thereof, and are responsive to a growth factor selected from the group consisting of IL-3, EPO, C-kit ligand, LIF or mixtures thereof; and (3) a population of cells that comprise a cell surface molecule selected from the group consisting of CD45, Aa4.1, Sca-1, HSA, FcγRII, FcγRIII, Thy-1, Mac-1, Gr-1, CD44, VLA-4α, LFA-1β or combinations thereof, and are responsive to a growth factor selected from the group consisting of IL-3, EPO, GM-CSF or mixtures thereof.

In another embodiment, a HOX11 precursor cell population of the present invention comprises a population of cells that express RNA transcribed from the βH1, zeta (ζ) and β major globin genes.

In a preferred embodiment, a precursor cell population of the present invention comprises: (1) a population of cells, referred to herein as Embryoid Body HOX11 Cell Line-1 (EBHX-1), that comprises a cell surface molecule selected from the group consisting of FcγRII, FcγRIII, Thy-1, CD44, VLA-4α, LFA-1β or combinations thereof, that is responsive to a growth factor selected from the group consisting of IL-3, IL-4, IL-6, IL-11, EPO, C-kit ligand, LIF or mixtures thereof, and that expresses RNA transcribed from the βH1, ζ and β major globin genes; (2) a population of cells, referred to herein as Embryoid Body HOX11 Cell Line-4 (EBHX-4), that comprises a cell surface molecule selected from the group consisting of FcγRII, FcγRIII, CD44, VLA-4α, LFA-1β or combinations thereof; (3) a population of cells, referred to herein as Embryoid Body HOX11 Cell Line-11 (EBHX-11), that comprises a cell surface molecule selected from the group consisting of HSA, CD44, VLA-4α, LFA-1β, ICAM-1 or combinations thereof, that is responsive to a growth factor selected from the group consisting of IL-3, EPO, C-kit ligand, LIF or mixtures thereof, and that expresses RNA transcribed from the βH1, ζ and β major globin genes; (4) a population of cells, referred to herein as Embryoid Body HOX11 Cell Line-14 (EBHX-14), that comprises a cell surface molecule selected from the group consisting of CD45, Aa4.1, Sca-1, HSA, FcγRII, FcγRIII, Thy-1, Mac-1, Gr-1, CD44, VLA-4α, LFA-1β or combinations thereof, that is responsive to a growth factor selected from the group consisting of IL-3, EPO, GM-CSF or mixtures thereof; and (5) a population of cells, referred to herein as Embryoid Body HOX11 Cell Line-15 (EBHX-15), that comprises a cell surface molecule selected from the group consisting of CD45, Aa4.1, HSA, FcγRII, FcγRIII, Thy-1, Mac-1, Gr-1, CD44, VLA-4α, LFA-1β, ICAM-1 or combinations thereof.

In another preferred embodiment, a precursor cell population of the present invention comprises populations of cells referred to herein as Embryoid Body HOX11 Cell Line-2 (EBHX-2), Embryoid Body HOX11 Cell Line-3 (EBHX-3), Embryoid Body HOX11 Cell Line-5 (EBHX-5), Embryoid Body HOX11 Cell Line-6 (EBHX-6), Embryoid Body HOX11 Cell Line-7 (EBHX-7), Embryoid Body HOX11 Cell Line-8 (EBHX-8), Embryoid Body HOX11 Cell Line-9 (EBHX-9), Embryoid Body HOX11 Cell Line-10 (EBHX-10), Embryoid Body HOX11 Cell Line-12 (EBHX-12), and Embryoid Body HOX11 Cell Line-13 (EBHX-13), the production of which are described in Example 14.

According to the present invention, a population of immortalized precursor cells is preferably at least about 70% clonal, more preferably at least about 80% clonal and even more preferably at least about 90% clonal. As used herein, the term "clonal" refers to a group of cells that are of a single cell type (e.g., that all express the same surface markers or display essentially the same responsiveness to a growth factor).

The pluripotent and/or precursor cell populations of the present invention can be used in the isolation and evaluation of compounds associated with the differentiation of embryonic cells. Thus, another aspect of the present invention is a method to identify a compound expressed during the development of a population of embryonic stem cells which, as used herein, is a compound expressed during the development of a population of BLAST cells of the present invention from an ES cell population (i.e. including the stage of EB cell development) in transformed or non-transformed cells. The method comprises characterizing at least a portion of the cellular composition of at least one cell contained in a population of cells including an ES cell population, a pluripotent EB cell population of the present invention, a HOX11 precursor cell population, a pluripotent embryonic blast cell population and intermediates thereof (i.e. cells of stages between ES and EB cell populations, or between EB and BLAST cell populations), to identify a compound expressed during the development of a population of embryonic stem cells. As used herein, a cellular composition refers a composition containing components of a cell. Preferred cellular compositions of the present invention include nucleic acids, proteins, lipids (including membranes) and/or carbohydrates, with proteins, DNA molecules and RNA molecules being more preferred. Preferred cells from which to identify compounds includes, for example, EBHX-1, EBHX-2, EBHX-3, EBHX-4, EBHX-5, EBHX-6, EBHX-7, EBHX-8, EBHX-9, EBHX-10, EBHX-11, EBHX-12, EBHX-13, EBHX-14 and EBHX-15 (the group of which are referred to herein as EBHX-1 through EBHX-15).

The present invention includes a variety of methods to identify an embryonic cell compound using an embryonic cell population of the present invention. In one embodiment, an embryonic cell compound of the present invention is identified by direct hybridization studies, comprising hybridizing a nucleic acid molecule probe (which can be DNA, RNA or modified forms thereof) to a composition of nucleic acid molecules isolated from an embryonic cell population of the present invention. Such a method is useful for identifying the expression of compounds in an embryonic cell population. For example, a nucleic acid molecule encoding a protein can be hybridized under suitable conditions known to those of skill on the art (see, for example, Sambrook et al., *Molecular Cloning: A Laboratory Manual*, Cold Spring Harbor Labs Press, 1989) to an RNA composition isolated from an embryonic cell population of the present invention, or to a cDNA product thereof. Preferred nucleic acid molecules for use in a direct hybridization study of the present invention include nucleic acid molecules that encode marker proteins including, but not limited to, endothelial cell proteins, lymphoid cell proteins, epithelial proteins, mature hematopoietic cell proteins, and/or hematopoietic stem cell proteins. As used herein, a marker protein is a protein typically found in certain cell types and, as such, can suggest identification of such cell type. Particularly preferred nucleic acid molecules for use in a direct hybridization study of the present invention include nucleic acid molecules that encode proteins including stem cell leukemia protein, GATA-1, GATA-2, C-Myb, C-kit ligand, C-fms, Flk-1, X protein (encoded by a c globin gene), β major globin protein, ζ protein (encoded by a βH1-globin gene), Y protein (encoded by an εY gene), brachyury, VLA-4 and LFA-1. An embryonic cell-derived nucleic acid composition useful for such direct hybridization studies can include genomic DNA, RNA or cDNA of such RNA.

In another embodiment, an embryonic cell compound of the present invention is identified by selective nucleic acid hybridization techniques well known to those of skill in the art. Such subtractive hybridization techniques are particularly useful for identifying novel embryonic cell compounds and for identifying compounds expressed in a given cell type. Subtractive hybridization techniques of the present invention can be performed by, for example: (1) hybridizing nucleic acid molecules isolated or derived from an embryonic cell population of the present invention to nucleic acid molecules isolated or derived from a non-embryonic cell population; or (2) hybridizing nucleic acid molecules isolated or derived from a first embryonic cell population of the present invention to nucleic acid molecules isolated or derived from a second embryonic cell population of the present invention. For example, nucleic acid molecules isolated from an EB cell population of the present invention can be subtracted from nucleic acid molecules isolated or derived from a BLAST cell population of the present invention or vice versa.

In yet another embodiment, an embryonic cell compound of the present invention is identified by nucleotide sequencing of DNA isolated from an embryonic cell population of the present invention. In order to identify compounds expressed in certain cell types, cDNA copies of poly A+ RNA is preferably analyzed. Identification of embryonic cell compounds can be achieved by comparing the DNA sequence information encoding such compounds derived from the embryonic cell population with sequences of known molecules. Such DNA sequencing studies are particularly useful for identifying novel embryonic cell compounds. DNA sequencing studies can be performed using techniques standard in the art (see, for example, Sambrook et al., ibid.).

In yet another embodiment, an embryonic cell compound of the present invention is identified by selective binding of proteins isolated from an embryonic cell population of the present invention to antibodies specific for known cellular proteins to determine the presence of such cellular proteins in the embryonic cell population. Such antibody binding studies are particularly useful for identifying the expression of known compounds by embryonic cell populations of the present invention. Antibody binding studies of the present invention can be performed using techniques standard in the art, such as by immunoblot assays, immunoprecipitation assays, enzyme immunoassays (e.g., ELISA), radioimmunoassays, immunofluorescent antibody assays and immunoelectron microscopy; see, for example, Sambrook et al., ibid.

In yet another embodiment, an embryonic cell compound of the present invention is identified by cell culture assays that indicate cell survival and cell proliferation. Such cell culture assays are particularly useful for identifying both novel and known growth factors that are secreted by an embryonic cell population of the present invention. A cell culture assay of the present invention can be performed by: (1) recovering supernatant from a culture of a dense embryonic cell population of the present invention; (2) contacting the supernatant with a sparse population of the embryonic cell population; and (3) determining if the supernatant is able to promote the survival and/or proliferation of said embryonic cell population by observing the health of said cell population. Such cell culture assays can be performed using the cell culturing techniques disclosed in detail herein. A preferred dense population of cells includes any cell density used to culture an embryonic cell population as disclosed herein. A preferred sparse population of an embryonic cell population of the present invention includes a cell density of from about $5\times10^3$ to about $2\times10^5$ cells per ml.

In yet another embodiment, an embryonic cell compound of the present invention involved in signal transduction in an embryonic cell is identified using kinase assays that are standard in the art. Such kinase assays are particularly useful for identifying known signal transduction proteins in an embryonic cell population of the present invention.

In yet another embodiment, an embryonic cell compound of the present invention is identified by protein:protein binding studies other than antibody binding studies. In particular, embryonic cell compounds are identified by determining ligand:receptor interactions. For example, an embryonic cell population of the present invention can be contacted with a known ligand to determine if the cell population contains cells having the receptor to which the ligand can bind. Such protein:protein binding studies can be performed using techniques known to those of skill in the art.

According to the present invention, an embryonic cell compound can be a compound that has been previously identified, or not previously identified, from a cell or culture medium of a cell other than a population of cells of the present invention. For example, an embryonic cell compound of the present invention can include a growth factor that is also produced by a more mature fetal or adult cell of an animal.

An embryonic cell compound of the present invention can be a compound that is capable of having a biological effect on a cell. For example, preferred embryonic cell compounds are capable of maintaining the survival of a cell, inducing the propagation of a cell and/or stimulating the differentiation of a cell. Preferred embryonic compounds of the present invention include a compound that can be used as a marker for a population of embryonic cells. In particular, an embryonic cell marker of the present invention can be cell surface markers, secreted molecules, cytoplasmic signal transduction molecules, transcription factors and other DNA or RNA binding proteins. As used herein, a cell surface marker refers to any compound on the surface of a cell that is detectable by techniques such as antibody binding studies, gel electrophoresis and various chromatography techniques known to those of skill in the art. A cell surface marker can include cell surface receptors, adhesion proteins, cell surface carbohydrate moieties, membrane-bound ligands and other molecules involved in cell to cell communication. A secreted molecule refers to any molecule produced and secreted by a cell into an extracellular environment and includes growth factors and other ligands. A cytoplasmic signal transduction molecule refers to a molecule that is able to regulate an intracellular chemical reaction that enables a cell to modify its biological functions based on signals in the environment, either outside or inside the cell. Signal transduction molecules can include enzymes, such as kinases, phosphatases and phospholipases. Preferred embryonic cell compounds of the present invention include a cell surface receptor, a cell surface molecule, a cytoplasmic signal transduction protein, a transcription factor, a growth factor, and DNA or RNA binding proteins.

Identification of known and novel (i.e. newly identified) compounds in an embryonic cell population of the present invention is particularly useful for defining markers useful for the identification and/or isolation of comparable populations of cells from non-embryonic populations of cells. A particularly preferred non-embryonic cell population to look for cells having embryonic markers includes non-embryonic cell populations, including bone marrow (e.g., fetal, infant, adolescent and adult bone marrow). The presence of an embryonic cell marker of the present invention on a non-embryonic cell can indicate that the non-embryonic cell is pluripotent. Preferred embryonic cell population markers to identify comparable non-embryonic cell populations include lineage-specific markers, such as hematopoietic precursor markers, in particular pre-hematopoietic mesoderm markers. In a preferred embodiment, a population of adult bone marrow cells is screened for the presence of a cell surface marker found on the surface of an EB cell population and/or a BLAST cell population of the present invention.

One embodiment of the present invention is a formulation that contains one or more isolated embryonic cell compounds of the present invention that can be used for therapeutic or experimental use. According to the present invention, an isolated embryonic cell compound is a compound that has been removed from its natural milieu. An isolated embryonic cell compound can, for example, be obtained from its natural source, be produced using recombinant DNA technology, or be synthesized chemically. Preferred embryonic cell compounds of the present invention, including homologues thereof, are capable of regulating embryonic development. A preferred embryonic cell compound homologue includes at least one epitope capable of effecting differentiation of an ES cell population. The ability of an embryonic cell compound homologue to effect differentiation of an ES cell population can be tested using techniques disclosed herein. A preferred formulation of the present invention includes at least one protein secreted by a cell contained in an EB cell population of the present invention and/or a BLAST cell population of the present invention. Preferably, a formulation of the present invention comprises a culture supernatant obtained by culturing an EB cell and/or BLAST cell population of the present invention.

Another aspect of the present invention comprises an antibody capable of binding to a cell compound of a cell population of the present invention. Binding can be measured using a variety of methods known to those skilled in the art including immunoblot assays, immunoprecipitation assays, enzyme immunoassays (e.g., ELISA), radioimmunoassays, immunofluorescent antibody assays and immunoelectron microscopy; see, for example, Sambrook et al., ibid. Antibodies of the present invention can be either polyclonal or monoclonal antibodies. Antibodies of the present invention include functional equivalents such as antibody fragments and genetically-engineered antibodies, including single chain antibodies, that are capable of selectively binding to at least one of the epitopes of the protein or mimetope used to obtain the antibodies. Preferred antibodies are raised in response to surface marker proteins of an embryonic cell population of the present invention, in particular, surface cell receptors. Antibodies of the present invention can be produced using methods standard in the art. Antibodies of the present invention are particularly useful for identifying and isolating populations of cells having such surface markers, in particular, populations of embryonic cells from different species of animals and/or cells with similar markers from adult bone marrow. Thus, particularly preferred antibodies of the present invention include antibodies that are capable of binding to cellular markers that delineate between different embryonic cell populations of the present invention.

One embodiment of the present invention includes a method to produce an antibody, comprising administering to an animal an effective amount of a protein derived from a HOX11 precursor cell population of the present invention and recovering an antibody capable of selectively binding to such protein. According to the present invention, a protein derived from a HOX11 precursor cell population can include an isolated protein or a protein that is associated with a HOX11 precursor cell population. An isolated protein useful for producing antibodies can include the full length protein, as well as fragments thereof, in particular, peptides. Such fragments can be selected by those of skill in the art based upon the antigenicity (i.e. ability to induce an antibody response in an animal) of a particular fragment. The antigenicity of a fragment can be determined by trial and error without experimentation, or by computer analysis using standard programs.

A preferred method to produce antibodies of the present invention includes (a) administering to an animal an effective amount of a protein isolated from a HOX11 precursor cell population of the present invention to produce the antibodies and (b) recovering the antibodies. Another preferred method to produce antibodies of the present invention includes (a) administering to an animal an effective number of cells from a HOX11 precursor cell population of the present invention to produce the antibodies and (b) recovering the antibodies. A preferred cell population for use with the present method includes EBHX-1 through EBHX-15, and/or derivatives thereof.

Another aspect of the present invention is a therapeutic composition that comprises a cell population of the present invention, which is capable of serving as a population of cells that act as progenitors of various lineages. The therapeutic composition can be particularly useful to repopulate one or more lineages in an animal. As used herein, the term repopulate refers to a cell population that can be administered to an animal to restore a lineage of cells. A therapeutic composition of the present invention can be useful for the treatment of disease, such as anemia, leukemia, breast cancer and other solid tumors, and AIDS. A therapeutic composition of the present invention can be particularly useful for enhancing populations of adult bone marrow cells used in transplantation procedures. A preferred therapeutic composition of the present invention includes a population of EB cells of the present invention, a population of immortalized precursor cells of the present invention and/or a population of BLAST cells of the present invention. A more preferred therapeutic composition of the present invention includes a population of EB cells of the present invention, a population of immortalized precursor cells of the present invention or derivatives (i.e., any cell that is derived from an immortalized precursor cell population) thereof and/or a population of BLAST cells of the present invention derived from an ES cell population derived from a mammalian embryo. An even more preferred therapeutic composition of the present invention includes a population of EB cells of the present invention, a population of BLAST cells of the present invention derived from an ES cell population derived from a human embryo, and/or EBHX-1 through EBHX-15 and/or derivatives thereof.

In one embodiment, the present invention includes a method to repopulate a hematopoietic cell population in an animal, comprising administering to an animal a suitable number of cells of a HOX11 pluripotent cell population of the present invention. A suitable number of cells includes a number needed to, for example, repopulate a lymphocyte population in a subjected being treated for a lymphoma. For example, subjects having a lymphoma can receive large doses of chemotherapy and radiotherapy to destroy cancerous lymphocyte cells. The lymphocyte populations in these subjects can be repopulated by administering to the subject a suitable number of cells from a cell population of the present invention, such that the lymphocyte count of the subject returns substantially back to normal. Preferably, a HOX11 pluripotent cell population for use with the present method includes EBHX-1, EBHX-4, EBHX-11, EBHX-14 and/or EBHX-15 cells or derivatives thereof.

Therapeutic compositions of the present invention can be administered to any animal, preferably to mammals, and more preferably to humans. Therapeutic compositions of the present invention can be formulated in an excipient that the animal to be treated can tolerate and that maintains the integrity of the embryonic cell population. Examples of such excipients include aqueous physiologically balanced salt solutions. Excipients can also contain minor amounts of additives, such as substances that enhance isotonicity and chemical stability.

One embodiment of the present invention includes a method to identify a regulatory factor that influences the growth of a cell, comprising: (1) contacting a HOX11 precursor cell population of the present invention with a regulatory factor including a putative regulatory factor, a known regulatory factor and mixtures thereof; and (2) assessing the responsiveness of the precursor cell population to the regulatory factor. Such method is particularly useful for identifying factors useful as therapeutic reagents to treat hematopoietic disorders. As used herein, the term "putative" refers to compounds having an unknown or previously unappreciated Regulatory activity in a particular process. A putative compound can be a protein-based compound, a carbohydrate-based compound, a lipid-based compound, a nucleic acid-based compound, a naturals organic compound, a synthetically derived organic compound, an anti-idiotypic antibody and/or catalytic antibody, or fragments thereof. A putative regulatory compound can be obtained, for example, from libraries of natural or synthetic compounds, in particular from chemical or combinatorial libraries (i.e., libraries of compounds that differ in sequence or size but that have the same building blocks; see for example, U.S. Pat. Nos. 5,010,175 and 5,266,684 of Rutter and Santi, which are incorporated herein by reference in their entirety) or by rational drug design.

In a rational drug design procedure, the three-dimensional structure of a compound, such as a cell surface marker, can be analyzed by, for example, nuclear magnetic resonance (NMR) or x-ray crystallography. This three-dimensional structure can then be used to predict structures of potential compounds, such as putative regulatory compounds by, for example, computer modelling. The predicted compound structure can then be produced by, for example, chemical synthesis, recombinant DNA technology, or by isolating a similar molecule from a natural source (e.g., plants, animals, bacteria and fungi). Potential regulatory compounds can also be identified using SELEX technology as described in, for example, PCT Publication Nos. WO 91/19813; WO 92/02536 and WO 93/03172 (which are incorporated herein by reference in their entirety).

One embodiment of a putative regulatory reagent includes a neutralizing reagent capable of blocking the activity of a protein that controls cell responsiveness (i.e., growth and/or differentiation) to a compound, such as a growth factor. The present invention includes a method to identify a neutralizing reagent, comprising: (1) contacting a HOX11 precursor cell population of the present invention with a known regulatory factor to produce a controlled cell population; (2) combining the controlled cell population with a neutralizing reagent including a known neutralizing compound of the regulatory factor or a putative neutralizing compound of the regulatory factor; and (3) assessing the responsiveness of the precursor cell population to the neutralizing compound.

According to the present method, the step of assessment can be performed using any one of a variety of methods known to those of skill in the art. In particular, the assessment step can be performed using a proliferation assay and/or a differentiation assay. A preferred proliferation assay of the present invention comprises standard assays that determine cell count number, thymidine uptake by a cell and enzyme activity, including enzyme-linked immunoassays and cellular enzyme assays. A preferred differentiation assay of the present invention comprises a standard method including: (a) determining globin gene expression; (b) identifying cell surface markers; (c) determining responsiveness to a growth factor; (d) observing alterations in morphology; and (e) determining expression of genes associated with differentiation of hematopoietic cells.

Another aspect of the present invention is the use of a cell population of the present invention for the treatment of genetic diseases. Genetic diseases associated with various lineages can be treated by genetic modification of autologous or allogenic populations of embryonic cells of the present invention. For example, diseases such as beta-thalassemia, sickle cell anemia, adenosine deaminase deficiency and other genetic diseases related to a deficiency or malfunction of a cell of hematopoietic lineage, can be corrected by introduction of a wild type gene into the embryonic cell population. Diseases other than those associated with hematopoietic cells can be treated, where the disease is related to the lack of a particular secreted product, such as a hormone, enzyme, growth factor and the like. Specific promoters can be employed based upon identification of transcription factors of an embryonic cell population as described herein. Thus, inducible production of a desired product encoded by transformed genes can be achieved.

Methods for transformation and expression of genes in an embryonic cell population of the present invention are standard to those in the art (see, for example, Sambrook et al., ibid.).

In accordance with the present invention, a nucleic acid molecule can be transformed into an embryonic cell population of the present invention to inhibit particular gene products, thereby inhibiting susceptibility to a disease. For example, an embryonic cell population of the present invention can be transformed with a ribozyme, or a nucleic acid molecule that is capable of homologous recombination or antisense expression. For example, a BLAST cell population of the present invention can be transformed with a gene that disrupts the expression of a specific T cell receptor gene and administered to an animal. Subsequent differentiation of the BLAST cell population to a T cell population results in the production of a population of T cell receptor negative T cells. Such a method could be effective for preventing or treating autoimmune disease which involve autoreactive T cell activity. Similarly, an embryonic cell population of the present invention can be modified to introduce an antisense sequence or ribozyme to prevent proliferation of any pathogen that uses proteins of an animal cell to proliferate (e.g., viruses) in an embryonic cell population, or in progenitors or progeny thereof.

The following experimental results are provided for purposes of illustration and are not intended to limit the scope of the invention.

EXAMPLES

Example 1

This example describes the production of a population of embryoid body cells from an embryonic stem cell population.

The CCE ES cell line, originally derived from a 129/Sv/Ev strain of mouse, were maintained in Dulbecco's modified Eagles medium (DMEM) supplemented with 15% fetal calf serum (FCS), $1.5 \times 10^{-4}$ M monothioglycerol (MTG), and Leukemia Inhibitory Factor (LIF). The Ed cells were passaged every 2–3 days at a dilution of approximately 1:15. Two days before the initiation of the differentiation cultures, the undifferentiated ES cells were passaged into Iscove's; modified Dulbecco's medium (IMDM) supplemented with the above components. To induce differentiation into an EB population of cells, the ES cells were trypsinized, washed, and counted using techniques standard in the art. The freshly dissociated ES cells were then cultured in IMDM containing 15% platelet-derived fetal bovine serum (PDS; obtained from Antech, TEXAS; also referred to herein as platelet-poor fetal bovine serum, PP-FBS), $4.5 \times 10^{-4}$ M MTG, transferrin (300 μg), glutamine (2 mM). The ES cells were plated in a final volume of 10 ml at a concentration of about 3000 to about 4500 cells per ml of medium in 150 mm bacterial grade dishes. The ES cell population was then cultured in a humidified environment of 5% $CO_2$, at a temperature of 37° C. At an appropriate time after the initiation of differentiation (i.e., plating of cells in PP-FBS), EB cell populations were harvested using standard techniques. The cells were then centrifuged at ×1000 rpm to pellet the cells and the supernatant was removed. The EB cells were resuspended in 3 ml trypsin for 1 to 3 minutes at 37° C. An equal volume of IMDM containing 5 to 10% FCS was added to the trypsinized cells. A single cell suspension of EB cells was achieved by passing the EB cells 3 to 4 times through a 3 ml or 5 ml syringe with a 20 gauge needle.

The EB cell colonies were viewed under a Leitz inverted light microscope and were found to generally consist of groups of tightly packed cells, in which individual cells were not easily detectable. A representative microscopic view of an EB cell colony is shown in FIG. 2, cell colony A. The EB cell colony consisted of a tightly packed group of cells, in which single cells were essentially not discernable.

Example 2

This example describes the labelling of a population of EB cells using antibodies specific for known cell surface molecules.

EB cells derived from ES cells that had been incubated for about 4 days (Day 4 EB) according to the method described in Example 1 were labelled for fluorescence activated cell sorter analysis using a panel of antibodies against a number of different surface markers. These included antibodies specific for AA4.1, Sca-1, C-kit receptor, H-2b, VLA-4, CD44, CD45 and Thy 1. In addition, a population of CCE ES cells, similar to those cells used to derive the EB cell population, were stained under the same conditions as the EB cell population as a control sample. The results are shown in FIGS. 3A and 3B. Referring to FIGS. 3A and 3B, the Day 4 EB cells (d4 EB) stained with low amounts of anti-Sca-1, anti-C-kit receptor and anti-H-2b antibodies, and essentially no anti-Thy 1, anti-VLA-4, anti-CD44 and anti-CD45 antibodies, thereby indicating low or no expression of the corresponding surface marker protein. In addition, comparing the staining pattern of the EB calls to the control ES cells, the EB cells express slightly higher levels of C-kit receptor and H-2b protein but slightly less Sca-1 protein. Thus, the results show that expression of certain surface antigens change over a period of 4 days during development of ES cells to EB cells.

Example 3

This example describes the production of a population of embryonic blast cells from an embryoid body cell population.

EB cells were generated as described in Example 1. A series of cultures were prepared by plating about $2 \times 10^5$ to about $5 \times 10^5$ EB cells, derived according to the method described in Example 1. The EB cells were cultured in 1% methyl cellulose made in IMDM containing 10% PP-FBS, transferrin (300 µg/ml), glutamine (2 mM), and either a mixture of IL-1 (1000 units/ml), IL-6 (5 ng/ml), IL-11 (25 ng/ml), C-kit ligand (100 ng/ml), or C-kit ligand (100 ng/ml), VEGF (5 ng/ml) and EPO (2 units/ml), or C-kit ligand (100 ng/ml) alone. The EB cells were cultured in a final volume of 1 ml in a 35 mm bacterial grade dishes in a humidified environment of 5% $CO_2$ at 37° C. Individual EB cell cultures were incubated for 3 days, 3.5 days, 4 days and 4.5 days. BLAST cell colonies identified using a Leitz inverted light microscope based on morphology. A representative BLAST cell colony is shown in FIG. 2, cell colony B. The BLAST cell colony consisted of a clumped, but not tightly packed, group of cells in which individual cells could be discerned in the colony.

Figure 5:
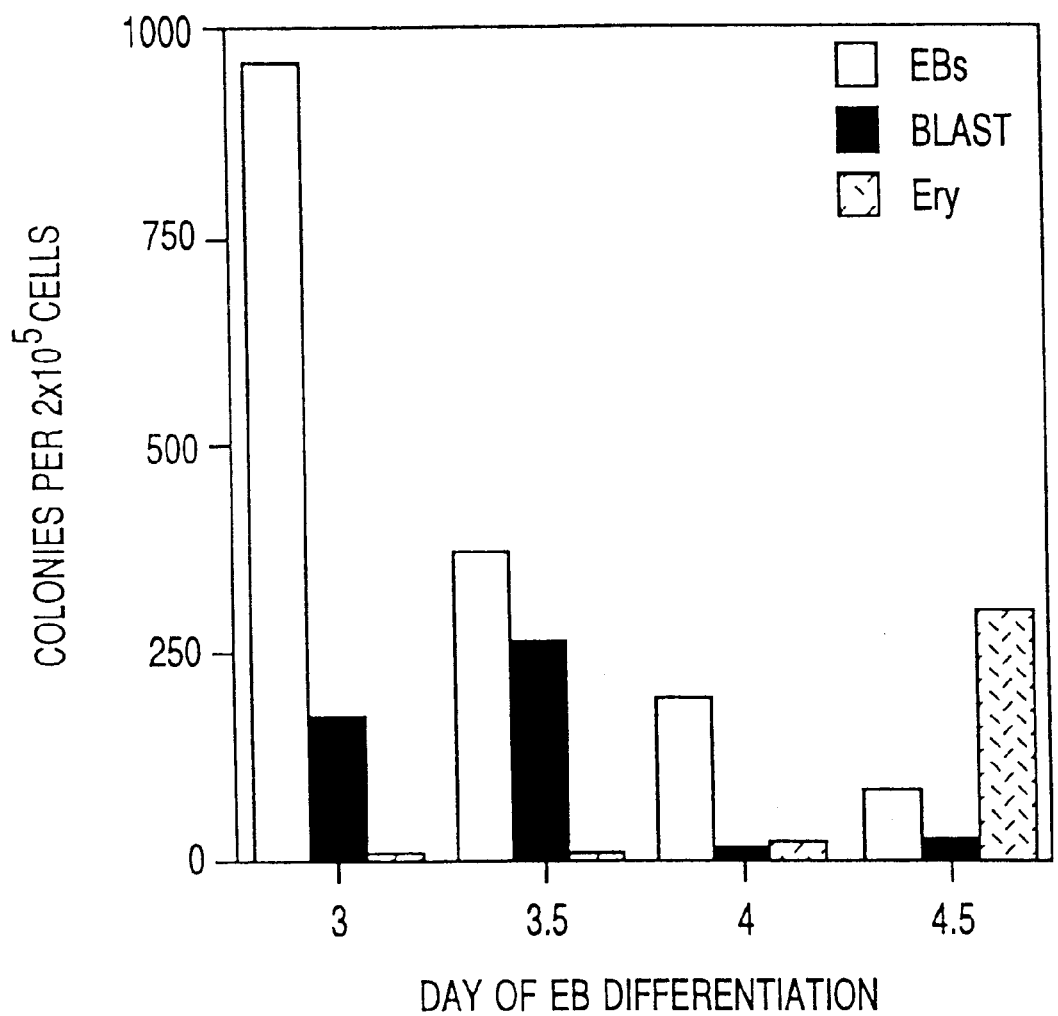
FIG. 5 illustrates the kinetics of embryonic blast cell population development over time.

The formation of BLAST cell colonies at each time point was scored by eye and the kinetics of BLAST cell development are shown in FIG. 5. The results indicate that BLAST cell (Blast) development was detected within 3 days of initiation of EB cell (EBs) incubation under the above culture conditions, increasing slightly in number by day 3.5 and then decreasing to low levels by day 4.5. As the number of BLAST cells increased, the number of EB cells decreased. In addition, as the number of BLAST cells decreased, the number of erythroid cells (Ery), which were scored by red color, appeared at day 4 and continued to increase through day 4.5.

Example 4

This example describes the labelling of a population of BLAST cells using antibodies specific for known cell surface molecules.

EB cells were generated as described in Example 1. BLAST cells were generated from EB cells that had been incubated for about 6 days (Day 6 BLAST) according to the method described in Example 3. The BLAST cells were labelled for fluorescence activated cell sorter analysis using a panel of antibodies against a number of different surface markers. These included antibodies specific for AA4.1, Sca-1, C-kit receptor, H-2b, VLA-4, CD44, CD45 and Thy 1. ES cells and Day 4 EB cells (described in Example 2) were also stained as control samples. The results are shown in FIG. 3. Referring to FIG. 3, the Day 6 BLAST cells (d6 Blasts) stained with anti-CD44, anti-C-kit receptor, anti-Sca-1 and anti-VLA-4 antibodies, but not with anti-H-2b, anti-Thy 1 or anti-CD45 antibodies. Thus, indicating that Day 6 BLASTS express substantial amounts of CD44, C-kit receptor, Sca-1 and VLA-4 protein, and essentially no Class I $H-2^b$, Thy 1 and CD45 protein. Comparing the staining pattern of the Day 6 BLASTS with the EB cell and ES cells, the results show that expression of C-kit receptor, H-2b, VLA-4 and CD44 increases during the 6 days of development of EB cells to BLAST cells.

Example 5

This example describes a myeloid assay to test for hematopoietic precursors in BLAST cell populations.

Figure 6:
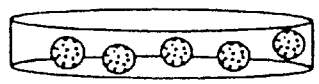
FIG. 6 is a schematic representation of a myeloid assay.
Figure 6:
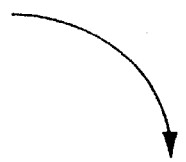
Figure 6:
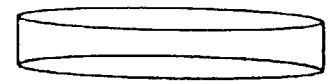
Figure 6:
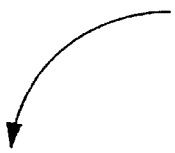
Figure 6:
Figure 6:
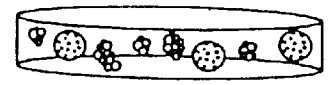

A schematic representation of the myeloid assay used to identify secondary hematopoietic colony formation from BLAST cells is shown in FIG. 6. Two different culture experiments were prepared as follows. In a first experiment, EB cells were generated as described in Example 1 by culturing ES cells for 4 days. Individual BLAST cell colonies were generated by incubating the EB cell population for 3, 4, 5 and 6 days according to the method described in Example 3. In a second experiment, EB cells were generated as described in Example 1 by culturing ES cells for 3, 3.5, 4 and 4.5 days. Individual BLAST cell colonies were generated by incubating each EB cell population for 6 days according to the method described in Example 3. In each experiment, individual BLAST cell colonies were picked, dispersed in 100 µl IMDM containing 5% FCS, and transferred to a 1% methyl cellulose culture containing IMDM, 10% PP-FBS, 300 µg transferrin and a cocktail of growth factors including IL-1 (1000 units/ml), IL-3 (100 Units/ml), IL-6 (5 ng/ml), IL-11 (25 ng/ml), C-kit ligand (100 ng/ml) end EPO (2 units/ml). The cultures were then incubated for varying amounts of time in a humidified 5% $CO_2$, at a temperature of 37° C.

In the first experiment, developing hematopoietic colonies were scored 7 days after initiation of the culture. In the second experiment, developing hematopoietic colonies were scored 3, 4, 5 and 6 days after initiation of the culture. The growth of hematopoietic colonies were scored based on colony morphology when the colonies were viewed under an inverted Leitz light microscope, and based on cellular staining patterns. Erythrocytes, macrophages, neutrophils and mast cells were identified in all cultures having hematopoietic cell development.

Figure 7:
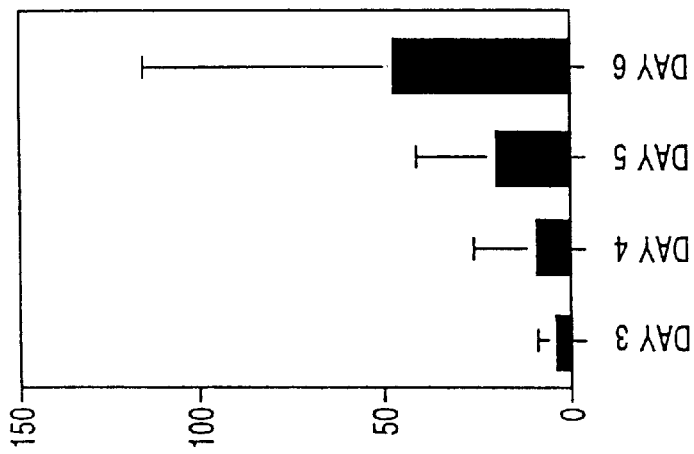
Figure 7:
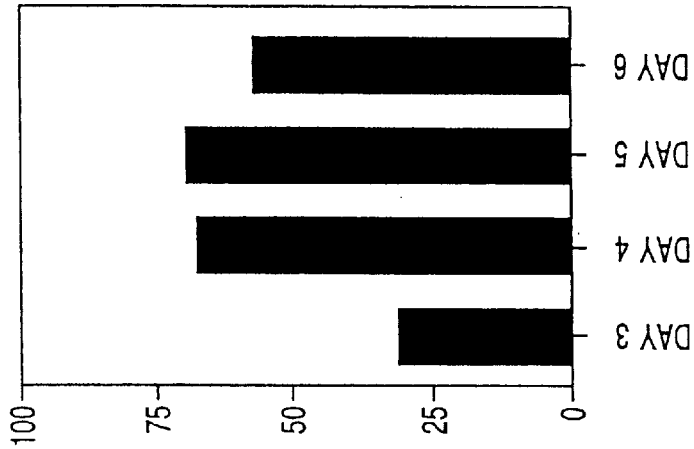

The results from the first experiment indicated that as many as 70% BLAST cells gave rise to hematopoietic colonies (see FIG. 7A). Kinetic analysis revealed that BLAST cell colonies incubated for 3 days gave rise to fewer hematopoietic colonies than BLAST cell colonies incubated for 6 days (see FIG. 7B). Thus, indicating that a maturation process occurred within the BLAST cell population between days 3 and 6.

Figure 8:
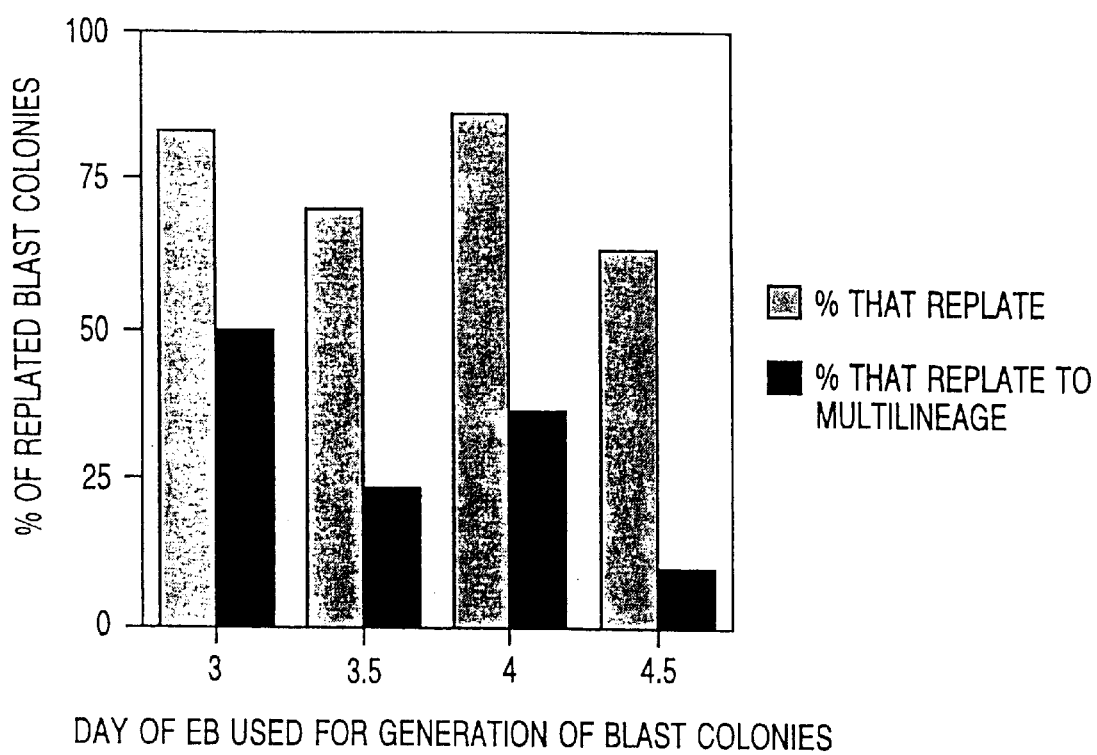
FIG. 8 illustrates the effect of the age of embryoid body cell populations on multi-lineage embryonic blast cell population development.

In the second experiment, the percent of total BLAST cell colonies that generated a secondary hematopoietic colony, including multi- or uni-lineage colonies at each time point was determined. Multi-lineage refers to colonies that contain erythroid plus two other lineages. In addition, the percent of total BLAST cell colonies that generated that generated only multi-lineage colonies at each time point was determined. The results are shown in FIG. 8. Referring to the percent of cells that replate to multi-lineages (black bars), the results indicate that BLAST cell colonies generated from day 3 EB cells contain more immature hematopoietic cells than those derived from day 4.5 EB cells based on the generation of multi-lineage colonies.

Morphological analysis of the secondary hematopoietic populations arising from BLAST cells indicated the presence of primitive erythroid ($Ery^p$), definitive erythroid ($Ery^d$) and multiple myeloid cells in a single replated culture. The results are summarized in Table 1.

TABLE 1

Incidence of Primitive and Definitive Erythroid Colonies from Individually Replated Blast Colonies

| Colony Type | $Ery^p$ | $Ery^d$ (± myeloid) | $Ery^p + Ery^d$ (+ myeloid) |
|---|---|---|---|
| Blast Colonies | 8 | 140 | 10 |

Figure 9:
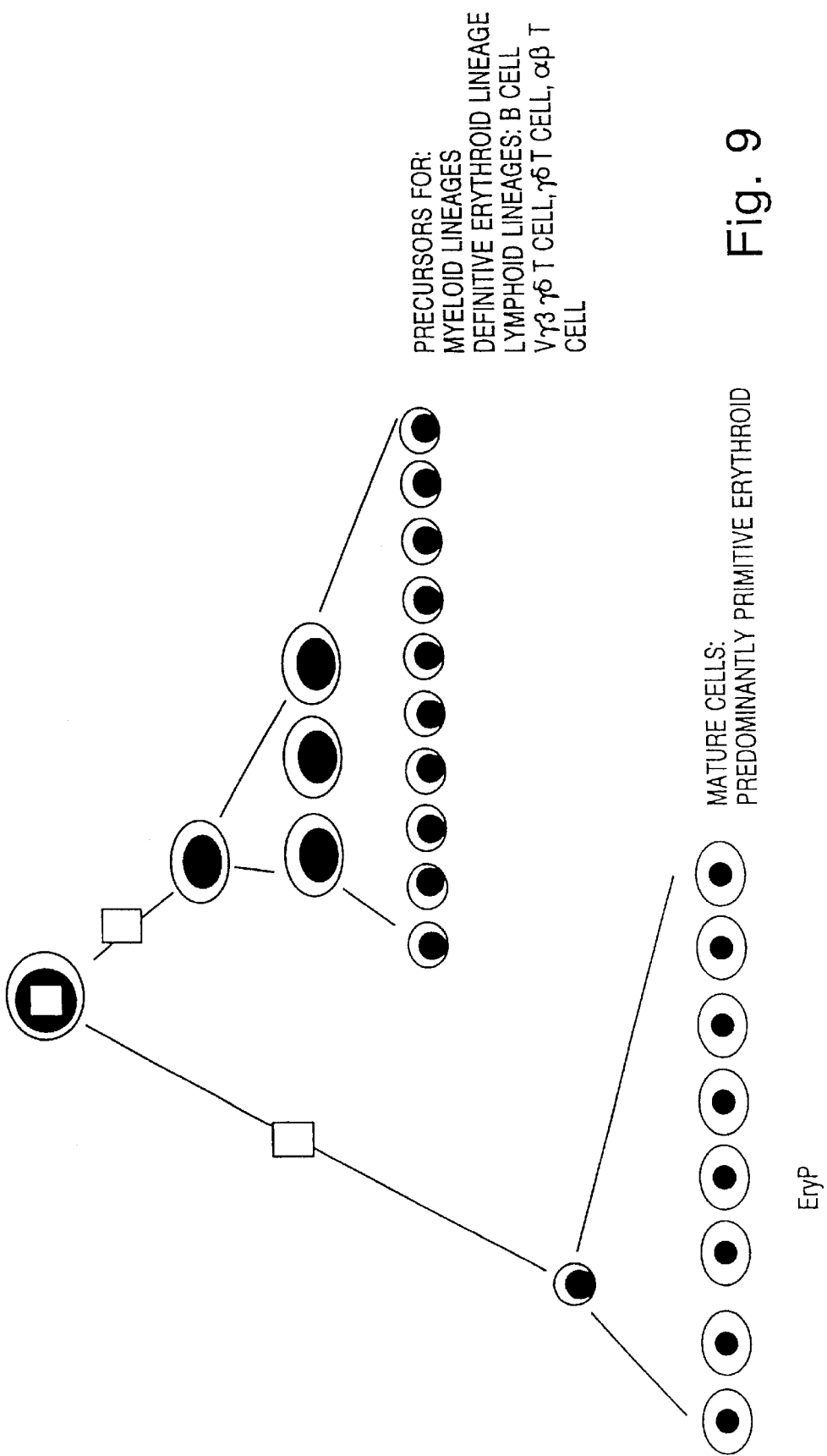
FIG. 9 illustrates a model of hematopoiesis during ontogeny.

The presence of both primitive and definitive erythroid cells in a BLAST cell colony indicates that the BLAST cell population that gave rise to the erythroid cell populations had the potential to generate all hematopoietic populations and represents one of the earliest hematopoietic cells to develop, equivalent to a pre-yolk sac cell (see FIG. 9, cell A). A certain number of BLAST cells generated predominantly primitive erythroid cells, while others generated definitive erythroid cells and cells of the various myeloid lineages. These latter two patterns of replating indicate that some of the BLAST colonies are committed to primitive erythropoiesis (analogous to the cells that expand in the yolk sac) (FIG. 9, cell B); while others have lost the capacity to generate this early lineage, but can generate all other populations (equivalent to the cells that ultimately seed the fetal liver) (FIG. 9, cell C).

Example 6

This example describes the influence of individual growth factors on hematopoietic colony formation from BLAST cell colonies.

Figure 10:
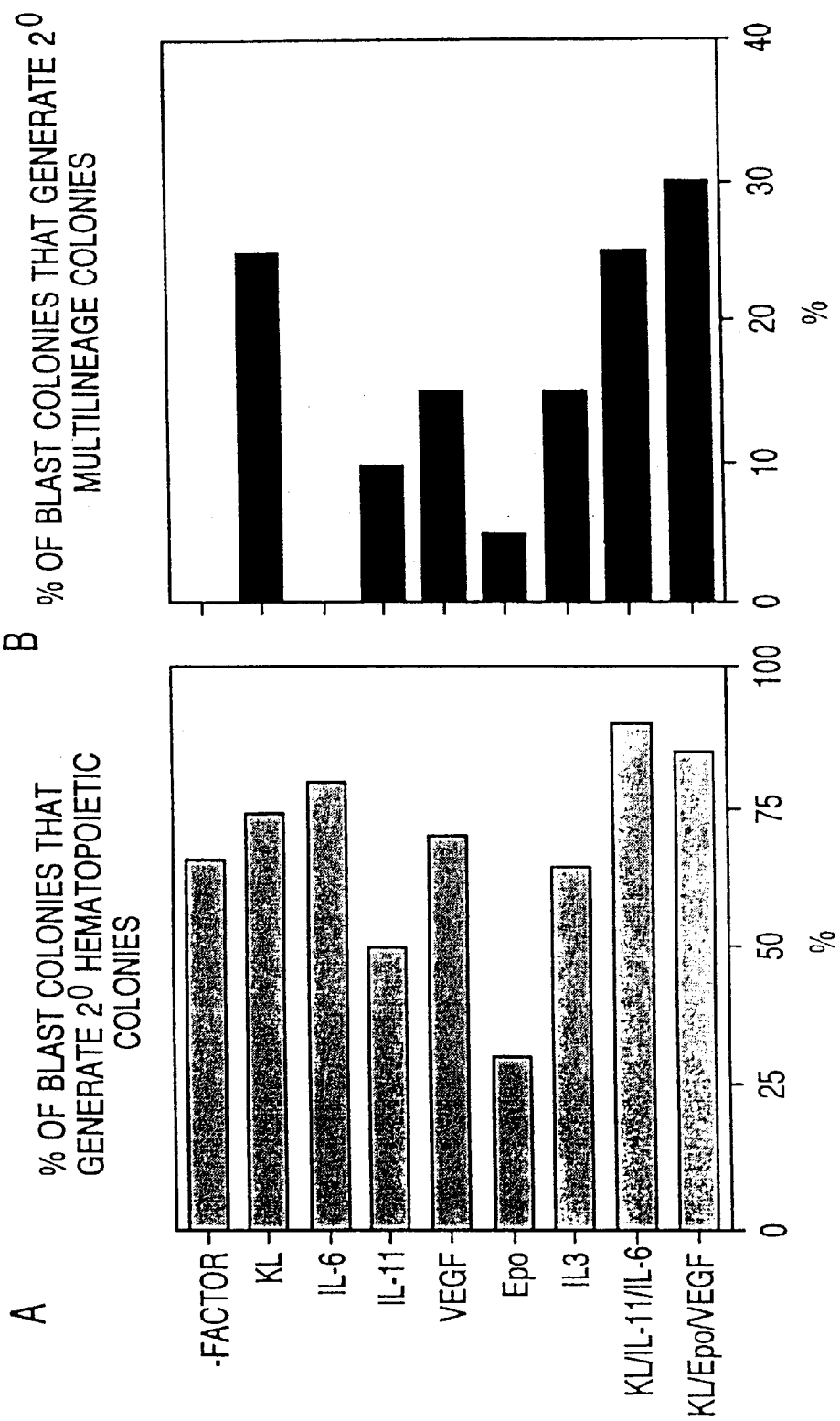
FIGS. 10A and 10B illustrates the effect of specific growth factors on embryonic blast cell population development.

BLAST cell populations were generated from Day 3.5 EB cell populations according to the method described in Example 3 were then incubated in the presence of specific growth factors (shown in FIG. 10). A control sample was prepared that contained no factors (-Factor). Twenty-five individual BLAST cell colonies were picked and replated into a myeloid assay as described in Example 5. The results shown in FIG. 10A indicate that EPO was the least effective growth factor in stimulating the formation of BLAST cell colonies capable of developing into any type of secondary hematopoietic colony. The results shown in FIG. 10B indicate that IL-6 and EPO were the least effective growth factors in stimulating the formation of BLAST cell colonies capable of developing into multi-lineage secondary hematopoietic colonies. C-kit ligand and a mixture of C-kit ligand, EPO and VEGF were most effective in stimulating the formation of BLAST cell colonies capable of developing into any type of hematopoietic colony including colonies having multi-lineage colonies.

Example 7

This example describes the formation of a T cell population from an ES cell population using a mixture of IL-7, IGF-1 and C-kit ligand growth factors.

EB cells were generated from ES cells according to the method described in Example 1. BLAST cell colonies were generated from the EB cells according to the method described in Example 3. Individual BLAST cell colonies were picked, dispersed in IMDM containing 5% FCS, and transferred to a 1% methyl cellulose culture containing IMDM, 10% PP-FBS, 300 μg transferrin and a cocktail of growth factors including IL-7, IGF-1 and C-kit ligand. The cultures were then incubated for about 6 days in a humidified 5% $CO_2$, at a temperature of 37° C.

Thymi were obtained from pregnant (15 days gestation) outbred Swiss Webster mice (purchased from Taconic) which were found to express the Thy 1.1 allele. The thymi were then irradiated at a dose of 3000 Gy to deplete endogenous cells. Pools of 20 BLAST cell colonies were seeded into each thymic lobe in a hanging drop culture in a terrasacki well and incubated for 48 hours. Following the 48 hour hanging-drop culture, the thymi were harvested into IMDM with 10% FCS and transferred to sterile 45 micron filters (Gelman) which were placed on gelfoam sponges (Upjohn) for 3 weeks at the air medium interface. The thymi were then removed from the filter and dissociated by treatment with 0.25% collagenase (Sigma, St. Louis, Mo.), 10 μg/ml DNAse in phosphate buffered saline (PBS) and digested for 1 hour at 37° C. Following digestion, the thymi were dispersed by passaging the cells through a 3 ml syringe attached to a 20 gauge needle.

The resulting single cell suspension was stained for host Thy 1.1, donor Thy 1.2 and T cell receptor expression by the following method. About $4 \times 10^4$ cells were separately incubated with fluorescein isothiocyanate (FITC) labelled anti-Thy 1.2 antibody (1:1000; Pharminogen, San Diego, Calif.), FITC labelled anti-Thy 1.1 antibody (1:1000; Pharminogen)), phycoerythrin (PE) labelled anti-αβ T cell receptor antibody (1:100; Pharminogen), and PE labelled anti-γδ T cell receptor antibody (1:100; Pharminogen) for 20 minutes, on ice. The cells were washed and analyzed on a FACSCAN (Becton Dickinson).

Figure 11:
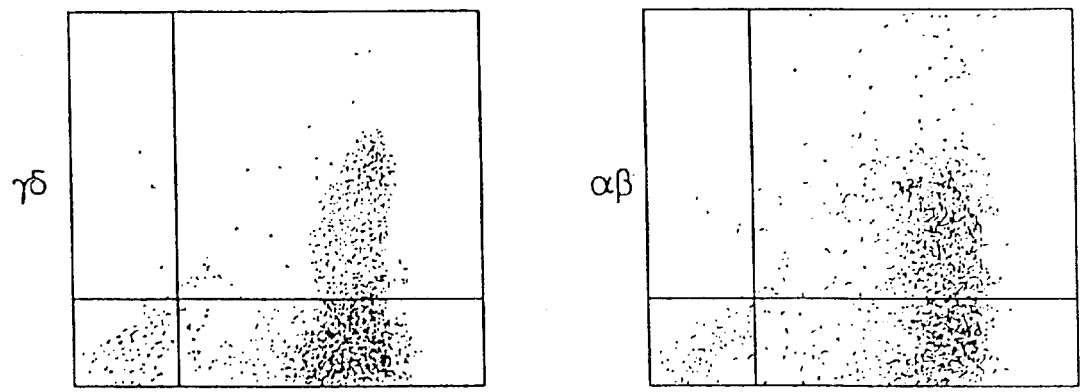
FIG. 11 illustrates T cell receptor expression by an embryonic stem cell-derived T cell population.
Figure 11:
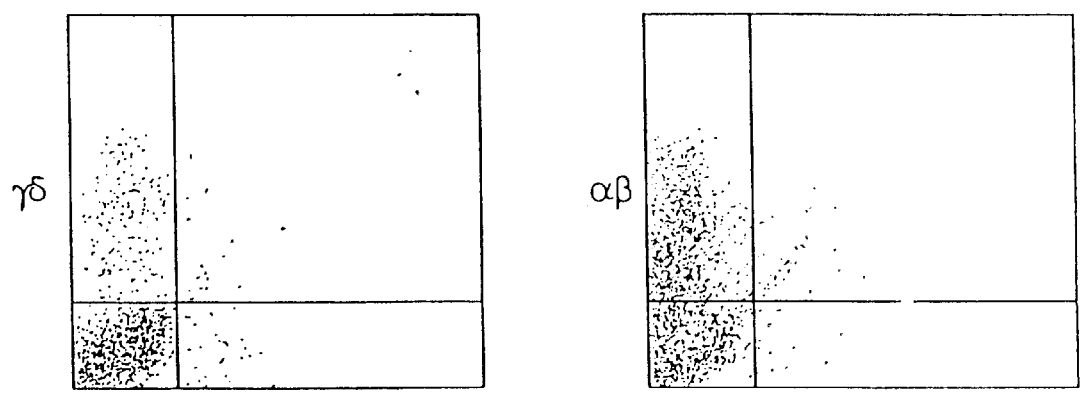

Referring to FIG. 11, donor Thy 1.2 positive cells expressing both αβ and γδ T cell receptor were detected indicating that a mature T cell population was derived from the donor BLAST cell colonies that had been treated with IL-7, IGF-1 and C-kit ligand.

Example 8

This example describes the formation of a T cell population from an ES cell population using varying combinations of growth factors.

BLAST cell colonies were generated as described in Example 7. Individual BLAST cell colonies were then incubated with different combinations of growth factors including C-kit ligand alone, a mixture of C-kit ligand and IL-7, a mixture of C-kit ligand, IL-7 and IGF-1 and a mixture of C-kit ligand, VEGF and EPO. Using the method described in Example 7, the BLAST cell colonies were incubated, T cell populations were derived, and the resulting T cell populations were stained with anti-Thy 1.2 and αβ T cell receptor antibodies.

Figure 12:
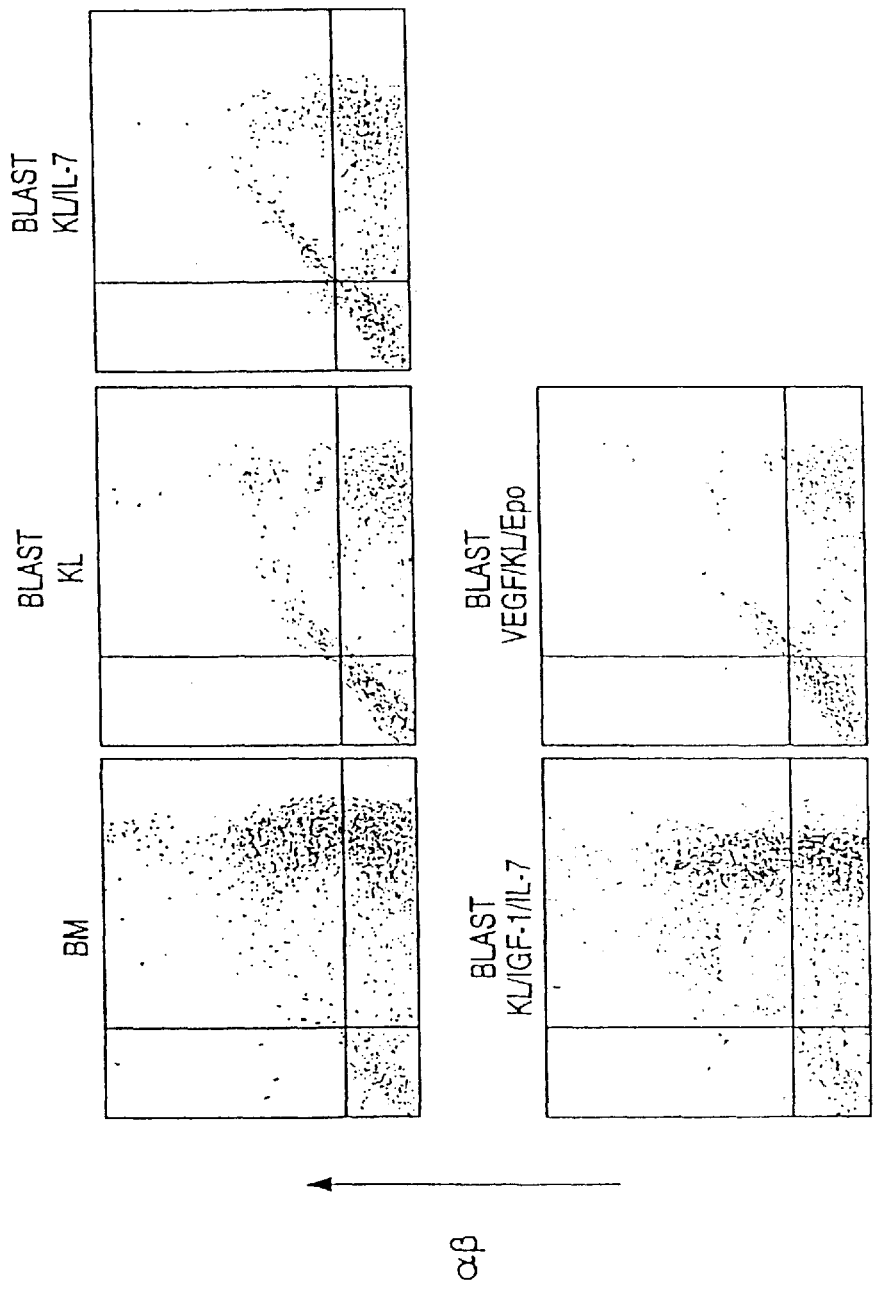
FIG. 12 illustrates the effect of specific growth factors on T cell receptor expression by an embryonic stem cell-derived T cell population.

Referring to FIG. 12, incubation of BLAST cell colonies with the combination of C-kit ligand, IL-7 and IGF-1 growth factors (BLAST KL/IGF-1/IL-7) produced the most αβ T cell receptor positive T cells. The presence of the other combinations of factors, however, also produced some αβ T cell receptor positive T cells. A positive control sample of bone marrow stromal cells BLAST cell colonies (BM) produced similar numbers of αβ T cell receptor positive T cells as the KL/IGF-1/IL-7 treated BLAST cell colonies. Thus, optimal conditions for production of T cell populations include incubation of BLAST cell colonies with a mixture of C-kit ligand, IL-7 and IGF-1 growth factors.

Example 9

This example describes the formation of a B cell population from an ES cell population.

EB cell colonies were generated from ES cells using the method of Example 1. BLAST cell colonies were derived from EB colonies using the method of Example 3. Individual BLAST cell colonies were picked from methyl cellulose culture and transferred to confluent monolayers of S17 bone marrow stromal cells that had been irradiated at a dose of 3000 Gy. Cultures were grown for 4 weeks in IMDM with 5% FCS and C-kit; ligand. cDNA samples were prepared from the C-kit ligand treated cells by dispersing the cells using trypsin, lysing the cells and preparing cDNA using reverse transcriptase (BRL Gibco) according to methods standard in the art. cDNA samples were then amplified by PCR for VDJ immunoglobulin rearrangement using a 5' VH7183 primer (5'-TGGTGGAGTCTGGGGGAGGCTTA-3'; SEQ ID NO: 1) and a 3' JH4 primer (5'-GGCTCCCTCAGGGACAAATATCCA-3'; SEQ ID NO: 2) using the following PCR profile: 94° C. 1 minute, 72° C. 2 minutes for 29 cycles; 94° C. 1 minute, 72° C. 10 minutes for one cycle. PCR products were subjected to southern blotting and hybridized with a probe complimentary to a sequence common to immunoglobulin J regions.

The results indicate that treatment of BLAST cells with C-kit ligand in addition to exposure to bone marrow stromal cells results in the production of a B cell population containing cells having rearranged immunoglobulin VDJ genes.

Example 10

This example describes the development mixed populations of erythroid and endothelial cells from EB cell populations.

A. Mixed Endothelial and Erythroid Population Development

Approximately $2 \times 10^5$ EB cells derived from CCE ES cells that were cultured for about 4 days according to the method described in Example 1 were dissociated with trypsin and re-plated and cultured in 1% methyl cellulose made in IMDM containing 10% PP-FBS, transferrin (300 μg/ml), glutamine (2 mM), VEGF (5 ng/ml) and EPO (2 units/ml). The EB cells were cultured in a final volume of 1 ml in a 35 mm bacterial grade dishes in a humidified environment of 5% $CO_2$ at 37° C. The EB cells were cultured for about 7 days.

The resulting "mixed" cell population was viewed under an inverted Leitz microscope. Under the above culture conditions, 3 different morphological types of cell colonies arose and representative cells are shown in FIG. 4. A first cell type, indicated as cell A in FIG. 4, consisted of an erythroid cell having the typical characteristics of a distinct compact cluster of small cells having red color. A second cell type, indicated as cell B in FIG. 4, consisted of a spherical cell having a larger size than an erythroid cell, such as cell A. A third cell type, indicated as cell C in FIG. 4, consisted of a spherical cell having a similar size as an erythroid cell but having a single long process extending from the cell.

B. Kinetics of Mixed Erythroid and Endothelial Population Development

Figure 13:
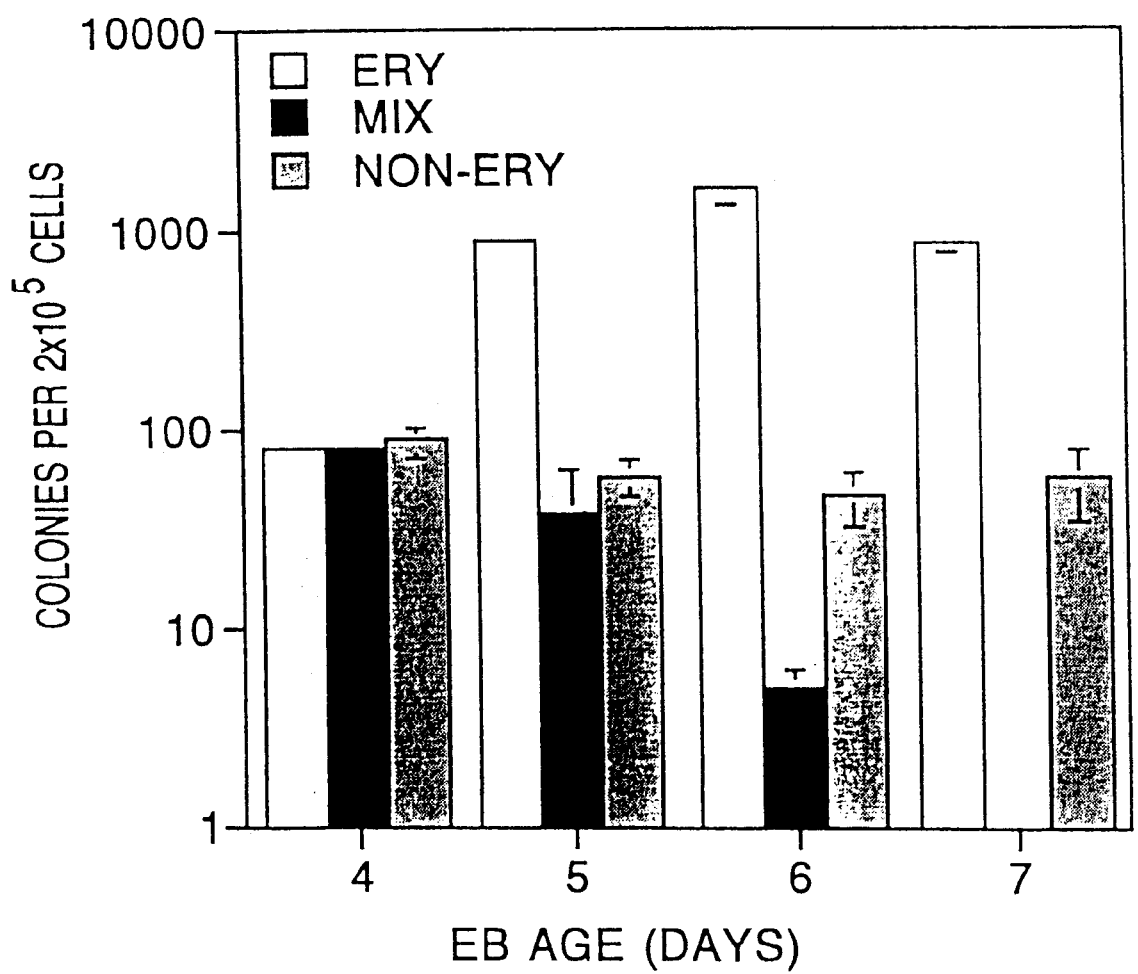
FIG. 13 illustrates the effect of the age of an embryoid body cell population on the development of a mixed population of erythroid and endothelial cells.

Varying EB cell populations were generated using the method described above in section A by incubating ES cells for 4, 5, 6 and 7 days. Various types of colonies were then scored about. 7 days following plating based on the 3 different morphologies described in Section A and cultures containing erythroid (ERY) and non-erythroid (NON-ERY) cells were scored as "mixed" (MIX) populations. Referring to FIG. 13, the results indicate that the number of mix colonies decreases with increasing age of EB cells and are almost undetectable by day 7. Meanwhile, erythroid colonies increased in number between days 4 and 6 of differentiation.

Figure 14:
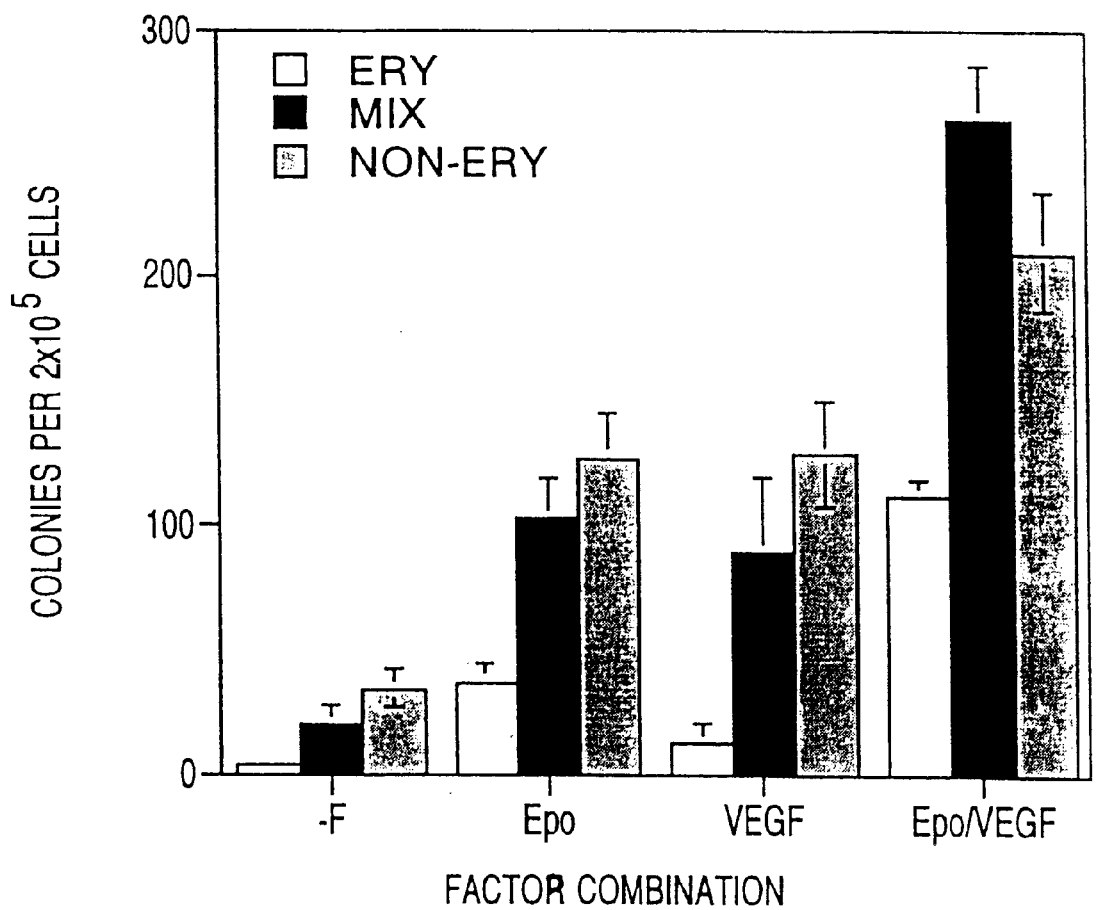
FIG. 14 illustrates the effect of specific growth factors on the development of a mixed population of erythroid and endothelial cells.

C. Influence of Specific Growth Factors on Mixed Erythroid and Endothelial Population Development An EB cell population was generated using the method described above in section A by incubating ES cells for 4 days. In a first experiment, the effect of specific growth factors on the development of mixed endothelial and erythroid cell populations was tested. Separate populations of Day 4 EB cells were plated in the presence of EPO (2 units/ml) alone, VEGF (5 ng/ml) alone, a mixture of EPO and VEGF, or no factor. The cultures were then scored for erythroid (ERY), non-erythroid (NON-ERY) cells and mixed (MIX) cell populations as described above. Referring to FIG. 14, the results indicate that the combination of EPO and VEGF growth factors induced the best EB cell differentiation, in particular to mixed cell populations.

Figure 15:
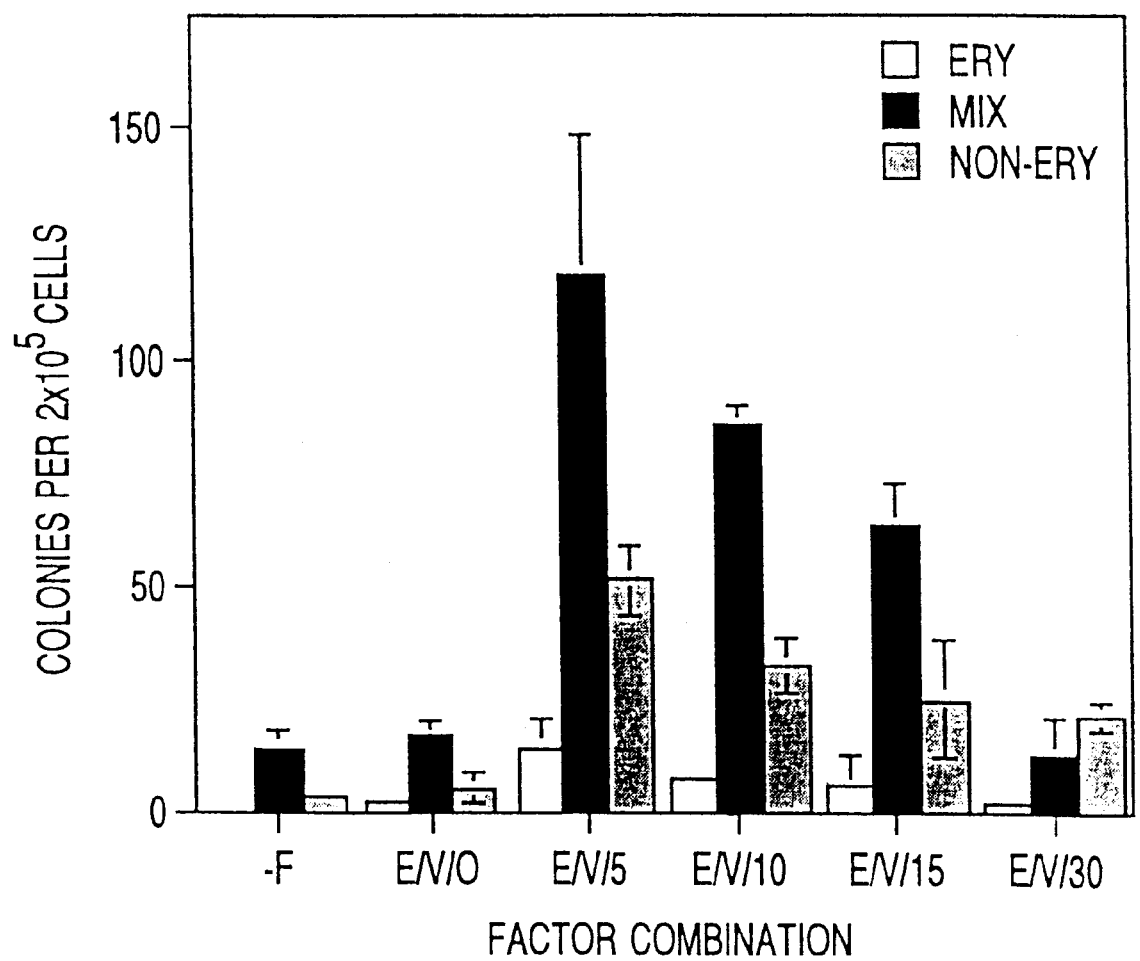
FIG. 15 illustrates the effect of the concentration of specific growth factors on the development of a mixed population of erythroid and endothelial cells.

In a second experiment, the concentration of specific growth factors on the development of mixed endothelial and erythroid cell populations was tested. Separate populations of Day 4 EB cells were plated in the presence of 0 nanograms (ng) per ml of EPO+VEGF (E/V/0), 5 ng/ml EPO+VEGF (E/V/5), 10 ng/ml EPO+VEGF (E/V/10), 15 ng/ml EPO+VEGF (E/V/15), 30 ng/ml EPO+VEGF (E/V/30), and no factor (-F). The cultures were then scored for erythroid (ERY), non-erythroid (NON-ERY) cells and mixed (MIX) cell populations as described above. Referring to FIG. 15, the results indicate that 5 ng/ml of the combination of EPO and VEGF growth factors induced the best EB cell differentiation, in particular to mixed cell populations.

D. von Willebrand Factor and Acetylated-LDL Staining of Mixed Cell Populations

A mixed population of cells derived from the method described in Section A was stained with the endothelial cell specific marker von Willebrand factor (vWF) and diI-Acetylated-low density lipoproteins (DiI-Ac-LDL). The mixed colonies were picked from methyl cellulose culture and allowed to adhere overnight to cover slips that were coated with poly-L-lysine or gelatin. Cells were stained for vWF by the following method. Cells attached to cover slips were fixed for 10 minutes in a solution containing 3% paraformaldehyde and 3% sucrose in PBS. After washing 2 to 3 times, the cells were permeabilized with 0.2% Triton X-100 in PBS. A solution of normal mouse serum and human immunoglobulins was used to block non-specific binding. Subsequently, the cells were incubated with a rabbit anti-human vWF antibody for: L hour and washed 5 times, 5 minutes each wash. The cover slips were then incubated with horse radish peroxidase labelled goat anti-rabbit antibody (obtained from Fisher) for 1 hour and washed for 5 times, 5 minutes each wash. The labelled cells were then incubated for 15 minutes in a solution containing 0.5 mg/ml of diaminobenzidine, 3 mg/ml nickel sulfate, 0.003% $H_2O_2$, and 100 mM Tris (pH 7.5).

Figure 16A:
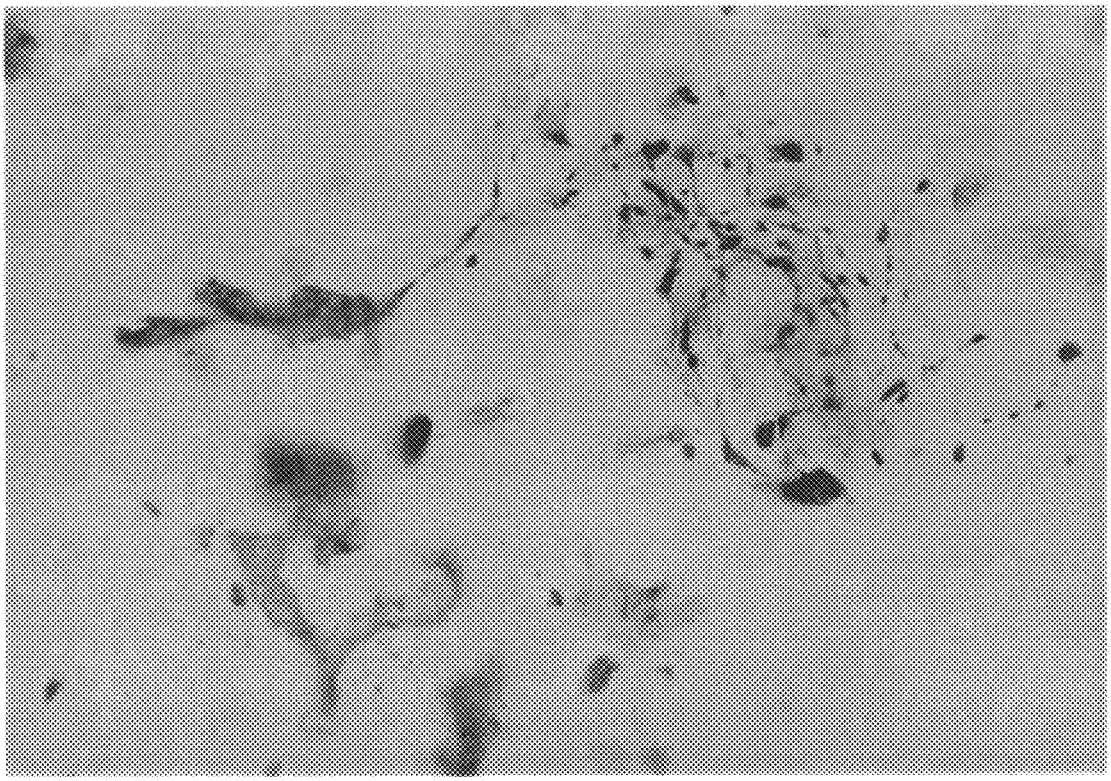
FIGS. 16A–C shows representative microscopic fields of view of a mixed population of erythroid and endothelial cells stained with von Willebrand factor.
Figure 16B:
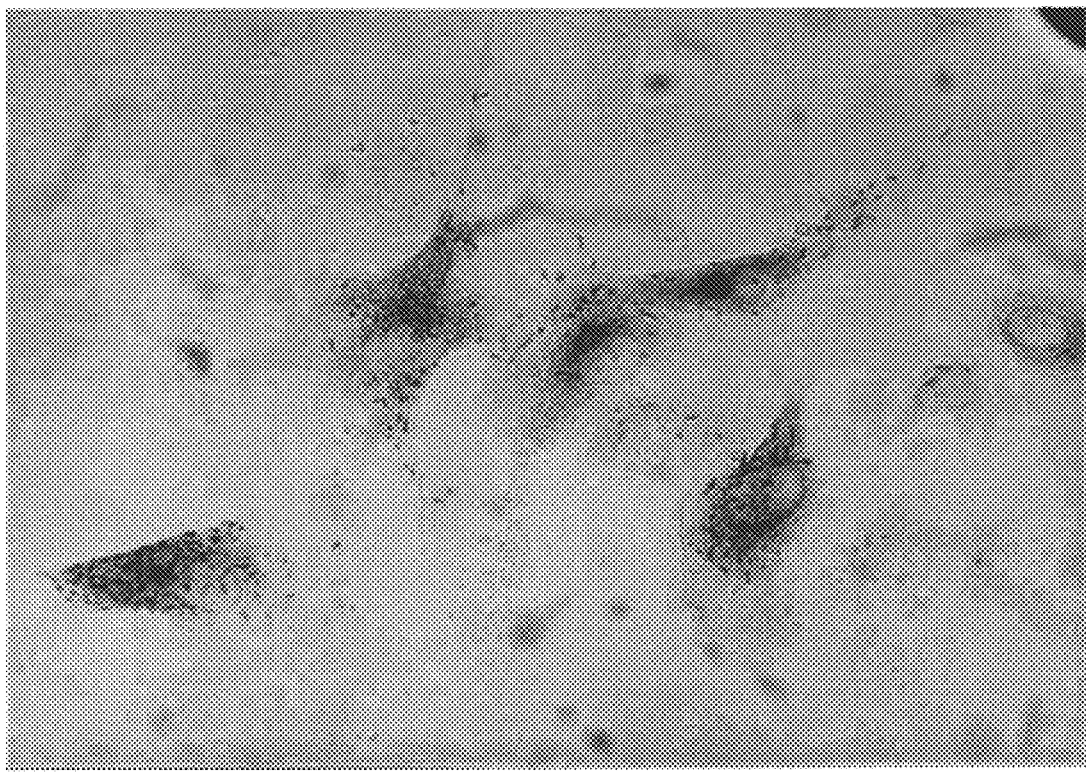
Figure 16C:
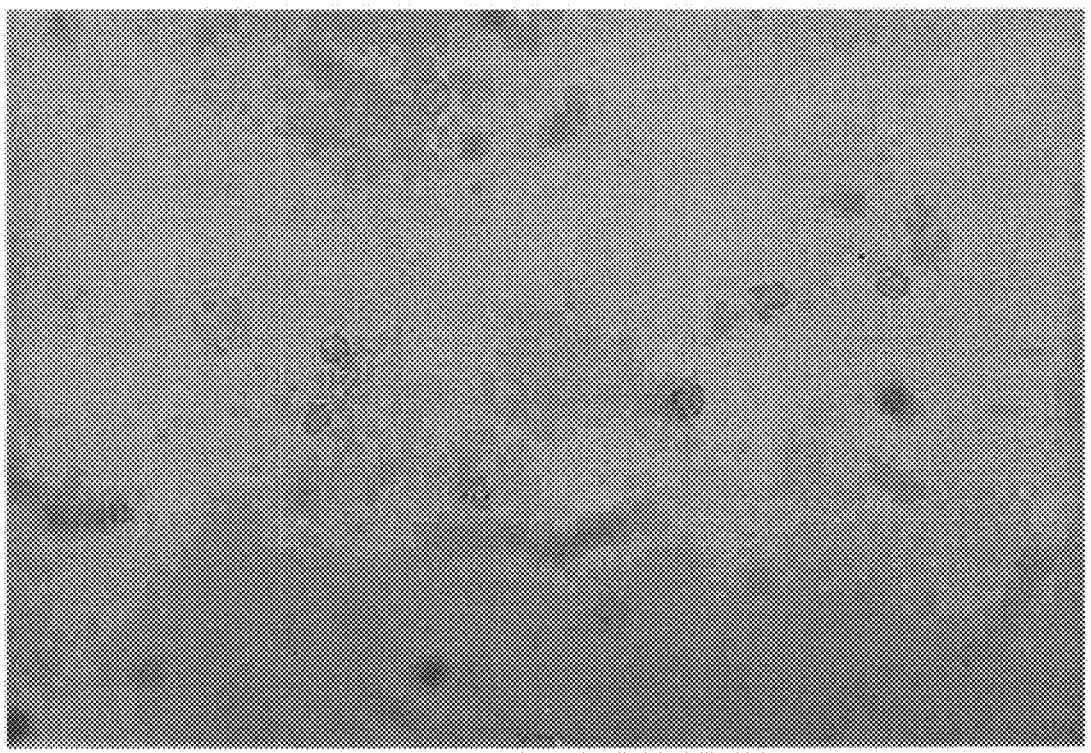

The vWK stained cells were analyzed by eye. The results indicated that two of the three cell types identified in the mixed population (described above in Section A) were labelled with vWF. A representative filed of stained cells is shown in FIG. 16. Referring to FIG. 16A, the cells described in Section A that had long processes stained with vWF. Referring to FIG. 16B, the cells described in Section A that were larger than the red erythroid cells also stained with vWF. The red erythroid-like cells identified in section A sis not stain with vWF. Referring to FIG. 16C, a control population of macrophage cells also failed to stain with vWF. These results indicate that the non-erythroid cells in the mixed population having long processes or having a larger size than the erythroid cells stain with an endothelial cell specific marker.

Cells were tested for LDL uptake by the following method. Ten μg/ml DiI-Ac-LDL was added to the medium of cultures of mixed cell populations and incubated for 4 hours at 37° C. Following incubation, the cells were washed 3 times and fixed with a solution of 3% paraformaldehyde and 3% sucrose in PBS. Following fixation, the cells were mounted on glass slides using 90% glycerol and 10% PBS and analyzed by eye. The results indicated that the non-erythroid cells in the mixed population having long processes or having a larger size than the erythroid cells took up the DiI-Ac-LDL, an endothelial cell specific stain.

Taken together, the observation that the non-erythroid cells generated in the presence of VEGF stained with both vWF and DiI-Ac-LDL indicates that the non-erythroid cells represent endothelial cells and therefore the mixed colonies appear to contain both hematopoietic and endothelial cells.

Example 11

This example demonstrates that erythroid and endothelial cells in a mixed population arose from a common precursor cell.

Figure 17:
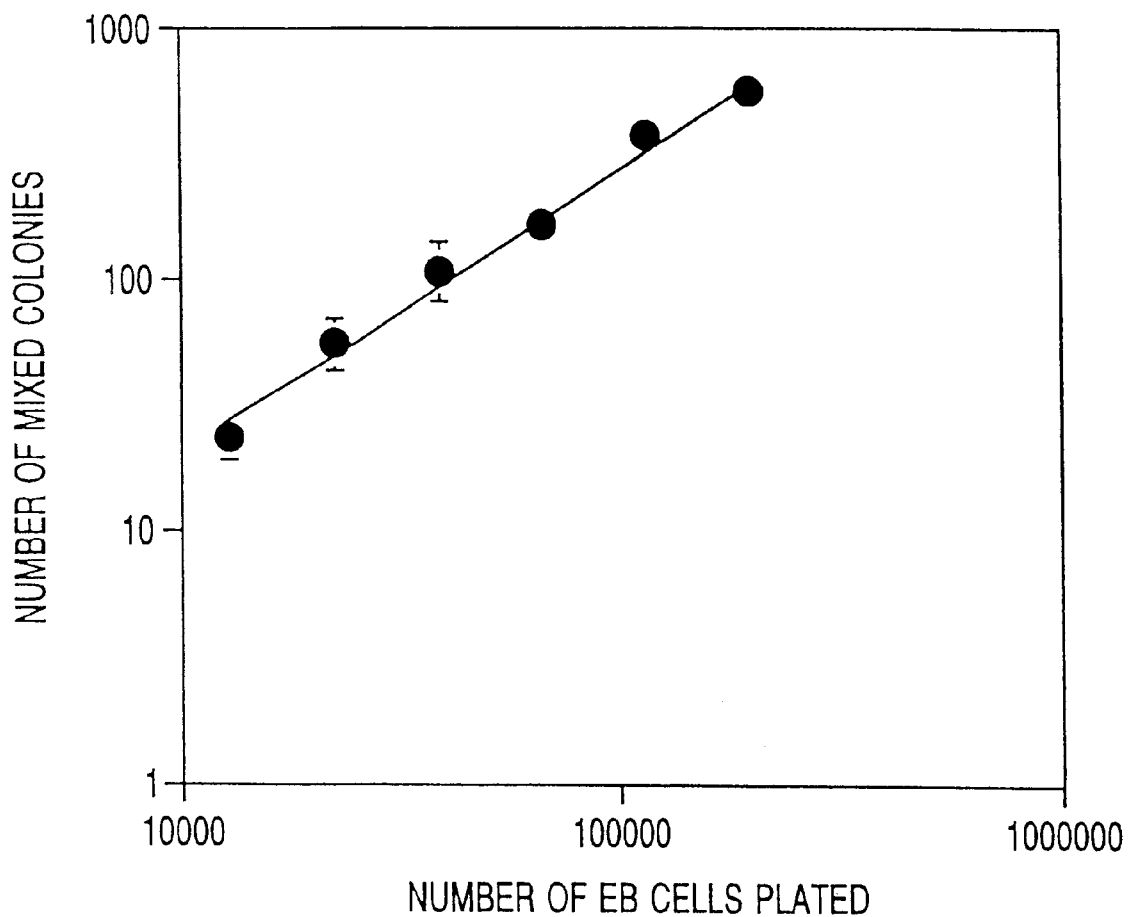
FIG. 17 illustrates the clonality of the development of a mixed population of erythroid and endothelial cells.

EB cell colonies were generated using the method described in Example 1. To determine if the differentiation of EB cells in the presence of VEGF and EPO was significantly reduced in GATA-2$^-$ EB cells, varying numbers of GATA-2$^+$ EB cells (see FIG. 17) were plated into Methyl cellulose cultures containing VEGF, EPO and 2×10$^5$ GATA-2$^-$ EB cells (as feeder cells; kindly provided by Dr. Stuart Orkin at Children's hospital in Boston). The cultures were then analyzed for the development of mixed colonies under an inverted Leitz microscope. It was found that when a standard number of GATA-2$^-$ EB cells were added to cultures containing varying numbers of GATA-2$^+$ EB cells, a linear relationship between the number of mixed colonies and the number of GATA-2$^+$ EB cells was observed. When plotted in a log:log format, the slope of this relationship was not significantly different from 1, a finding which indicates that the colonies derive from a single cell (see FIG. 17).

Example 12

This example describes confirmation studies of the single cell origin of mixed colonies using a retroviral marking technique.

Retroviruses that carry unique inserts in addition to G418 resistant marker (retroviral vector LNCX based) were used to mark EB cell populations generated according to the method of Example 1. Day 4 EB cell populations were dissociated with trypsin and incubated with retroviruses in the presence of polybene (5 μg/ml), VEGF, EPO, and IGF-1. After 5–8 hours, the cells were incubated in a 1% methyl cellulose culture with VEGF, EPO and G418 (150 μg/ml). Cells were routinely dispersed using a syringe attached to a 20 gauge needle because the cells tended to aggregate during viral infection. The resulting mixed colonies were picked into 0.1×PBS and lysed for 8 minutes at 95° C., treated with proteinase K, heat denatured for 8 minutes at 95° C., and subjected to PCR amplification. LNCX retroviral vector sequence was used for the cDNA amplification. An upstream primer (5'-CGCGGCCCCAAGCTTGTTAACATCGATGGATG-3'; SEQ ID NO: 3) and a downstream primer (5'-GGCGTTACTTAAGCTAGCTTGCCAAAGGTAC-3'; SEQ ID NO: 4) were used. PCR products were gel purified and subjected to further amplification. After PCR amplification, excessive primers were removed by filtration through centricon 30 filters and the DNA was concentrated by ethanol precipitation. The presence of the insert sequence at the junction of cDNA insert and LNCX retroviral vector was analyzed in 7 G418 resistant mixed colonies by sequencing using standard dideoxy sequencing methods.

The sequence analysis indicated that all of the G418 resistant mixed colonies contained the same insert sequence, thereby indicating that the mixed colonies arose from a single clone.

In summary, the results from experiments involving mixed endothelial and erythroid cell population formation indicate that there is a close association of erythroid and endothelial cell development from a common precursor. A mixed erythroid and non-erythroid cell population can be generated using the growth factors VEGF and EPO. The relationship between the number of mixed colonies generated and the number of cells plated was linear and individual mixed colonies marked with unique retroviruses revealed that these colonies mixed colonies are derived from a common precursor that gave rise to both blood and endothelial cells.

Example 13

This example describes the production of HOX11 immortalized precursor cell populations.

A. Preparation of Recombinant MSCV-HOX11 Retrovirus Expression Vector

The plasmid MSCV-HOX11 (described in Hawley et al., *Oncogene* 9:1–12, 1994) was constructed by blunt-end ligating a 1,152 base pair (bp) ApaI fragment (positions 231 to 1382) of the human HOX11 (referred to herein as TCL-3) cDNA (described in detail in Lu et al., *EMBO J.* 10:2905–2910, 1991) into the HpaI site of the MSCVv2.1 retroviral vector (described in Hawley et al., *J. Exp. Med.* 176:1149–1163, 1992; Hawley et al., *Gene Therapy* 1:136–138, 1994), which contains a neomycin phosphotransferase (neo) gene conferring resistance to G418 (Geneticin, Life Technologies).

To produce replication-defective recombinant virus, MSCV-HOX11 plasmid was linearized by digestion with NdeI and then electroporated into GP+E-86 ecotropic helper-free packaging cells (described in Markowitz et al.,*J. Virol.* 62:1120–1124, 1988) using the methods described in Hawley et al. (*Plasmid* 22:120–131, 1989). The electroporated cells were then cultured for about 24 hours. Cell-free (filtered through a 0.45-μm filter) supernatant was then collected and used to infect tunicamycin-treated (0.1 μg/ml for 16 hours) GP+E-86 cells (described in Hawley et al., *Leukemia Res.* 15:659–673, 1991). The infected cells were cultured in Dulbecco's modified Eagle medium (DMEM) containing about 400 μg/ml G418 for about 11 days. Following selection, about 100 colonies were pooled and propagated as a mass culture (referred to herein as GP+E-86/MSCV-HOX11 cells). GP+E-86/MSCV-HOX11 cells were maintained in DMEM containing 4.5 g/l glucose and 10% calf serum in a humidified atmosphere containing 5% $CO_2$ at 37° C. Control GP+E-86/MSCVv2.1 cells exporting parental MSCVv2.1 virus were similarly generated.

The GP+E-86/MSCV-HOX11 and GP+E-86/MSCVv2.1 were transferred to DMEM medium containing 150 μM monothioglycerol and 15% heat inactivated fetal calf serum and cultured until the cultures were subconfluent (about 24 hours). Virus-containing supernatants were then collected, filtered through 0.45-μm filters and used immediately to infect CCE embryonic stem (ES) cells. GP+E-86/MSCV-HOX11 and GP+E-86/MSCVv2.1 producers have titers of 4–8×10⁶ colony-forming units/ml when assayed on NIH3T3 fibroblasts in the presence of 400 μg/ml G418.

B. Infection of CCE ES Cells with MSCV-HOX11 Plasmid

Figure 18:
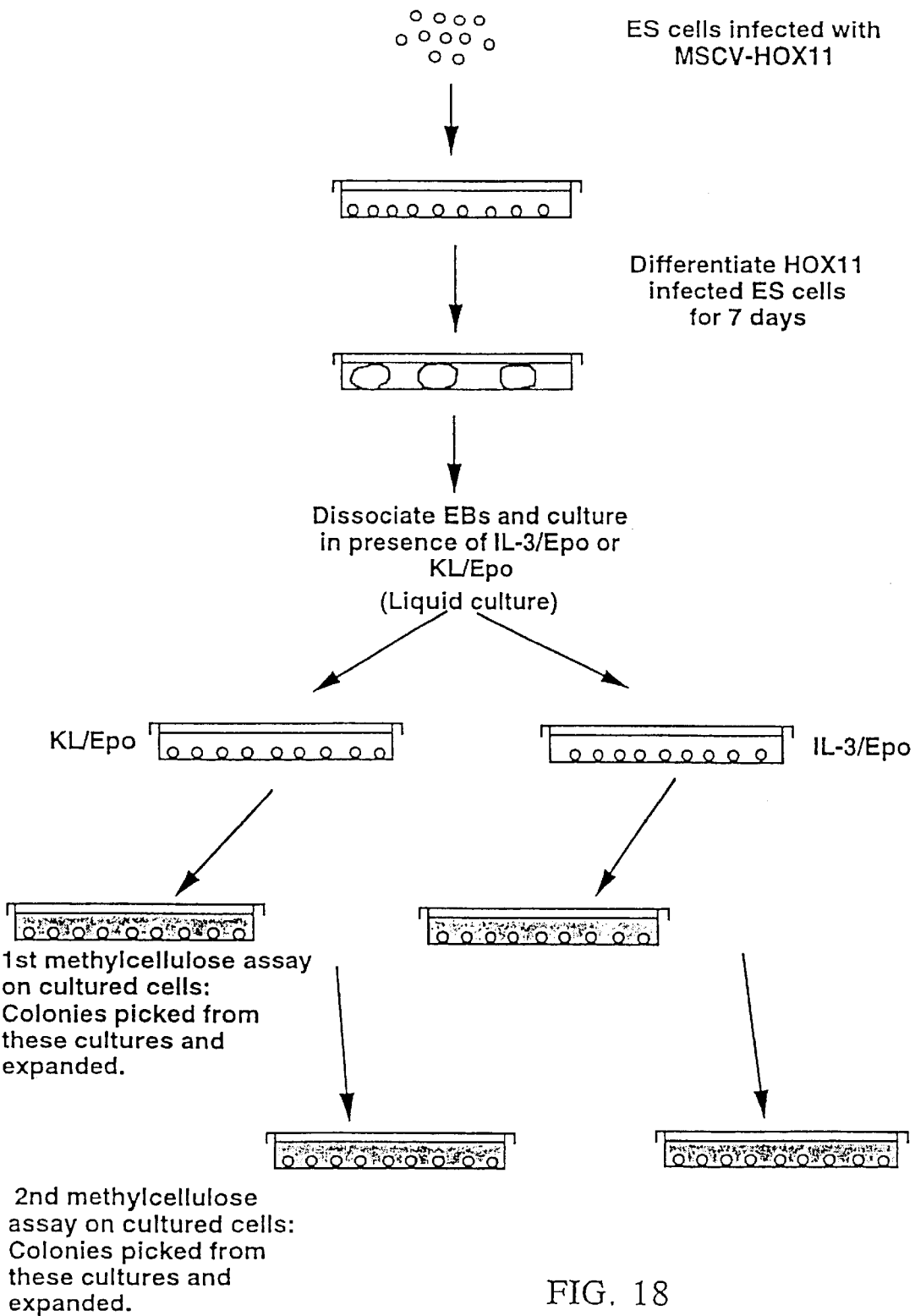
FIG. 18 illustrates a schematic representation of the method used to develop an immortalized HOX11 cell population.

The method for preparing an EBHX cell population is schematically illustrated in FIG. 18.

CCE ES cells were retrieved from frozen stocks of cells that had been cultured for about 17 passages (about 30 days). The thawed cells were cultured for one passage (about 2 days) in DMEM medium containing 150 μM monothioglycerol and 15% heat inactivated fetal calf serum (referred to herein as growth medium) in the presence of LIF) on 0.1% gelatinized dishes (described in Keller et al., *Mol. Cell. Biol.* 13:473–486, 1993). The culture medium was removed from the monolayer of ES cells. Separately, about 1 ml of freshly harvested virus-containing supernatants from GP+E-86/MSCV-HOX11 cells or 1 ml of freshly harvested virus-containing supernatants from GP+E-86/MSCVv2.1 cells, each supplemented with 1% LIF conditioned medium and 8 μg/ml polybrene (Sigma, St. Louis, Mo.) was added to about 4×10⁵ cells. The cells were incubated at 37° C. for 2 hours with occasional rocking (about every half hour). After about 2 hours, 4×volume DMEM growth medium was added and the incubation continued overnight. The infection was repeated the next day. The doubly infected population was then expanded and cultured in the presence of 500 μg/ml G418 for about 2 days. The medium was then changed and the cells further cultured for about another 24 hours. The cells were trypsinized and recovered. One half of each culture was frozen at –80° C. The remainder of the cells were cultured for about 48 hours in G418-supplemented DMEM growth medium and then replated at a 1:8 dilution (aliquots were also frozen at –80° C. at this time). The replated cells were then cultured for about 7 days in G418-supplemented DMEM growth medium, the cells were harvested (aliquots were also frozen at –80° C. at this time).

Example 14

This example describes the selection of EBHX cell populations of the present invention from HOX11 transformed ES cell populations.

EB-HOX11 transformed cell populations were generated using the following method. HOX11 transformed ES cells described in Example 13 were trypsinized, washed and counted using techniques standard in the art. The freshly dissociated transformed cells were then cultured in IMDM containing 15% platelet-derived fetal bovine serum (PDS; obtained from Antech, TEXAS; also referred to herein as platelet-poor fetal bovine serum, PP-FBS), 4.5×10⁻⁴ M MTG, transferrin (300 μg), glutamine (2 mM). The HOX11 transformed cells were plated in a final volume of 10 ml at a concentration of about 3000 to about 4500 cells per ml of medium in 100 mm bacterial grade dishes. The HOX11 transformed cell population was then cultured in a humidified environment of 5% $CO_2$, at a temperature of 37° C. for about 7 days to form an EB-HOX11 transformed cell population. Following the 7 day incubation, EB-HOX11 transformed cell populations were harvested using standard techniques.

Cells from EB-HOX11 transformed cell populations were then further differentiated into EBHX populations of the present invention using the following method (see FIG. 18). A series of cultures were prepared by plating about 5×10⁵ EB-HOX11 transformed cells and culturing the cells in liquid culture comprising IMDM containing 10% pre-selected normal FCS, transferrin (300 μg/ml), glutamine (2 mM), and either a mixture of C-kit ligand (100 ng/ml) and EPO (2 units/ml) or IL-3 (saturating amounts) and EPO (2 units/ml). The EB-HOX11 transformed cells were cultured in a final volume of 1 ml in a 100 mm bacterial grade dishes in a humidified environment of 5% $CO_2$ at 37° C. for from about 1 day to about 100 days.

At specific times, cells were cultured in a first methyl cellulose culture step comprising 1% methyl cellulose containing either a mixture of C-kit ligand (100 ng/ml) and EPO (2 units/ml) or IL-3 (saturating amounts) and EPO (2 units/ml). Individual colonies were then recovered from this culture and expanded. The expanded colonies are referred to herein as EBHX cell populations.

Portions of EBHX cell populations from this first methyl cellulose step were either frozen at –70° C. and stored, or further cultured in a second methyl cellulose step comprising 1% methyl cellulose containing either a mixture of C-kit ligand (100 ng/ml) and EPO (2 units/ml) or IL-3 (saturating amounts) and EPO (2 units/ml). Individual colonies were then recovered from this culture, expanded and either frozen or maintained in culture.

Referring to FIG. 18, EBHX-1 through EBHX-7 (also referred to herein as Lines 1 through 7) of the present invention were generated from colonies recovered from the second methyl cellulose step comprising a mixture of IL-3 and EPO. EBHX-8 through EBHX-11 (also referred to herein as Lines 8 through 11) of the present invention were generated from colonies recovered from the second methyl cellulose step comprising a mixture of C-kit ligand and EPO. EBHX-14 and EBHX-15 (also referred to herein as Lines 14 and 15) of the present invention were generated from colonies recovered from the first methyl cellulose step. EBHX-14 was generated from the methyl cellulose culture comprising a mixture of IL-3 and EPO, and EBHX-15 was generated from the methyl cellulose culture comprising a mixture of C-kit ligand and EPO. Following recovery, EBHX-15 was subsequently maintained in a culture comprising a mixture of IL-3 and EPO.

Example 15

This example describes the identification of cell surface markers on HOX11 immortalized pluripotent cell populations.

Approximately 2×10⁵ EBHX-1, EBHX-4, EBHX-11, EBHX-14 or EBHX-15 cells were incubated for 30 min on ice with 0.2 ml of culture supernatant containing anti-FcγRII/FcγRIII antibody from the 2.4G2 hybridoma (ATCC)

to block FcγRII and FcγRIII on the surface of the cells. The cells were then washed 3 times and incubated for 30 min on ice separately with one of the following antibodies directly labeled with FITC or biotinylated: anti-CD45 antibody (1:1000; a gift from John Cambier, National Jewish Center, Denver, Colo.), anti-Aa4.1 antibody (1:25; a gift from John McKearn, Monsanto, St. Louis, Mo.), anti-Sca-1 antibody (1:10; a gift from Jan Klein, Max-Planck Institute, Tubingen, Germany), anti-HSA antibody (1:10; a gift from John Cambier), anti-FcγRII/FcγRIII antibody (1:100; obtained from Pharmingen), anti-Thy-1 antibody (1:100; obtained from Pharmingen), anti-B220 antibody (1:100; obtained from Pharmingen), anti-Mac-1 antibody (1:20; obtained from Boehringer Mannheim, Montreal, PQ), anti-Gr-1 antibody (1:100; obtained from Pharmingen), anti-CD44 antibody (1:1000; Patrice Hugo, Research Institute of Montreal, Montreal, Canada), anti-VLA-4α antibody (1:10; obtained from ATCC) and anti-LFA-1β antibody (1:1000; obtained from Pharmingen). Cells incubated with biotinylated anti-Aa4.1, anti-Sca-1, anti-HSA and anti-VLA-4α antibodies were washed 3 times and counterstained with streptavidin, R-phycoerythrin conjugate (1:100; Molecular Probes, Inc., Eugene, Oreg.), Approximately $2 \times 10^5$ EBHX-1, EBHX-4, EBHX-11, EBHX-14 or EBHX-15 cells were incubated for 30 min on ice separately with either anti-VLA-4α, anti-ICAM-1 antibody (1:2 culture supernatant; obtained from ATCC) or anti-TER119 antibody (1:40; obtained from Pharmingen). The cells were then washed 3 times and labeled with FITC-conjugated goat F(ab')$_2$ anti-rat IgG (1:100; obtained from Jackson ImmunoResearch, West Grove, PN) for 30 min on ice, and analyzed on a Epics Elite flow cytometer (Coulter Electronics, Hialeah, Fla.).

The mean linear fluorescence signals obtained for cells incubated with all antibodies is shown in Table 2.

The results indicate that EBHX-1 cells express FcγRII and/or FcγRIII, Thy-1, CD44, VLA-4α and LFA-1β on their surface. The results using anti-TER119 antibody indicated that TER119 protein was most likely expressed on the surface of EBHX-1 cells. The results also indicated that EBHX-4 cells express FcγRII and/or FcγRIII, CD44, VLA-4α and LFA-1β on their surface. The results using anti-Thy-1 antibody indicated that Thy-1 protein was most likely expressed on the surface of EBHX-4 cells. Results obtained for EBHX-11 cells indicated that such cells express HSA, CD44, VLA-4α, LFA-1β and ICAM-1 on their surface. Moreover, results obtained for EBHX-14 cells indicated that such cells express CD45, Aa4.1, Sca-1, HSA, FcγRII and/or FcγRIII, Thy-1, Mac-1, Gr-1, CD44, VLA-4α and LFA-1β on their surface. The results using anti-TER119 antibody indicated that TER119 protein was most likely expressed on the surface of EBHX-14 cells. Results obtained for EBHX-15 cells indicated that such cells express CD45, Aa4.1, HSA, FcγRII, FcγRIII, Thy-1, Mac-1, Gr-1, CD44, VLA-4α, LFA-1β, ICAM-1 on their surface.

Example 16

This example describes the growth factor responsiveness of HOX11 immortalized pluripotent cell populations.

Approximately about $1 \times 10^5$ to about $10 \times 10^5$ EBHX-1, EBHX-11 or EBHX-14 cells were cultured in IMDM containing 15% PP-FBS, transferrin (300 µg/ml), glutamine (2 mM) and either IL-3 (saturating amounts) EPO (2 units/ml), C-kit ligand (100 ng/ml), LIF (10 ng/ml), IL-4 (saturating amounts), IL-6 (5 ng/ml), IL-11 (25 ng/ml), VEGF (5 ng/ml), GM-CSF 20 U/ml), M-CSF (100 U/ml), G-CSF (1000 U/ml) or in the absence of any factor. The EBHX cells were cultured in a final volume of 1 ml in a 35 mm bacterial grade dishes in a humidified environment of 5% $CO_2$ at 37° C. The EBHX cells were cultured for about 7 to about 10 days.

Figures 19, 20:
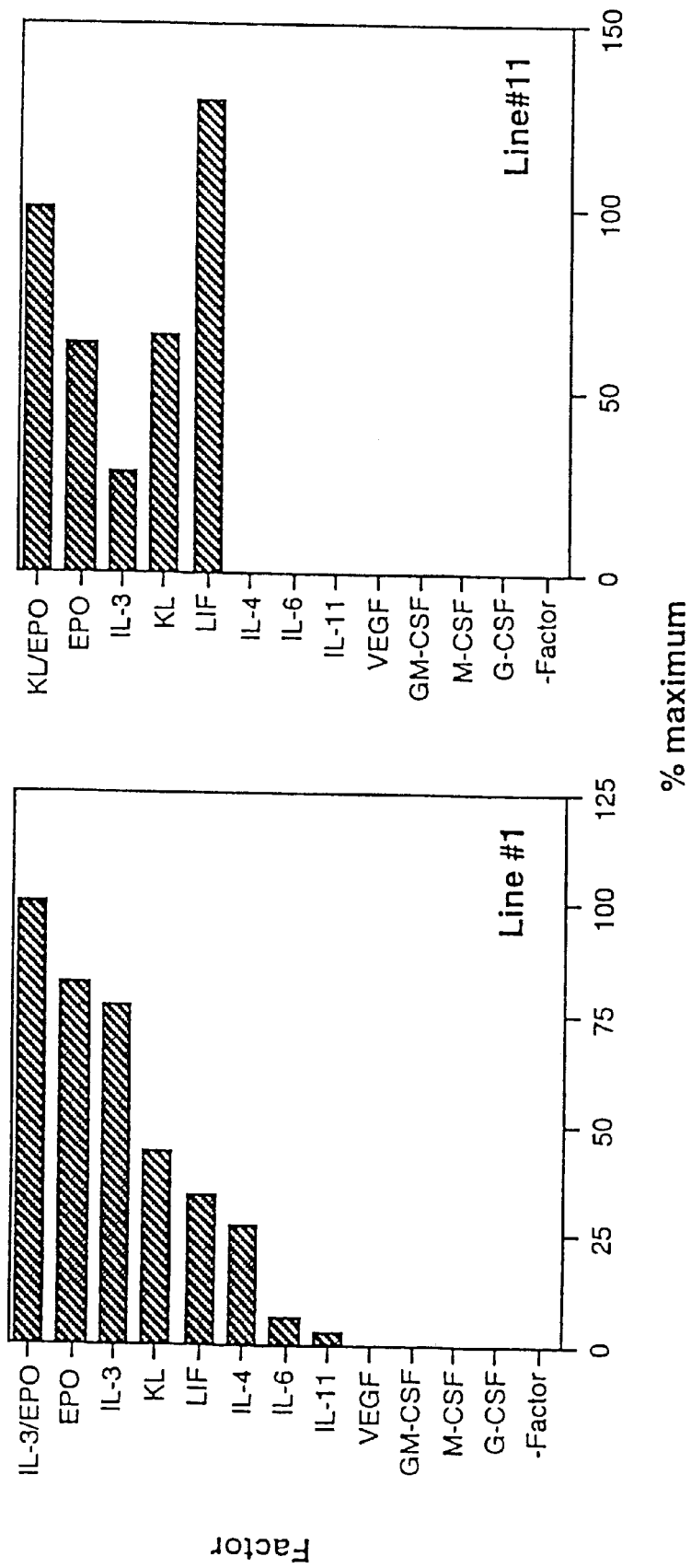
FIG. 19 the factor responsiveness of an EBHX-1 cell population.
FIG. 20 illustrates the factor responsiveness of an EBHX-11 cell population.
Figure 21:
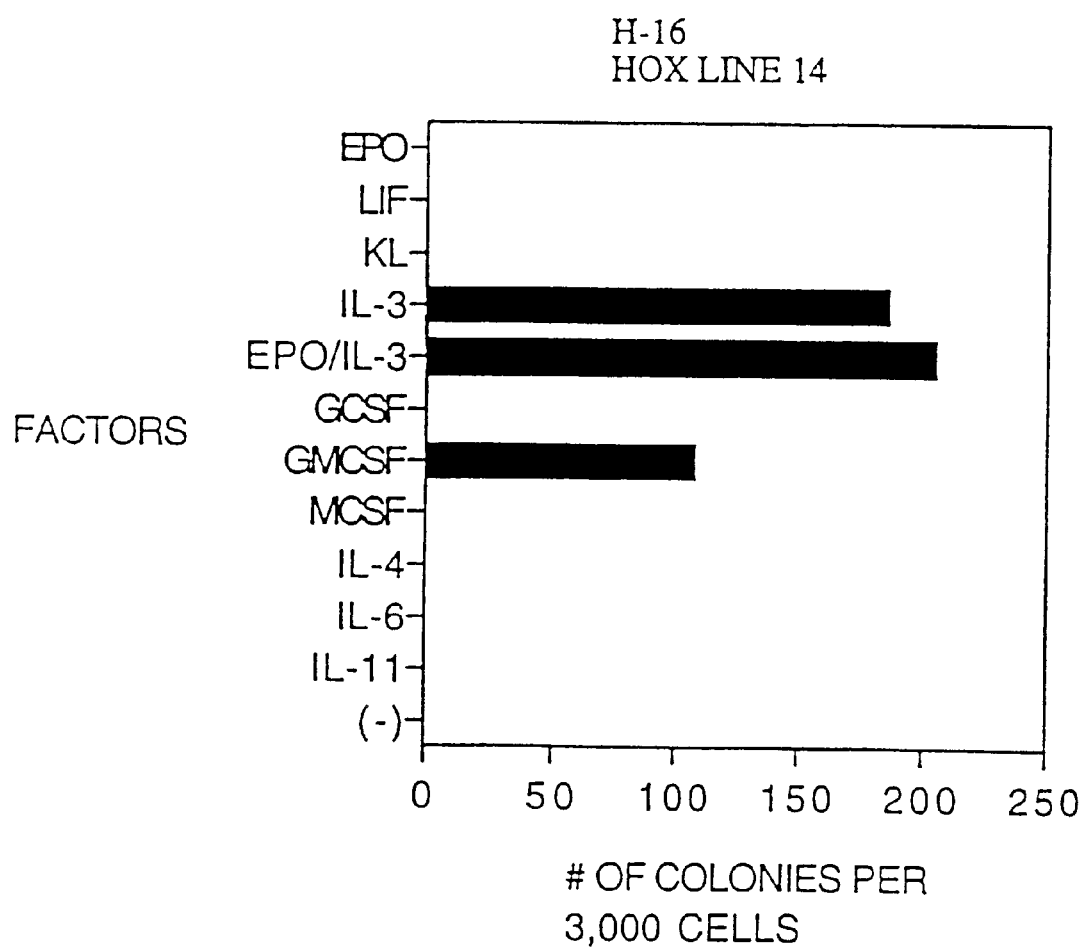
FIG. 21 illustrates the factor responsiveness of an EBHX-14 cell population.

Factor responsiveness to each EBHX cell population tested was determined by counting the number of colonies formed per about $1 \times 1^5$ to about $10 \times 10^5$ cells plated. The colony counts in the presence of a factor was then compared with the colony counts obtained for cells cultured in the absence of any factor. The results obtained for EBHX-1 cells are illustrated in FIG. 19 and indicate that EBHX-1 cells (Line #1) respond to a combination of IL-3 and EPO, EPO alone, IL-3 alone, c-kit ligand, LIF, IL-4, IL-6 and IL-11. In addition, the results obtained for EBHX-11 cells are illustrated in FIG. 20 and indicate that EBHX-11 cells (Line #11) respond to a combination of c-kit ligand and EPO, EPO alone, c-kit ligand alone, IL-3 and LIF. Moreover, the results obtained for EBHX-14 cells are illustrated in FIG. 21 and indicate that EBHX-14 cells (HOX Line 14) respond to a combination of IL-3 and EPO, IL-3 alone and GM-CSF.

TABLE 2

Surface Marker Analysis of HOX11-Expressing Cell Populations

| Marker | EBHX-1 | EBHX-4 | EBHX-11 | EBHX-14 | EBHX-15 |
|---|---|---|---|---|---|
| CD45 (Ly-5) | 0.9 (1.61) | 0.4 (1.99) | 0.2 (0.61) | 3.1 (2.26) | 84.8 (9.38) |
| Aa4.1* | 0.2 (0.79) | 0.3 (0.79) | 0.1 (0.65) | 7.2 (1.13) | 18.6 (3.25) |
| Sca-1 (Ly-6A/E)* | 0.4 (0.94) | 0.4 (0.80) | 0.1 (0.62) | 5.0 (1.38) | 1.1 (2.13) |
| HSA (CD24)* | 0.1 (0.93) | 0.2 (0.79) | 99.8 (6.55) | 4.6 (2.16) | 98.5 (12.5) |
| FcγRII/III (CD32/CD16) | 78.3 (3.66) | 85.6 (5.44) | 0.3 (0.55) | 91.1 (5.41) | 99.7 (39.8) |
| Thy-1 | 6.6 (4.81) | 3.2 (4.24) | 0.3 (0.53) | 86.3 (30.1) | 95.7 (63.3) |
| B220 (CD45R) | 0.7 (2.48) | 0.6 (2.14) | 0.3 (0.54) | 0.5 (1.60) | 0.4 (7.82) |
| Mac-1 (CD11b) | 0.7 (1.68) | 0.2 (1.45) | 0.3 (0.56) | 4.0 (2.65) | 11.8 (12.1) |
| Gr-1 (Ly-6G) | 0.7 (1.59) | 0.5 (2.13) | 0.3 (0.48) | 21.6 (19.7) | 6.3 (31.5) |
| CD44 | 91.6 (8.82) | 94.5 (10.2) | 98.8 (9.08) | 92.4 (7.48) | 9.9 (26.6) |
| VLA-4α (CD49d)* | 72.4 (1.45) | 98.0 (4.00) | 85.8 (1.06) | 99.7 (5.35) | 99.5 (6.27) |
| LFA-1β (CD18) | 96.9 (6.03) | 98.4 (7.17) | 0.3 (0.52) | 98.7 (9.72) | 98.5 (23.7) |
| ICAM-1 (CD54)† | 1.3 (1.82) | 0.5 (1.64) | 27.8 (0.78 ) | 0.5 (1.44) | 27.7 (9.2) |
| TER119† | 6.2 (1.80) | 0.9 (1.73) | 0.3 (0.73) | 12.1 (4.15) | 24.8 (8.59) |

Results are the percentages of labeled cells (log mean fluorescence intensity) determined by direct staining of FcγRII/III-blocked cells with FITC-conjugated antibodies
*direct staining of FcγRII/III-blocked cells with biotinylated antibodies and PE-streptavidin

Example 17

This example describes the expression of βH1, ζ and β major globin genes by EBHX-1 and EBHX-11 cells.

cDNA was prepared from mRNA isolated from approximately EBHX-1 or EBHX-11 cells using an oligo dT primer under standard conditions. The cDNA was resolved by gel electrophoresis and immobilized on a nylon membrane using methods standard in the art and described in Sambrook et al. (ibid.). The membranes were then hybridized in the presence of a $^{32}$P-labelled βH1-globin oligonucleotide probe (about $5\times10^6$ cpm/ml of hybridization buffer; disclosed in Hill et al., *J. Biol. Chem.* 259:3739–3744, 1984), a $^{32}$P-labelled β major-globin oligonucleotide probe (about $5\times10^6$ cpm/ml of hybridization buffer; disclosed in Konkel et al., *Cell* 15:1125–1132, 1978) or a $^{32}$P-labelled c-globin oligonucleotide probe (about $5\times10^6$ cpm/ml of hybridization buffer; disclosed in Leder et al., *Mol. Cell. Biol.* 5:1025–1033, 1985), using Churches hybridization buffer (containing 1 mM EDTA, 0.5 M $Na_2HPO_4$ at pH 7.2 and 7% SDS) for 18 hours at 42° C. The blots were then washed twice in wash buffer (containing 1 mM EDTA, 40 $Na_2HPO_4$ at pH 7.2 and 1% SDS) for 5 min at room temperature, and twice for 10 min at 42° C. The resulting blot was exposed to X-ray film to produce an autoradiogram.

The autoradiogram illustrated that βH1, ζ and β major-globin RNA was expressed in both EBHX-1 and EBHX-11 cells.

Taken together, the results described in Examples 13–17 indicate that the HOX11 immortalized cells of the present invention represent cells early in the hematopoietic lineage.

Example 18

This example describes the production of endothelial cell conditioned medium.

A. Production of an endothelial cell population from an EB cell population.

ES cells were prepared and cultured under conditions described in Example 1 for about 4 days to form a 4 day EB cell population. The EB cell population was then infected with retrovirus comprising DNA encoding Polyoma Middle T antigen and a neo gene conferring resistance to G418 using standard conditions (described in detail in Williams et al., ibid.). The retrovirus transformed EB cells were then cultured for about 7 to about 10 days in IMDM medium containing about 500 µg of G418 and about 5% to about 10% normal FCS. Surviving cells were then replated in culture medium lacking G418 and containing endothelial cell growth supplement (about 50 to 100 µg/ml of culture medium; Collaborative Research, Bedford, Mass.) and cultured under standard conditions for about 2 months. Rapidly growing cells from this population, referred to herein as ID4T, were recovered and frozen at −70° C. and stored.

D4T cells were then stained for FACS analysis using either anti-Flk-1 antibody (obtained from Warner Risan, Bad Nauheim, Germany) or anti-CD31 antibody (obtained from Pharmingen). The results from the FACS analysis indicated that D4T cells express both CD31 and Flk-1, thus indicating that the D4T cells possessed endothelial cell characteristics.

D4T cells were also tested for DiI-Ac-LDL uptake using methods described in Example 10. The results indicate that the D4T cells stained with DiI-Ac-LDL, confirming the results of the FACS analysis and indicating that the D4T cells posses endothelial cell characteristics.

B. Production of Conditioned Medium

About $5\times10^4$ D4T cells were cultured in IMDM medium comprising about 10% normal FCS and about 50 to 100 µg/ml of ECGF for about 72 hours at 37° C. The supernatant from the culture was recovered and filtered through a 0.2 micron filter.

C. Stimulation of BLAST Cell Population Growth Using Conditioned Medium.

Two separate series of 3 day EB cell (prepared according to the method in Example 1) cultures were prepared at cell densities of about $6\times10^3$, about $1\times10^4$, about $1.5\times10^4$, about $3\times10^4$ or about $5\times10^4$ cells per culture. The cultures were prepared and grown under conditions for BLAST cell colony formation (described in Example 3) using IMDM medium containing about 10% pre-selected FCS, EPO (2 units/ml), C-k:it ligand (100 ng/ml), VEGF (5 ng/ml), and either in the presence or absence of 25% final volume of D4T conditioned medium. The EB cells were cultured for about 4 days under standard conditions and the number of BLAST cell colonies were determined.

Figure 22:
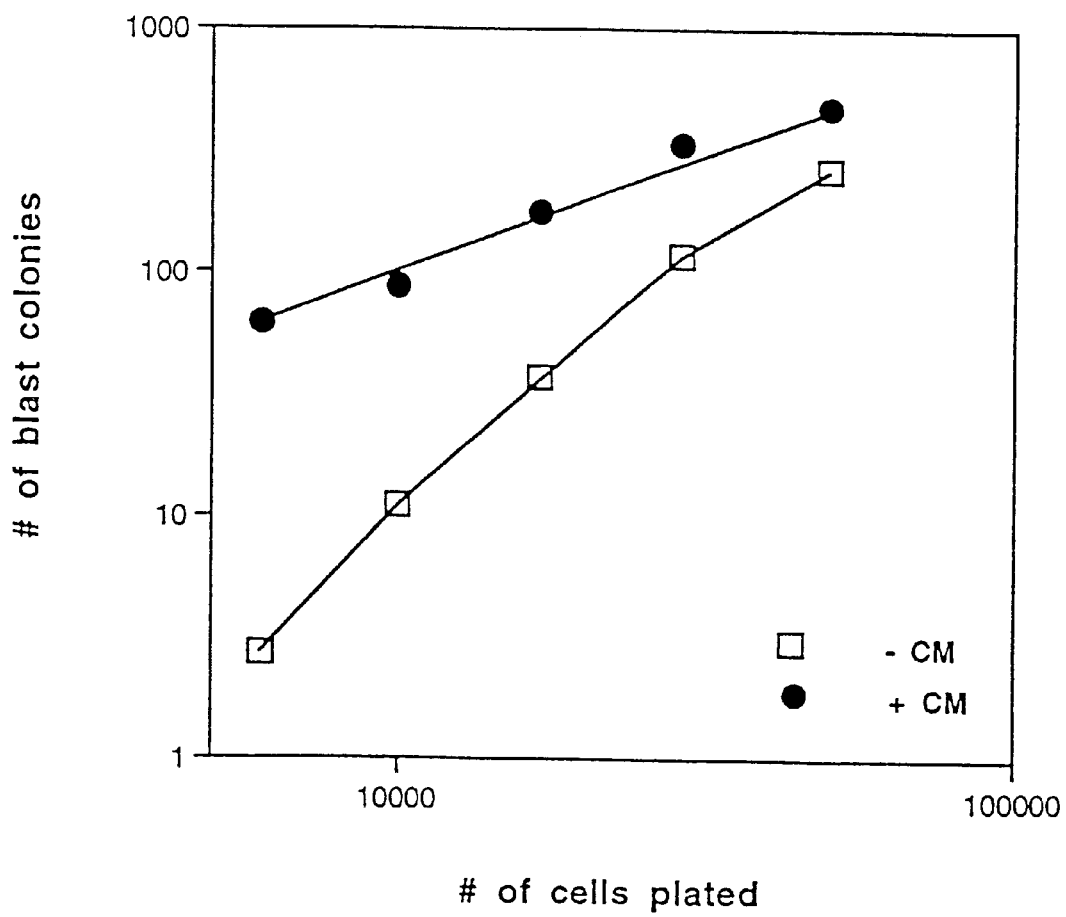
FIG. 22 illustrates the enhancement of BLAST cell growth when EB cells are grown in the presence of D4T conditioned medium.

The results (shown in FIG. 22) indicate that the addition of conditioned medium (+CM) in the culture medium improved BLAST cell growth compared with growth in the absence of conditioned medium (−CM), in particular at the lower cell densities. Thus, the D4T conditioned medium contains one or more compounds capable of enhancing the growth of B:LAST cells from EB cells.

---

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 1:

-continued

```
TGGTGGAGTC TGGGGGAGGC TTA                                          23

(2) INFORMATION FOR SEQ ID NO: 2:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

GGCTCCCTCA GGGACAAATA TCCA                                         24

(2) INFORMATION FOR SEQ ID NO: 3:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

CGCGGCCCCA AGCTTGTTAA CATCGATGGA TG                                32

(2) INFORMATION FOR SEQ ID NO: 4:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

GGCGTTACTT AAGCTAGCTT GCCAAAGGTA C                                 31
```

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed:

1. A method to identify at least one nucleic acid sequence associated with differentiation from embryonic stem cells, comprising:
   (a) comparing expression of at least one nucleic acid sequence expressed by a HOX11 precursor cell population to expression of at least one nucleic acid sequence expressed by a control cell population selected from the group consisting of an embryonic stem cell population, progeny of said HOX11 precursor cell population, a non-embryonic cell population, and a second embryonic precursor cell population that is different from said HOX11 precursor cell population; and
   (b) detecting at least one nucleic acid sequence that is expressed at a different level in the control cell population compared with the HOX11 precursor cell population;
   whereby a difference in expression level is associated with differentiation from embryonic cells;
   wherein said HOX11 precursor cell population expresses a HOX11 gene, wherein said HOX11 precursor cell population differentiates into primitive erythroid cell lineages, definitive erythroid cell lineages, and progeny thereof, and wherein said HOX11 precursor cell population is not totipotent.

2. The method of claim 1, wherein said HOX11 precursor cell population differentiates into primitive erythroid cell lineages, definitive erythroid cell lineages, endothelial cell lineages and progeny thereof.

3. The method of claim 1, wherein said HOX11 precursor cell population differentiates into primitive erythroid cells, definitive erythroid cells, macrophages, neutrophils, mast cells, T cells, endothelial cells, B cells, natural killer cells, megakaryocytes, eosinophils, and progeny thereof.

4. The method of claim 1, wherein said control cell population is a cell population comprising progeny of said HOX11 precursor cell population.

5. The method of claim 1, wherein said control cell population is a non-embryonic cell population.

6. The method of claim 1, wherein said control cell population is an embryonic stem cell population.

7. The method of claim 1, wherein said control cell population is a second embryonic precursor cell population that is different from said HOX11 precursor cell population.

8. The method of claim 1, wherein said step of detecting comprises detecting expression of an RNA sequence in said HOX11 precursor cell population as compared to said RNA sequence in said control cell population.

9. The method of claim 1, wherein said step of detecting comprises detecting a nucleic acid sequence in a sample comprising a cDNA product of RNA from said HOX11 precursor cell population as compared to a cDNA product of RNA from said control cell population.

10. The method of claim 1, wherein said step of detecting comprises detecting a nucleic acid sequence in a sample comprising amplified nucleic acid products of RNA from said HOX11 precursor cell population as compared to amplified nucleic acid products of RNA from said control cell population.

11. The method of claim 1, wherein said step of detecting comprises sequencing at least one nucleic acid sequence in said HOX11 precursor cell population and in said control cell population.

12. The method of claim 11, further comprising comparing the nucleic acid sequence from the HOX11 precursor cell population with at least one known nucleic acid sequence.

13. The method of claim 1, wherein said step of detecting comprises performing subtractive hybridization between a nucleic acid sample from said HOX11 precursor cell population and another nucleic acid sample from said control cell population.

14. The method of claim 1, wherein said step of detecting comprises:

contacting a nucleic acid sample from said HOX11 precursor cell population and a nucleic acid sample from said control cell population with a known nucleic acid sequence; and, detecting whether said known nucleic acid sequence hybridizes to either of said nucleic acid samples.

15. The method of claim 14, wherein said known nucleic acid sequence is selected from the group consisting of a hybridization probe and a polymerase chain reaction (PCR) primer.

* * * * *